(12) United States Patent
Begrow et al.

(10) Patent No.: US 11,254,066 B2
(45) Date of Patent: Feb. 22, 2022

(54) APPARATUS FOR FABRICATING AN ELASTIC NONWOVEN MATERIAL

(71) Applicant: DUKANE IAS, LLC, St. Charles, IL (US)

(72) Inventors: Brandon Leo Begrow, Hortonville, WI (US); Daniel James Sorensen, Neenah, WI (US); Thomas David Ehlert, Neenah, WI (US); Casey John Morin, Appleton, WI (US)

(73) Assignee: DUKANE IAS, LLC, St. Charles, IL (US)

( * ) Notice: Subject to any disclaimer, the term of this patent is extended or adjusted under 35 U.S.C. 154(b) by 0 days.

(21) Appl. No.: 16/825,579

(22) Filed: Mar. 20, 2020

(65) Prior Publication Data

US 2020/0299883 A1 Sep. 24, 2020

Related U.S. Application Data

(60) Provisional application No. 62/822,449, filed on Mar. 22, 2019.

(51) Int. Cl.
*B29C 65/00* (2006.01)
*D04H 5/06* (2006.01)
*B29C 65/06* (2006.01)

(52) U.S. Cl.
CPC .... *B29C 66/81435* (2013.01); *B29C 65/0681* (2013.01); *B29C 66/7294* (2013.01); *D04H 5/06* (2013.01); *D10B 2401/061* (2013.01)

(58) Field of Classification Search
CPC ........ B29C 65/0681; B29C 65/08–088; B29C 65/66; B29C 65/74; B29C 65/743;
(Continued)

(56) References Cited

U.S. PATENT DOCUMENTS

| 1,588,018 A | 6/1926 | Fitz |
| 3,993,532 A | 11/1976 | McDonald et al. |

(Continued)

FOREIGN PATENT DOCUMENTS

| CA | 1211745 A1 | 9/1986 |
| CN | 101868210 A | 10/2010 |

(Continued)

OTHER PUBLICATIONS

PCT International Search Report and Written Opinion for PCT Application PCT/US20/23908 dated Jun. 19, 2020; 16 pp.

*Primary Examiner* — John L Goff, II
(74) *Attorney, Agent, or Firm* — Armstrong Teasdale LLP

(57) ABSTRACT

An apparatus for fabricating an elastic nonwoven material generally includes a first bonding module and a second bonding module. The second bonding module is positionable in close proximity to the first bonding module for receiving a first nonwoven fabric, a second nonwoven fabric, and at least one elastic strand therebetween. The second bonding module has a face with a width dimension and a circumferential axis and is rotatable about a rotation axis. The face has a plurality of ridges includes a first ridge and a pair of second ridges positioned on opposing sides of the first ridge along the circumferential axis. The first ridge defines a plurality of interspaced lands and notches, and the second ridges are configured to sever the at least one elastic strand when in close proximity to the first bonding module.

17 Claims, 48 Drawing Sheets

(58) Field of Classification Search
CPC ............ B29C 65/7443; B29C 65/7455; B29C 66/7294; B29C 66/81433; B29C 66/81435; B29C 66/8432; B32B 5/022; B32B 7/05; B32B 37/0076; B32B 37/0084; B32B 37/14; B32B 37/144; B32B 37/26; B32B 38/004; B32B 38/0004; B32B 2310/028; B32B 2555/02; B32B 2262/0207; B32B 2037/262; B32B 2260/02; B32B 2305/20; B32B 2307/51; B32B 2307/58; B32B 37/0053; D04H 5/06; D04H 1/56; D04H 3/005; D04H 3/12; D04H 3/14; D04H 3/16; D10B 2401/061; D06C 3/08; D06C 13/00; D06C 15/02; D06C 15/06; D06C 19/00; A61F 13/15593; A61F 13/15601; A61F 13/15699; A61F 13/15739; A61F 13/49011; A61F 13/49014; A61F 13/49017; A61F 13/49019; A61F 13/4902; A61F 13/51464; A61F 2013/15869; A61F 2013/49025; A61F 2013/49026; A61F 2013/49028; A61F 2013/49031; A61F 2013/49033; A61F 2013/49034; A61F 2013/49036

USPC ......... 156/73.1–73.6, 229, 580.1, 580.2, 582
See application file for complete search history.

(56) References Cited

U.S. PATENT DOCUMENTS

| | | |
|---|---|---|
| 4,146,416 A | 3/1979 | Goldman |
| 4,305,988 A | 12/1981 | Koecher |
| 4,333,978 A | 6/1982 | Kocher |
| 4,430,148 A | 2/1984 | Schaefer |
| 4,650,530 A | 3/1987 | Mahoney et al. |
| 4,713,132 A | 12/1987 | Abel et al. |
| 4,758,293 A | 7/1988 | Samida |
| 5,000,806 A | 3/1991 | Merkatoris et al. |
| 5,325,555 A | 7/1994 | Whitley |
| 5,421,924 A | 6/1995 | Ziegelhoffer et al. |
| 5,525,175 A | 6/1996 | Blenke et al. |
| 5,530,979 A | 7/1996 | Whitley |
| 5,643,396 A | 7/1997 | Rajala et al. |
| 5,660,657 A | 8/1997 | Rajala et al. |
| 5,660,679 A | 8/1997 | Rajala et al. |
| 5,667,608 A | 9/1997 | Rajala et al. |
| 5,681,302 A | 10/1997 | Melbye et al. |
| 5,733,411 A | 3/1998 | Bett |
| 6,098,684 A | 8/2000 | Terawaki |
| 6,123,792 A | 9/2000 | Samida et al. |
| 6,165,298 A | 12/2000 | Samida et al. |
| 6,291,039 B1 | 9/2001 | Combe et al. |
| 6,309,487 B1 | 10/2001 | Herrin et al. |
| 6,340,782 B1 | 1/2002 | Kling et al. |
| 6,368,437 B1 | 4/2002 | Ziegelhoffer et al. |
| 6,574,944 B2 | 6/2003 | Capodieci |
| 7,059,103 B2 | 6/2006 | Ninomiya et al. |
| 7,060,142 B2 | 6/2006 | Yamamoto |
| 7,226,438 B2 | 6/2007 | Soga et al. |
| 7,299,600 B2 | 11/2007 | Caroli |
| 7,582,348 B2 | 9/2009 | Ando et al. |
| 7,642,398 B2 | 1/2010 | Jarpenberg et al. |
| 7,905,871 B2 | 3/2011 | Mueller et al. |
| 8,458,993 B2 | 6/2013 | Schiebout et al. |
| 8,647,319 B2 | 2/2014 | Een et al. |
| 8,662,133 B2 | 3/2014 | Ninomiya et al. |
| 9,731,454 B2 | 8/2017 | Tam et al. |
| 10,213,348 B2 | 2/2019 | Gualtieri et al. |
| 10,259,165 B2 | 4/2019 | Ehlert et al. |
| 2001/0008064 A1 | 7/2001 | Todd et al. |
| 2003/0089447 A1 | 5/2003 | Molee et al. |
| 2003/0111157 A1 | 6/2003 | Ehlert et al. |
| 2004/0166756 A1 | 8/2004 | Kurihara et al. |
| 2004/0219854 A1 | 11/2004 | Groitzsch et al. |
| 2005/0241773 A1 | 11/2005 | Schneider et al. |
| 2006/0069373 A1 | 3/2006 | Schlinz et al. |
| 2006/0144904 A1 | 7/2006 | Mlinar et al. |
| 2006/0228969 A1 | 10/2006 | Erdman |
| 2006/0270302 A1 | 11/2006 | Ando et al. |
| 2008/0119103 A1 | 5/2008 | Ng et al. |
| 2010/0193138 A1 | 8/2010 | Eckstein et al. |
| 2011/0123773 A1 | 5/2011 | Lofink et al. |
| 2012/0111483 A1 | 5/2012 | Schneider et al. |
| 2012/0186719 A1 | 7/2012 | Van Den Aker |
| 2013/0306226 A1 | 11/2013 | Zink et al. |
| 2014/0377506 A1 | 12/2014 | Eckstein et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0000662 A1 | 1/2017 | Schroer |
| 2017/0165131 A1 | 6/2017 | Varona et al. |
| 2018/0093444 A1 | 4/2018 | Begrow et al. |
| 2018/0169964 A1* | 6/2018 | Schneider ......... A61F 13/49061 |
| 2019/0231606 A1* | 8/2019 | Andrews ........... A61F 13/15699 |

FOREIGN PATENT DOCUMENTS

| | | |
|---|---|---|
| CN | 102325513 A | 1/2012 |
| CN | 104507436 B | 4/2015 |
| CN | 105142589 A | 12/2015 |
| CN | 106943236 A | 7/2017 |
| CN | 106999315 A | 8/2017 |
| CN | 108472182 A | 8/2018 |
| CN | 207804491 U | 9/2018 |
| EP | 0022896 B1 | 4/1983 |
| EP | 0677284 A1 | 10/1995 |
| EP | 0685586 A2 | 12/1995 |
| EP | 397123 A1 | 5/2000 |
| EP | 943305 B1 | 9/2003 |
| EP | 1609582 A1 | 12/2005 |
| EP | 1666178 A1 | 6/2006 |
| EP | 2186493 A1 | 5/2010 |
| EP | 1876275 B1 | 10/2011 |
| EP | 2412354 A1 | 2/2012 |
| EP | 2886089 A1 | 6/2015 |
| EP | 3056176 A1 | 8/2016 |
| EP | 3095589 A1 | 11/2016 |
| EP | 3429530 A1 | 1/2019 |
| FR | 2285975 A1 | 4/1976 |
| GB | 2378920 B | 12/2004 |
| IT | 1308626 B1 | 1/2002 |
| JP | S62225323 A | 10/1987 |
| JP | H0858007 A | 3/1996 |
| JP | H11291376 A | 10/1996 |
| JP | 2000080552 A | 3/2000 |
| JP | 3212615 B2 | 9/2001 |
| JP | 4383883 A | 5/2005 |
| JP | 3883530 B2 | 2/2007 |
| JP | 4322140 B2 | 8/2009 |
| JP | 2010115424 A | 5/2010 |
| JP | 4535771 A | 9/2010 |
| JP | 2010220781 A | 10/2010 |
| JP | 2010220782 A | 10/2010 |
| JP | 2010220783 A | 10/2010 |
| JP | 5085239 B2 | 11/2012 |
| WO | 9104724 A1 | 4/1991 |
| WO | 2004005018 A1 | 1/2004 |
| WO | 2009025975 A1 | 2/2009 |
| WO | 2009067055 A1 | 5/2009 |
| WO | 2010126415 A1 | 11/2010 |
| WO | 2013132404 A1 | 9/2013 |
| WO | 2014010365 A1 | 1/2014 |
| WO | 2014200102 A1 | 12/2014 |
| WO | 2016109514 A1 | 7/2016 |
| WO | 2018156817 A2 | 8/2018 |

* cited by examiner

APPARATUS FOR FABRICATING AN ELASTIC NONWOVEN MATERIAL

CROSS-REFERENCE TO RELATED APPLICATION

This application claims priority to U.S. Provisional Application No. 62/822,449 filed Mar. 22, 2019, which is hereby incorporated by reference in its entirety.

FIELD

Elastic nonwoven materials are utilized in a variety of articles including personal care articles (e.g., adult briefs, baby diapers, child/adult pull-on pants, contour fit hygiene products, etc.) and medical garments (e.g., masks, caps, gowns, footwear, etc.).

At least some conventional methods for fabricating elastic nonwoven materials include adhesively bonding elastic strands between layers of nonwoven fabric when the elastic strands are in tension. Once the elastic strands are permitted to contract, the elastic strands gather areas of the nonwoven fabric such that the nonwoven fabric functions with an elastic property. However, the durability of elastic nonwoven materials made by these conventional methods is less than desirable because the adhesive bonds are prone to creep, which can result in a loss of elasticity over time. Moreover, it can be overly expensive to fabricate elastic nonwoven materials using these conventional methods. It would be useful, therefore, to provide a system for fabricating a more durable elastic nonwoven material in a more cost effective manner.

SUMMARY

In one embodiment, an apparatus for fabricating an elastic nonwoven material generally comprises a first bonding module and a second bonding module. The second bonding module is positionable in close proximity to the first bonding module for receiving a first nonwoven fabric, a second nonwoven fabric, and at least one elastic strand therebetween. The second bonding module has a face with a width dimension and a circumferential axis and is rotatable about a rotation axis. The face has a plurality of ridges comprising a first ridge and a pair of second ridges positioned on opposing sides of the first ridge along the circumferential axis. The first ridge defines a plurality of interspaced lands and notches, and the pair of second ridges configured to sever the at least one elastic strand when in close proximity to the first bonding module.

In another embodiment, an apparatus for fabricating an elastic nonwoven material generally comprises a first bonding module and a second bonding module. The second bonding module is positionable in close proximity to the first bonding module for receiving a first nonwoven fabric, a second nonwoven fabric, and at least one elastic strand therebetween. The second bonding module has a face with a width dimension and a circumferential axis and is rotatable about a rotation axis. The face has a plurality of ridges arranged on the face to define a first zone and a second zone along the circumferential axis. At least one ridge in the first zone is configured to form at least one pair of first bond points for entrapping the at least one elastic strand therebetween, and at least one ridge in the second zone is configured to form at least one second bond point for severing the at least one elastic strand when in close proximity to the first bonding module.

In yet another embodiment, a method for fabricating an elastic nonwoven material generally comprises positioning a first bonding module in close proximity to a second bonding module. At least one of the first bonding module and the second bonding module includes a face with a width dimension and a circumferential axis. The method also includes rotating at least one of the first bonding module and the second bonding module. The method further includes feeding an elastic strand between the first bonding module and the second bonding module in a machine direction along the circumferential axis, and bonding the elastic nonwoven material in a first region, wherein at least a portion of the elastic strand is entrapped in the first region. The method also includes bonding the elastic nonwoven material in a second region, wherein the elastic strand is severed in the second region.

BRIEF DESCRIPTION OF THE DRAWINGS

Corresponding reference characters indicate corresponding parts throughout the several views of the drawings.

DETAILED DESCRIPTION

Figure 1:
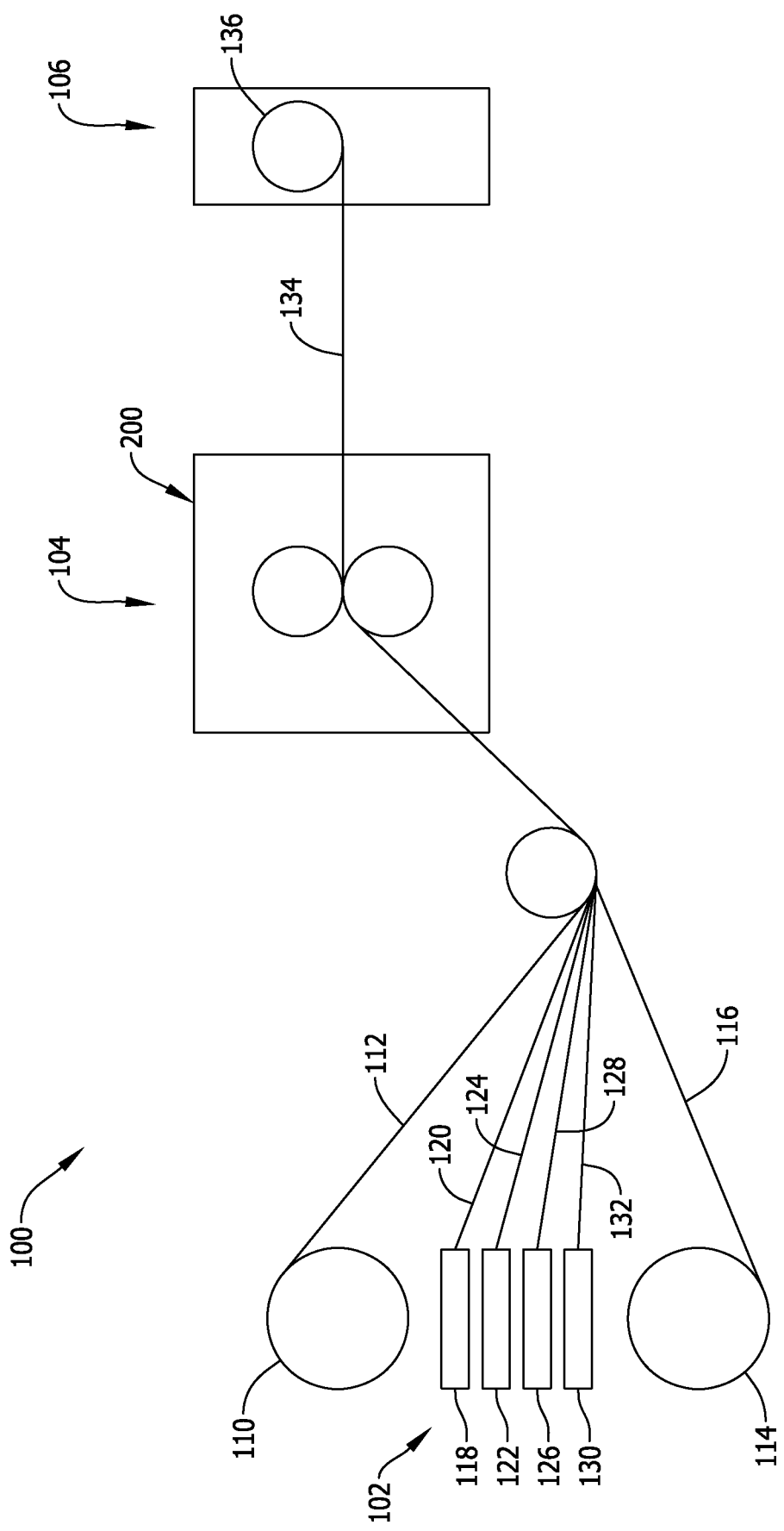
FIG. 1 is a schematic illustration of a system for fabricating an elastic nonwoven material.

Referring to the drawings, and in particular to FIG. 1, a system for fabricating an elastic nonwoven material is indicated generally by 100. The illustrated system 100 includes a supply station indicated generally by 102, a processing station indicated generally by 104, and a collection station indicated generally by 106. Other suitable stations are also contemplated without departing from the scope of this disclosure.

In the illustrated embodiment, the supply station 102 includes a plurality of supply rolls each containing a nonwoven fabric, namely a first supply roll 110 containing a first nonwoven fabric 112 and a second supply roll 114 containing a second nonwoven fabric 116. The supply station 102 also includes a plurality of supply spools each containing an elastic strand, namely a first supply spool 118 containing a first elastic strand 120, a second supply spool 122 containing a second elastic strand 124, a third supply spool 126 containing a third elastic strand 128, and a fourth supply spool 130 containing a fourth elastic strand 132. The elastic strands 120, 124, 128, 132 may have any suitable cross-sectional shape that facilitates enabling the elastic strands 120, 124, 128, 132 to function as described herein (e.g., a cross-sectional shape that is round, rectangular (e.g., relatively flat), square, etc.).

The illustrated processing station 104 includes a rotary ultrasonic bonding apparatus (indicated generally by 200) for bonding the elastic strands 120, 124, 128, 132 between the nonwoven fabrics 112, 116 to make an elastic nonwoven material 134, as set forth in more detail below. The collection station 106 may include any suitable device(s) for collecting the elastic nonwoven material 134 (e.g., a puller roll 136). In other embodiments, the supply station 102 may have any suitable quantity of supply rolls and supply spools having any suitable configuration that facilitates enabling the apparatus 200 to function as described herein.

FIGS. 2-7 are various embodiments of the rotary ultrasonic bonding apparatus 200. In the illustrated embodiments, the apparatus 200 has bonding modules, e.g., an anvil module 202 and a horn module 204, that cooperate to perform a bonding operation of the elastic strands 120, 124, 128, 132 between the nonwoven fabrics 112, 116 as set forth in more detail below.

In the illustrated embodiments, the horn module 204 includes a frame 206 on which are mounted a disc-like rotary horn 208, a motor 210 for driving rotation of the horn 208 via a suitable drive train 212, and a housing 214 which contains at least part of a vibration control unit (not shown) that causes the horn 208 to vibrate. The horn 208 has a face 216 with a substantially continuous contour (i.e., the horn face 216 has a contour that is substantially smooth (or uninterrupted) across its entire surface area). In other embodiments, the horn face 216 may have any suitable contour that facilitates enabling the horn 208 to function as described herein.

In some embodiments, the vibration control unit (while not illustrated) includes at least one booster (e.g., a drive booster and an integral booster) mechanically connected to a converter, which is electrically connectable to a generator. The converter is capable of converting high frequency electrical energy supplied by the generator into mechanical energy (or vibration) that is selectively transmitted to the horn 208 across the booster(s). The booster(s) are capable of modifying (i.e., increasing or decreasing) the vibration transmitted to the horn 208 from the converter, such that the horn 208 (particularly, the face 216 of the horn 208) vibrates while it rotates during a bonding operation, as set forth in more detail below. It is contemplated that the horn module 204 may have any suitable operational components arranged in any suitable manner that facilitates enabling the horn 208 to function as described herein.

In the illustrated embodiments, the anvil module 202 includes a frame 218 on which are mounted a disc-like rotary anvil 220 and a motor 222 for driving rotation of the anvil 220 via a suitable drive train 224. The anvil 220 has an annular face 226, the contour of which is not continuous (i.e., is interrupted) as set forth in more detail below. The anvil module 202 is positioned relative to the horn module 204 such that the anvil face 226 is rotatable in close proximity to the horn face 216, and vice versa, to facilitate ultrasonically bonding the elastic strands 120, 124, 128, 132 between the nonwoven fabrics 112, 116 when the elastic strands 120, 124, 128, 132 are held in tension across apparatus 200, as set forth in more detail below. As used herein, the term "close proximity" refers to when the anvil face 226 is either in contact with, or is minimally spaced apart from, the horn face 216 when the horn 208 is not ultrasonically vibrating.

In some embodiments, the apparatus 200 may be configured such that at least one of the anvil module 202 and the horn module 204 is displaceable relative to the other via a suitable displacement mechanism operable either: (A) when the system 100 is offline and the horn 208 is at rest (i.e., when the horn 208 is not rotating or vibrating); or (B) when the system 100 is online and the horn 208 is active (i.e., when the horn 208 is rotating and vibrating).

Figure 2:
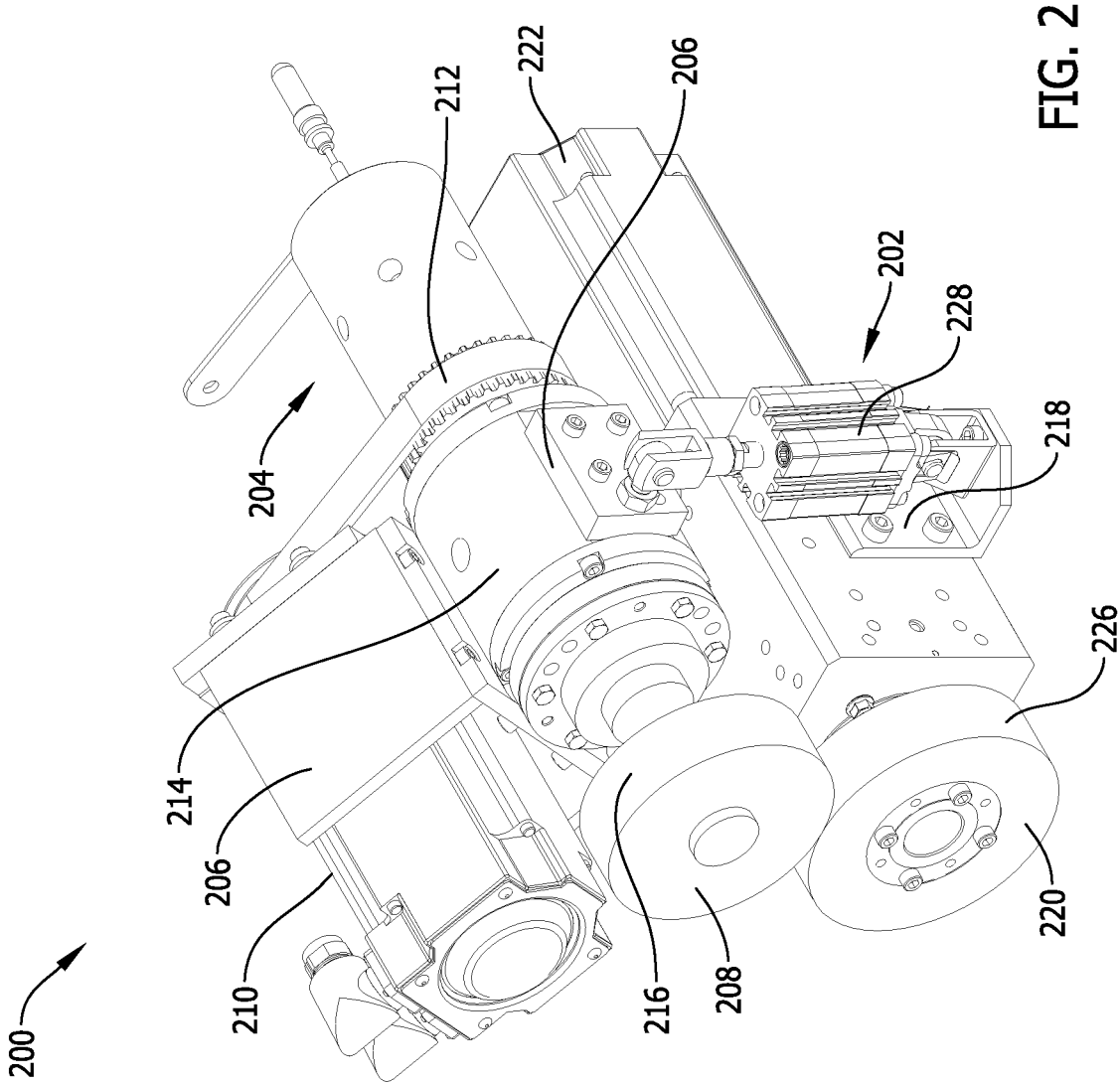
FIG. 2 is a perspective view of one embodiment of a rotary ultrasonic bonding apparatus for use in the system of FIG. 1.

With particular reference to the embodiment of FIG. 2, the apparatus 200 may be configured as a continuous-nip apparatus in which the horn module 204 is to be: (A) fixed in position relative to the anvil module 202 when the system 100 is online and the horn 208 is active; and (B) displaceable relative to the anvil module 202 when the system 100 is offline and the horn 208 is at rest. Such displacement is facilitated by a selectively actuatable pneumatic cylinder 228 (or other suitable linear actuator) that connects the frames 206, 218 to one another. In this manner, the spacing between the horn face 216 and the anvil face 226 is adjustable primarily for servicing the apparatus 200 when the system 100 is offline.

Figure 3:
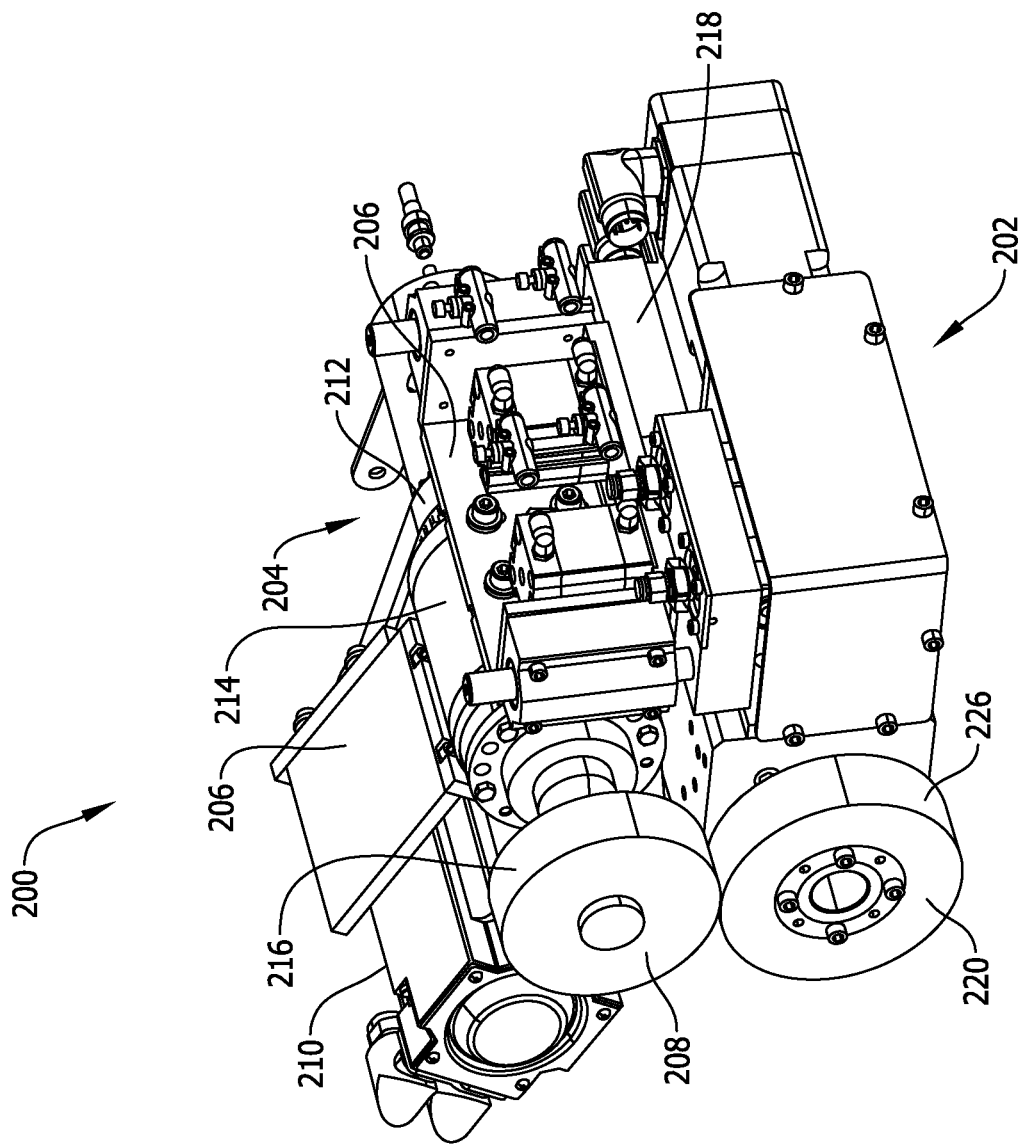
FIG. 3 is a perspective view of another embodiment of a rotary ultrasonic bonding apparatus for use in the system of FIG. 1.
Figure 4:
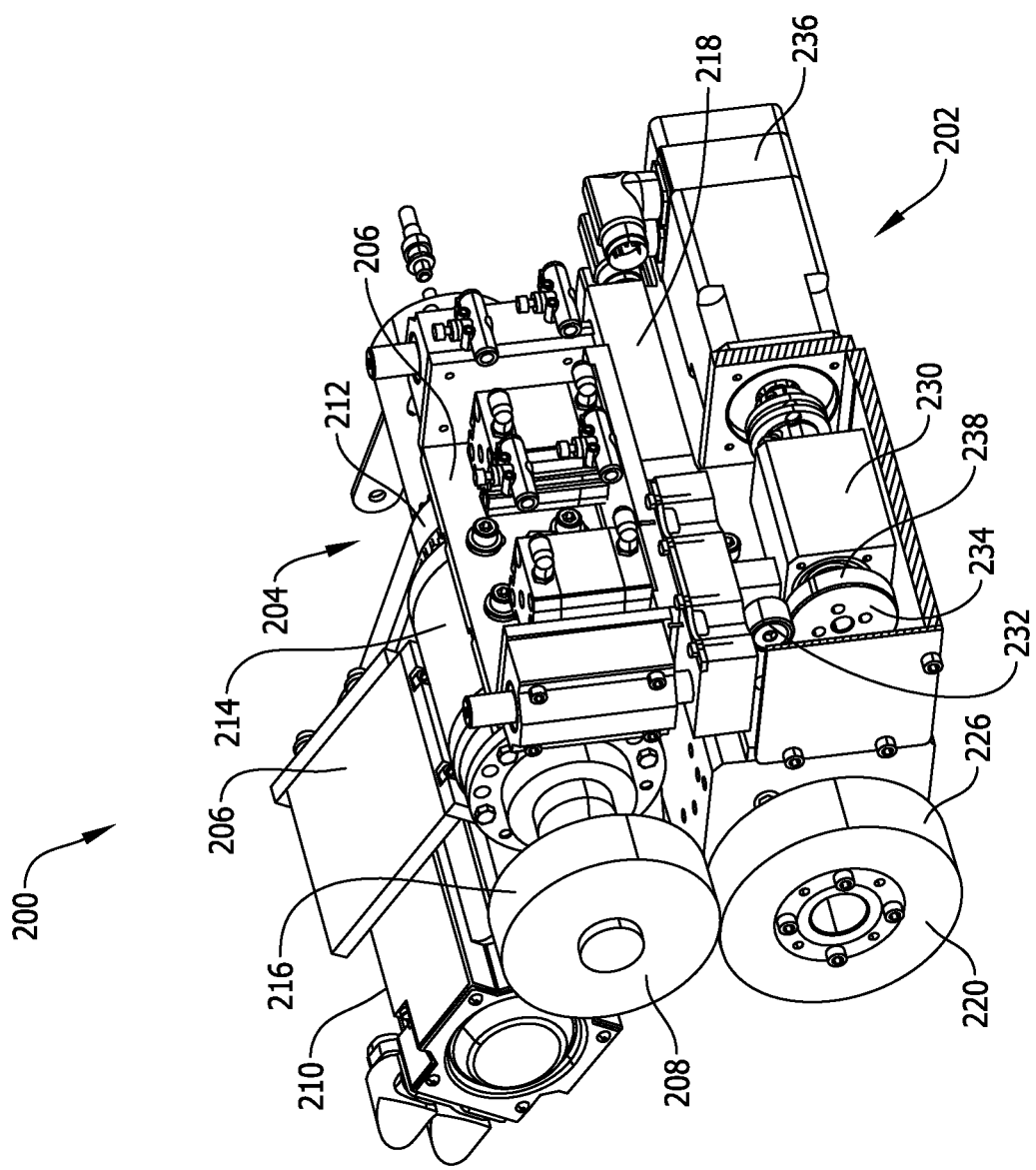
FIG. 4 is a partial cross-section of the apparatus of FIG. 3.

Referring now to the embodiment of FIGS. 3 and 4, the apparatus 200 may also be configured as an intermittent-nip apparatus in which the horn module 204 is displaceable relative to the anvil module 202 via a rotary camming device 230 when the system 100 is online and the horn 208 is active. The rotary camming device 230 has a follower 232 mounted to the horn module frame 206, and a cam wheel 234 mounted to the anvil module frame 218 and rotatable via a servomotor 236. The cam wheel 234 has an irregular camming surface 238 such that, when the cam wheel 234 is rotated via the servomotor 236, the follower 232 rides along the irregular camming surface 238 to cyclically displace the horn module frame 206 relative to the anvil module frame 218 at a predetermined frequency. In this manner, the spacing between the horn face 216 and the anvil face 226, and/or the frequency at which the horn face 216 contacts the anvil face 226, are selectively adjustable. Other displaceable arrangements of the horn module 204 and the anvil module 202 are also contemplated without departing from the scope of this disclosure.

Figure 5:
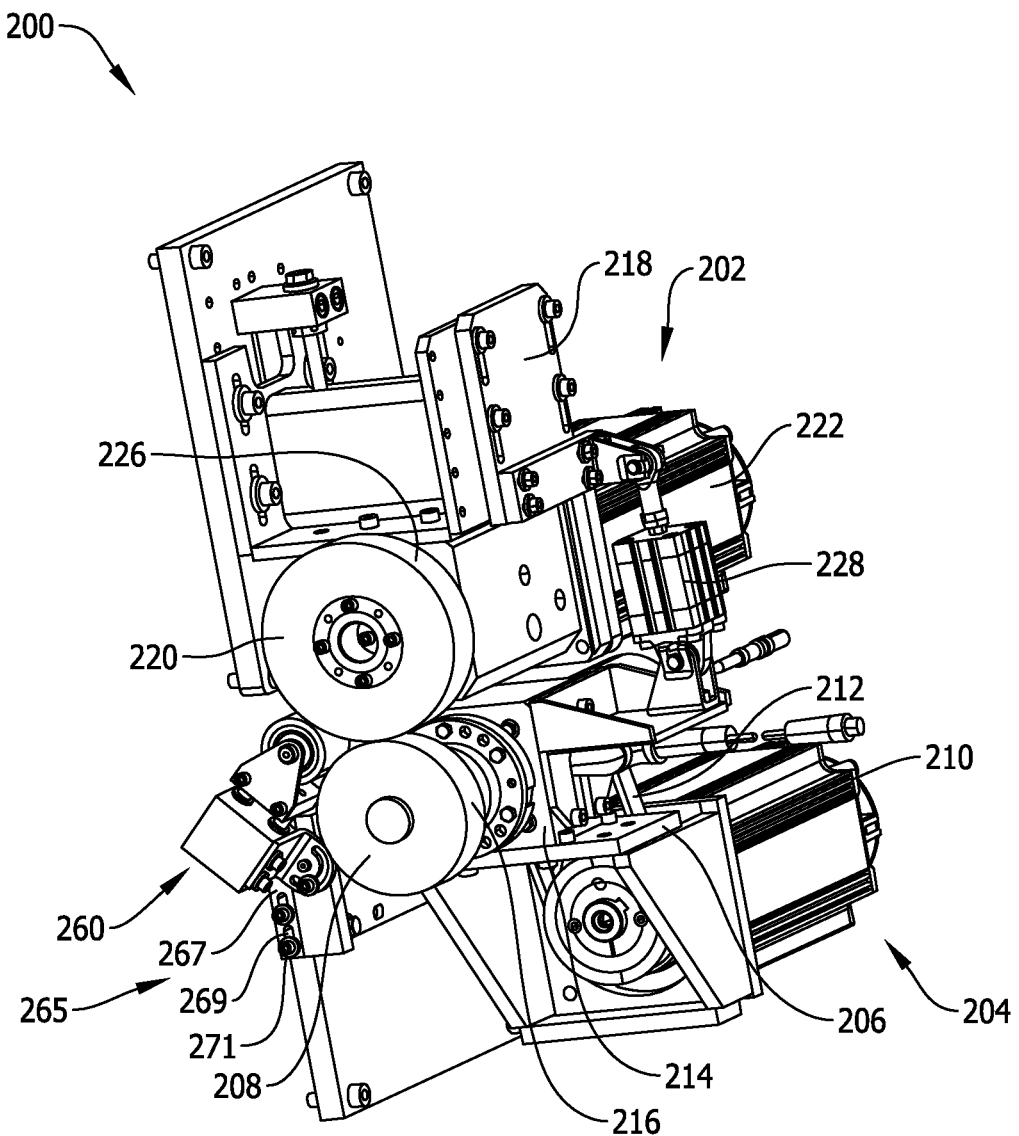
FIG. 5 is a perspective view of another embodiment of a rotary ultrasonic bonding apparatus for use in the system of FIG. 1.
Figure 6:
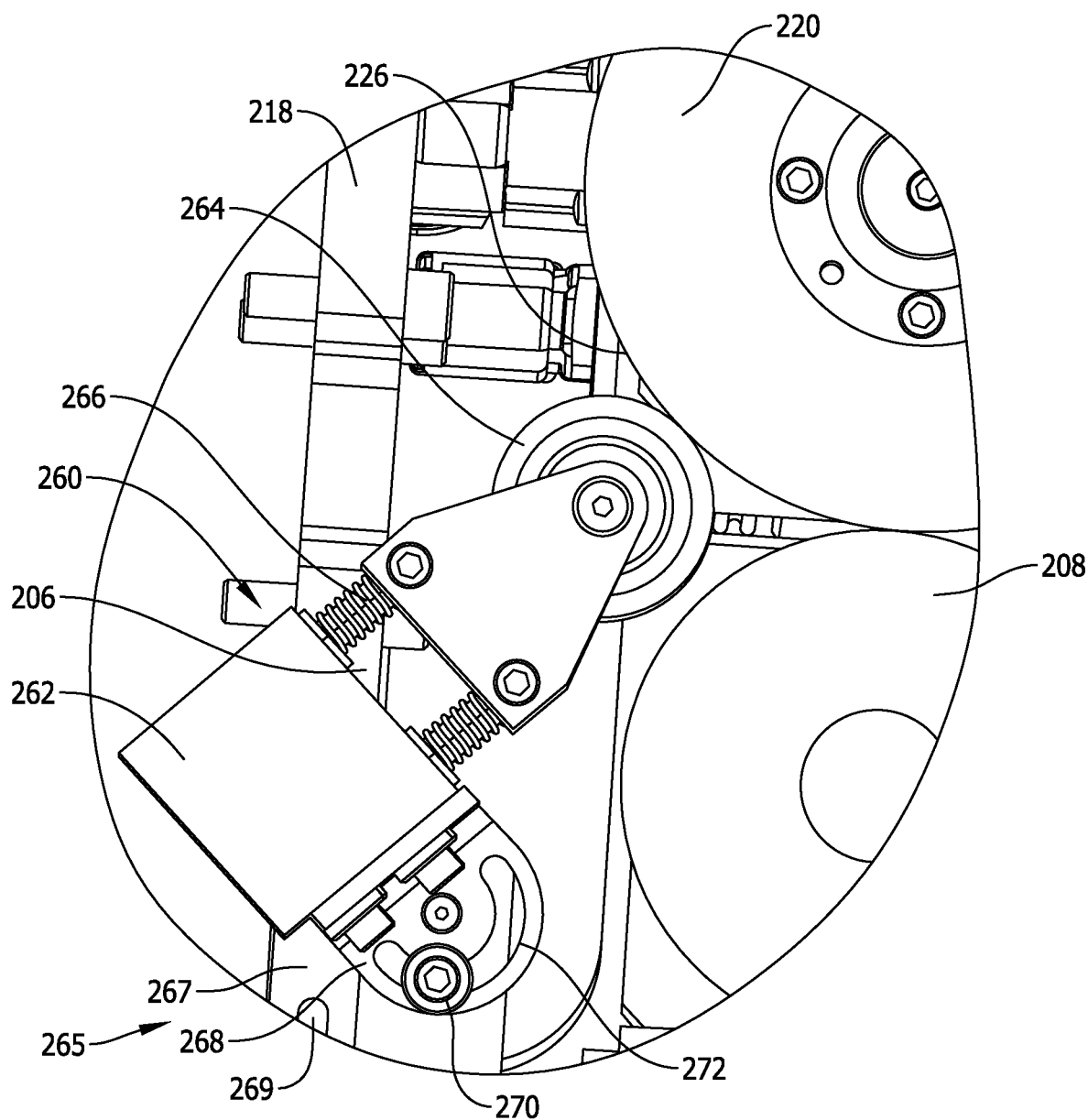
FIG. 6 is an enlarged side elevation view of a pinching device of the apparatus of FIG. 5.

As shown in the embodiment of FIGS. 5 and 6, the apparatus 200 may also include a pinching device 260. In the illustrated embodiment, the pinching device 260 includes a base 262 and a roller 264 floatingly mounted to the base 262 via at least one biasing element 266. The pinching device 260 also includes a bracket assembly 265 by which the base 262 and the roller 264 are mounted to at least one of the frame 206 and the frame 218, such that the base 262 and the roller 264 are adjustable in at least two degrees of freedom (as set forth in more detail below) in relation to the anvil 220 to facilitate use of the pinching device 260 in conjunction with anvils of different sizes.

The illustrated bracket assembly 265 includes a first bracket 267 and a second bracket 268. The first bracket 267 has at least one linear slot 269 through which a bolt 271 (which is fixed to either the frame 206 of the horn module 204 or the frame 218 of the anvil module 202) extends, and along which the bolt 271 is slidable, thereby rendering the first bracket 267 translatable relative to the frame 206 and/or 218. The second bracket 268 has at least one substantially arcuate slot 272 through which a bolt 270 (which is fixed to the first bracket 267) extends, and along which the bolt 270 is slidable, thereby rendering the second bracket 268 rotatable relative to the first bracket 267. The base 262 is mounted to the second bracket 268 such that the base 262 (and, therefore, the roller 264) are rotatably adjustable in a first degree of freedom via rotation of the second bracket 268, and are translatably adjustable in a second degree of freedom via translation of the first bracket 267.

The position of the base 262 and, therefore, the roller 264 are fixable via the bolt 270 and the bolt 271 to achieve a desired pinching contact between the roller 264 and the anvil face 226. For example, in the illustrated embodiment, the base 262 and the roller 264 are oriented such that the biasing element 266 applies a biasing force oriented substantially perpendicular to a rotation axis of the anvil 220 when viewed as in FIG. 6. In other embodiments, the pinching device 260 may have any suitable components arranged and movable (e.g., translatable and/or rotatable) in any suitable manner that facilitates enabling the pinching device 260 to perform the pinching action described herein (e.g., on any suitable bracket assembly that facilitates enabling the base 262 and the roller 264 to be adjustable in at least two degrees of freedom such as, for example, two translating degrees of freedom, or one translating degree of freedom and one rotating degree of freedom).

In this manner, the pinching device 260 limits the snapback potential of elastic strands 120, 124, 128, 132 that become severed between horn 208 and anvil 220 during a bonding operation. More specifically, the pinching device 260 effectively catches broken elastic strand(s) 120, 124, 128, 132 between the roller 264 and the anvil 220 to prevent the broken elastic strands 120, 124, 128, 132 from snapping back to their respective supply spool(s) 118, 122, 126, 130. Moreover, because the roller 264 rotates by virtue of being in contact with anvil 220, any broken elastic strands 120, 124, 128, 132 are caught at the interface of roller 264 and anvil 220 and are automatically fed back into the interface between horn 208 and anvil 220. As such, the pinching device 260 serves as a self-threading device for broken elastic strands 120, 124, 128, 132.

Figure 7:
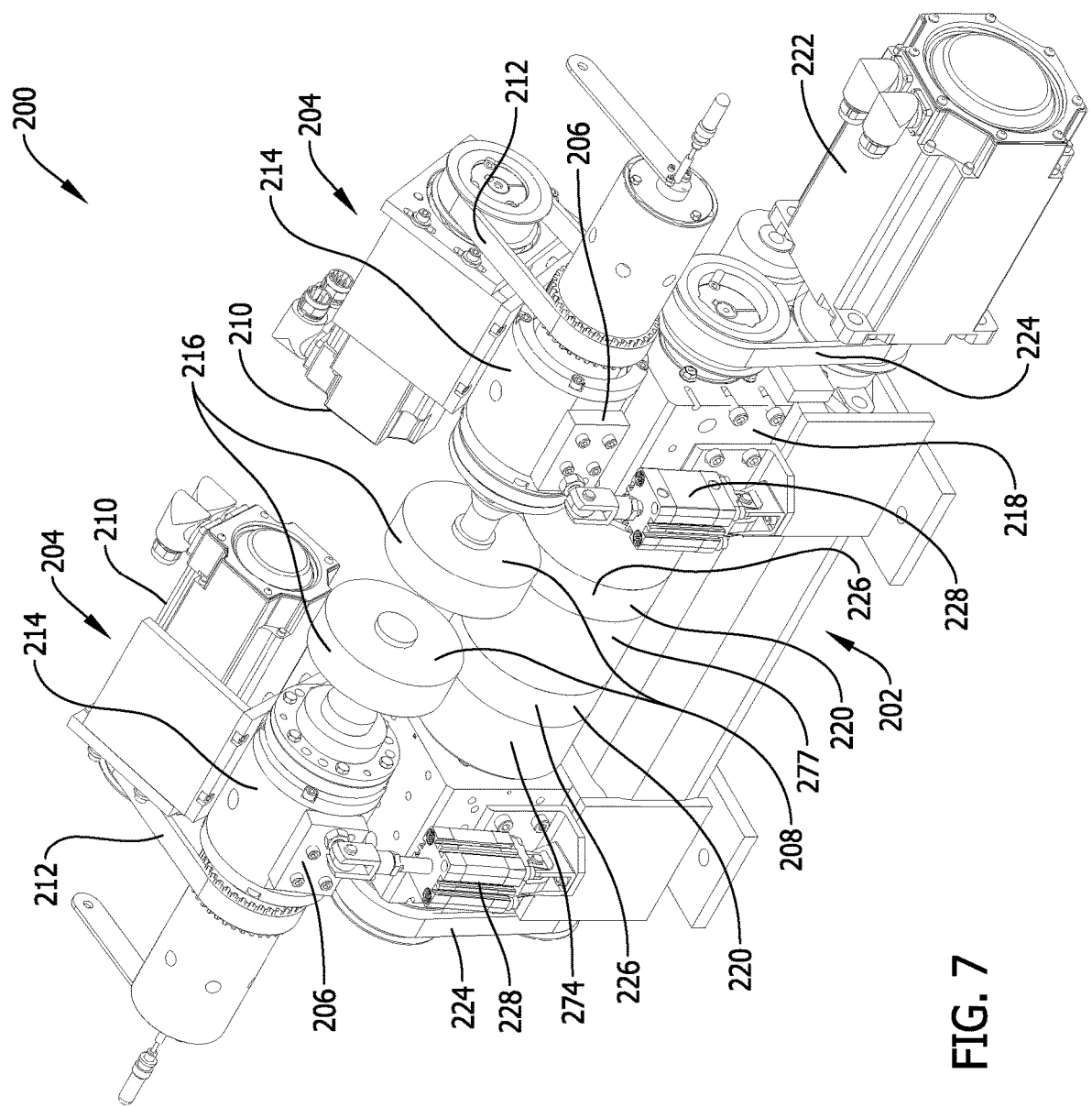
FIG. 7 is a perspective view of yet another embodiment of a rotary ultrasonic bonding apparatus for use in the system of FIG. 1.

Notably, the apparatus 200 may have any suitable quantity of anvil modules 202 and/or horn modules 204 that cooperate with one another to facilitate enabling the apparatus 200 to function as described herein. For example, as illustrated in the embodiment of FIG. 7, the apparatus 200 may be configured with an anvil drum 274 in which a pair of anvils 220 are positioned such that the drum 274 has a pair of predefined, annular faces 226 that are spaced apart from one another. In this manner, the horn 208 of a separate horn module 204 is dedicated to each such anvil face 226, thereby facilitating a bonding operation on confined regions of larger nonwoven fabrics on which only partial elasticity is desired (e.g., segments of these larger nonwoven fabrics on which elasticity is not desired may move along non-contact regions 277 of the drum 274 to avoid interaction with the associated horn(s) 208).

To facilitate minimizing the occurrence of elastic strands 120, 124, 128, 132 being cut between the horn 208 and the anvil 220 during a bonding operation, it is desirable to effectively hold the elastic strands 120, 124, 128, 132 in place within notches of the anvil face 226 while the nonwoven fabrics 112, 116 are bonded together between the horn 208 and the anvil 220. At least the following operational parameters contribute to minimizing the occurrence of elastic strands 120, 124, 128, 132 being cut during a bonding operation: (A) the specific energy source (e.g., the amplitude of vibration of the horn 208 and its pressure when contacting the anvil 220); (B) the energy director (e.g., the geometry of the anvil face 226); and (C) the material system (e.g., the decitex and tension of the elastic strands 120, 124, 128, 132, and the basis weight of the nonwoven fabrics 112, 116).

Figure 8:
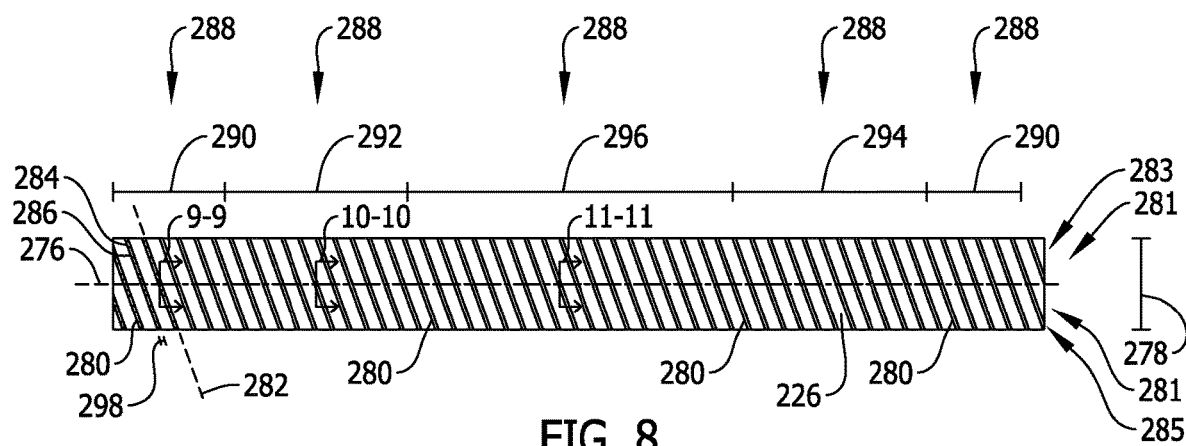
FIG. 8 is a laid-flat illustration of an annular face of one embodiment of an anvil for use in the apparatuses of FIG. 2-7.

With respect to one such parameter (i.e., the geometry of the anvil face 226), FIG. 8 is a laid-flat illustration of an embodiment of the anvil face 226 of the apparatus 200. In the illustrated embodiment, the anvil face 226 has a circumferential axis 276 and a width dimension 278 oriented perpendicular to the axis 276. The contour of the anvil face 226 is irregular (i.e., not continuous) along the axis 276, in that the anvil face 226 defines a plurality of circumferentially spaced ridges 280. For example, in some embodiments, each adjacent pair of ridges 280 may have a spacing (or pitch) measured along the axis 276 of between about 0.10 inch and about 1.00 inch (e.g., between about 0.20 inch and about 0.50 inch). While all adjacent pairs of ridges 280 on the anvil face 226 are substantially equally spaced apart from one another in the illustrated embodiment, it is contemplated that the spacing between adjacent pairs of ridges 280 may vary along the axis 276 in other embodiments.

Figure 9:
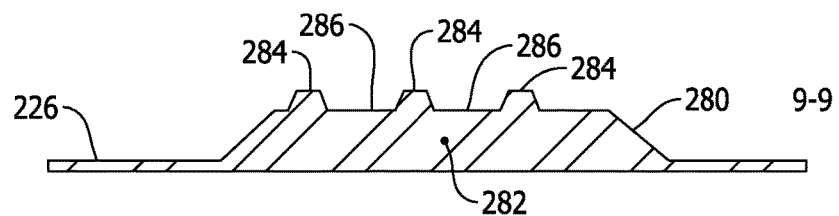
FIG. 9 is a cross-section, taken along plane 9-9 of FIG. 8, of one embodiment of a ridge defined by the anvil face of FIG. 8.

In the illustrated embodiment, each ridge 280 extends substantially linearly across the circumferential axis 276 so as to span substantially the entire width dimension 278 of the anvil face 226. Each ridge 280 has an extension axis 282 oriented oblique to the circumferential axis 276. As illustrated in FIG. 9, each ridge 280 includes a plurality of lands 284 spaced along its extension axis 282 such that each adjacent pair of lands 284 is spaced apart by (or flank) a notch 286. While the lands 284 and notches 286 are illustrated on only a select few of the ridges 280 in FIG. 8, it is understood that all ridges 280 of anvil face 226 likewise have a set of lands 284 and notches 286 along their respective extension axes 282. Notably, adjacent ones of the lands 284 of each ridge 280 are shaped such that the corresponding notch 286 defined therebetween is oriented substantially parallel to the circumferential axis 276 (i.e., the ridges 280 and the notches 286 each have a lengthwise dimension 298 that is oriented substantially parallel to the circumferential axis 276 in the illustrated embodiment).

In some embodiments, the anvil face 226 may be configured for a continuous entrapment bonding operation. More specifically, in such embodiments, each of the ridges 280 has at least one notch 286 that is aligned in the width dimension 278 with a corresponding notch 286 of each other ridge 280, and the lands 284 that flank each aligned notch 286 are spaced to create widthwise adjacent bonds in the nonwoven fabrics 112, 116 that are close enough together in the width dimension 278 to permanently hold the associated elastic strand 120, 124, 128, 132 in tension therebetween. As a result, after the bonding operation is complete and the nonwoven fabrics 112, 116 are removed from the system 100, at least one of the elastic strands 120, 124, 128, 132 is subsequently permitted to contract between circumferentially adjacent rows of bonds, but not between the widthwise adjacent bonds through which the elastic strand(s) 120, 124, 128, 132 extend. The entrapment bonding operation is therefore said to be continuous in the sense that at least one of the elastic strands 120, 124, 128, 132 is caused to be permanently held in tension between each widthwise adjacent pair of bonds through which it extends.

In one embodiment of a continuous entrapment configuration of the anvil face 226, the lands 284 and the notches 286 of each ridge 280 have sizes (and, therefore, spacings) relative to one another that are substantially the same as those of all other ridges 280 on the anvil face 226. The notches 286 are generally U-shaped or generally V-shaped, such that the sidewalls of the lands 284 that flank each notch 286 may, when viewed from a cross-sectional profile of the notch 286 as shown in FIG. 9, form a wedge angle therebetween of between about 1° and about 140° (e.g., between about 60° and about 100°). Notches 286 of other shapes are also contemplated. For example, in some embodiments, the sidewalls may form an angle of about 0° (i.e., the sidewalls may be about parallel to one another).

In one particular embodiment, if the elastic strands 120, 124, 128, 132 have a decitex of between about 300 and about 1240, and if the nonwoven fabrics 112, 116 have a grammage (gsm) of between about 8 and about 30, the lands 284 may have lengths at their peaks of between about 0.010 inch and about 0.25 inch (e.g., between about 0.030 inch and about 0.060 inch), and widths at their peaks of between about 0.008 inch and about 0.050 inch (e.g., between about 0.010 inch and about 0.030 inch). Also, in that example, the notches 286 may have: depths measured from the peaks of their flanking lands 284 of between about 0.002 inch and about 0.040 inch (e.g., between about 0.004 inch and about 0.02 inch); widths measured at the peaks of their flanking lands 284 of between about 0.006 inch and about 0.016 inch (e.g., between about 0.008 inch and about 0.015 inch); and widths measured at their bases of between about 0.002 inch and about 0.02 inch (e.g., between about 0.004 inch and about 0.015 inch).

By providing the lands 284 and the notches 286 with the dimensions of the above example, the anvil face 226 facilitates improved gripping of the elastic strands 120, 124, 128, 132 in the notches 286 and, therefore, facilitates preventing the elastic strands 120, 124, 128, 132 from withdrawing out of the notches 286 to reduce the occurrence of severed elastic strands 120, 124, 128, 132. Other suitable sizes for the lands 284 and the notches 286 are also contemplated without departing from the scope of this disclosure.

In other embodiments, the anvil face 226 may be configured for an intermittent entrapment bonding operation, such that the lands 284 that flank at least one of the notches 286 are spaced to create widthwise adjacent bonds in the nonwoven fabrics 112, 116 that are not close enough together in the width dimension 278 to permanently hold the associated elastic strand 120, 124, 128, 132 in tension therebetween. As a result, after the bonding operation is complete and the nonwoven fabrics 112, 116 are removed from the system 100, the corresponding elastic strand 120, 124, 128, 132 is subsequently permitted to contract between the widthwise adjacent bonds through which it extends such that its tension between those widthwise adjacent bonds is substantially relieved. The entrapment bonding operation is therefore said to be intermittent in the sense that at least one of the elastic strands 120, 124, 128, 132 is not permanently held in tension between all pairs of widthwise adjacent bonds through which it extends.

In one embodiment of an intermittent entrapment configuration of the anvil face 226, the anvil face 226 may be provided with a plurality of distinct circumferential regions 288 such that a dimension of a notch 286 (and, therefore, the lands 284 that flank it) on a ridge 280 in at least one circumferential region 288 is different than a dimension of a widthwise aligned notch 286 (and, therefore, the lands 284 that flank it) on a ridge 280 in at least one other circumferential region 288.

Figure 10:
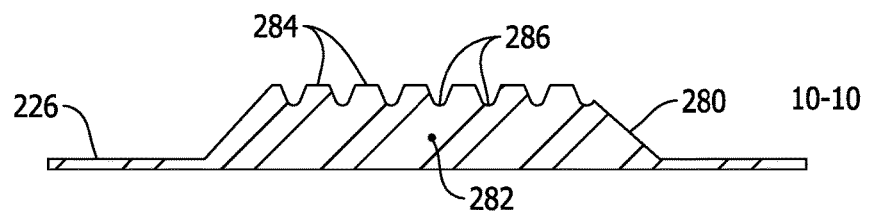
FIG. 10 is a cross-section, taken along plane 10-10 of FIG. 8, of another embodiment of a ridge defined by the anvil face of FIG. 8.

For example, each ridge 280 in a plurality of first circumferential regions 290, 296 may have at least one notch 286 that is sized differently as compared to at least one notch 286 that is widthwise aligned therewith on ridges 280 in a plurality of second circumferential regions 292, 294 interspaced between the first circumferential regions 290, 296. In this example, within the first circumferential regions 290, 296, the notches 286 may be sized with larger widths (like in FIG. 9) such that the elastic strands 120, 124, 128, 132 do not later become entrapped across (i.e., are later permitted to slip between) the widthwise adjacent bonds created at widthwise adjacent lands 284 on ridges 280 in these first circumferential regions 290, 296. Whereas, within the second circumferential regions 292, 294, the notches 286 may be sized with smaller widths (like in FIG. 10) such that the elastic strands 120, 124, 128, 132 later become entrapped across (i.e., are not later permitted to slip between) the widthwise adjacent bonds created at widthwise adjacent lands 284 on ridges 280 in the second circumferential regions 292, 294.

More specifically, in this example, at least one ridge 280 in each second circumferential region 292, 294 may have its notches 286 sized in the manner set forth above for the continuous entrapment example, while at least one ridge 280 in each first circumferential region 290, 296 may have its notches 286 sized with a width (as measured at the peaks of its flanking lands 284) of between about 0.010 inch and about 0.25 inch (e.g., between about 0.030 inch and about 0.060 inch in some embodiments; or about 0.035 inch in one particular embodiment). Thus, adequate slippage of the elastic strands 120, 124, 128, 132 across at least one ridge 280 in each first circumferential region 290, 296 is facilitated, especially when the elastic strands 120, 124, 128, 132 have a decitex of between about 300 and about 1240, and when the nonwoven fabrics 112, 116 have a grammage (gsm) of between about 8 and about 30.

Figure 11:
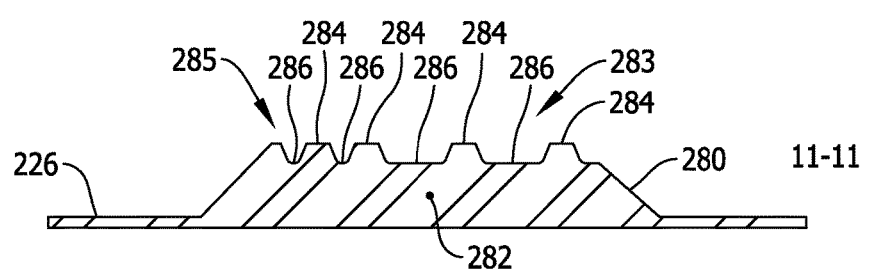
FIG. 11 is a cross-section, taken along plane 11-11 of FIG. 8, of yet another embodiment of a ridge defined by the anvil face of FIG. 8.

In both a continuous entrapment configuration and an intermittent entrapment configuration, the anvil face 226 may have a plurality of distinct widthwise segments 281, wherein each widthwise segment 281 has lands 284 and/or notches 286 of comparatively different sizes. For example, in one particular embodiment illustrated by FIG. 11, the anvil face 226 may have a first widthwise segment 283 with lands 284 that define notches 286 of a first width to suit elastic strands 120, 124, 128, 132 of a first decitex, and a second widthwise segment 285 with lands 284 that define notches 286 of a second width that is less than the first width to suit elastic strands 120, 124, 128, 132 of a second decitex that is less than the first decitex. Thus, each widthwise segment 281, no matter whether it is configured for continuous or intermittent entrapment, may be sized to accommodate elastic strands 120, 124, 128, 132 of different sizes.

Figure 12:
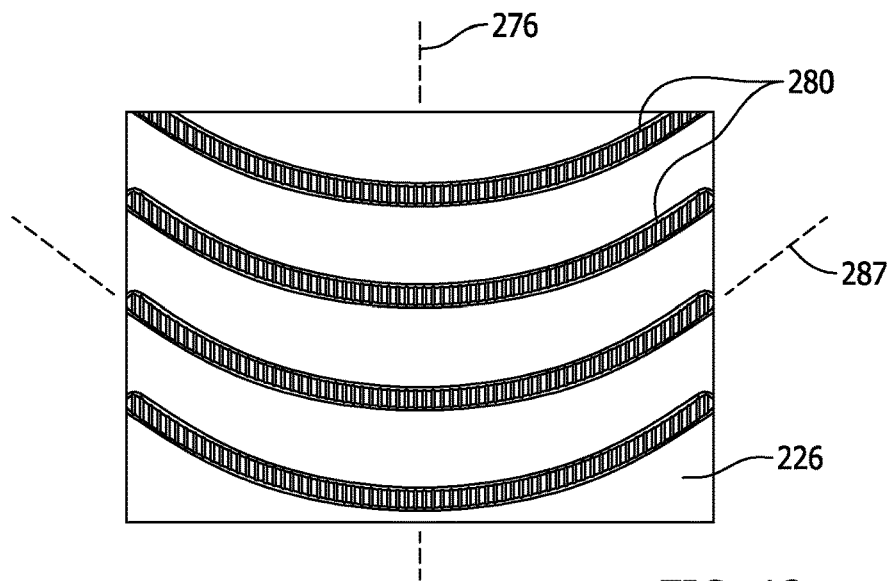
FIG. 12 is a laid-flat illustration of a portion of an annular face of another embodiment of an anvil for use in the apparatuses of FIGS. 2-7.
Figure 13:
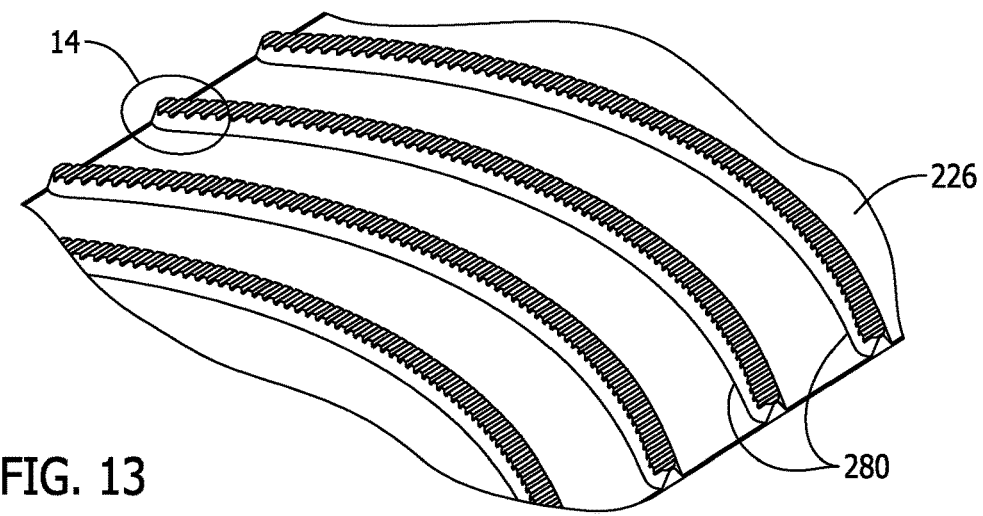
FIG. 13 is a perspective view of the portion of the annular face of FIG. 12.
Figure 14:
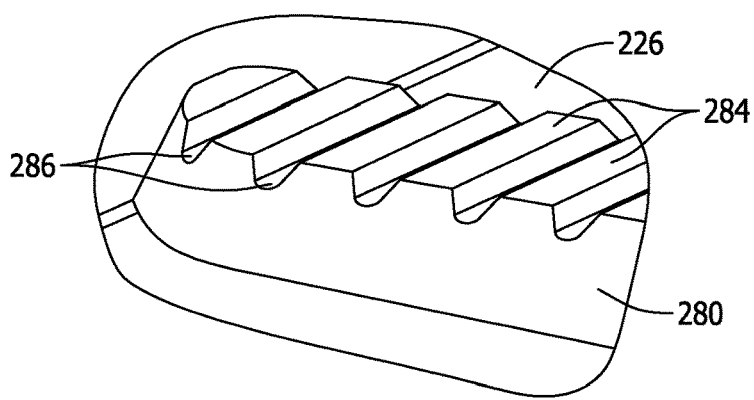
FIG. 14 is an enlarged segment of the perspective view of FIG. 13 taken within area 14 of FIG. 13.

In yet other embodiments, the anvil face 226 may have ridges 280 that extend non-linearly across the circumferential axis 276. For example, in one particular embodiment illustrated by FIGS. 12-14, the anvil face 226 may define a plurality of ridges 280 each with a curvilinear axis (e.g., a substantially arcuate axis 287). Notably, these embodiments with non-linear ridges 280 may have the same dimensions for the lands 284 and the notches 286 as for the substantially linearly extending ridges 280 set forth above, including the same dimensional variations amongst circumferential and widthwise regions 288, 281 as is set forth above with respect to the substantially linearly extending ridges 280.

Figure 15:
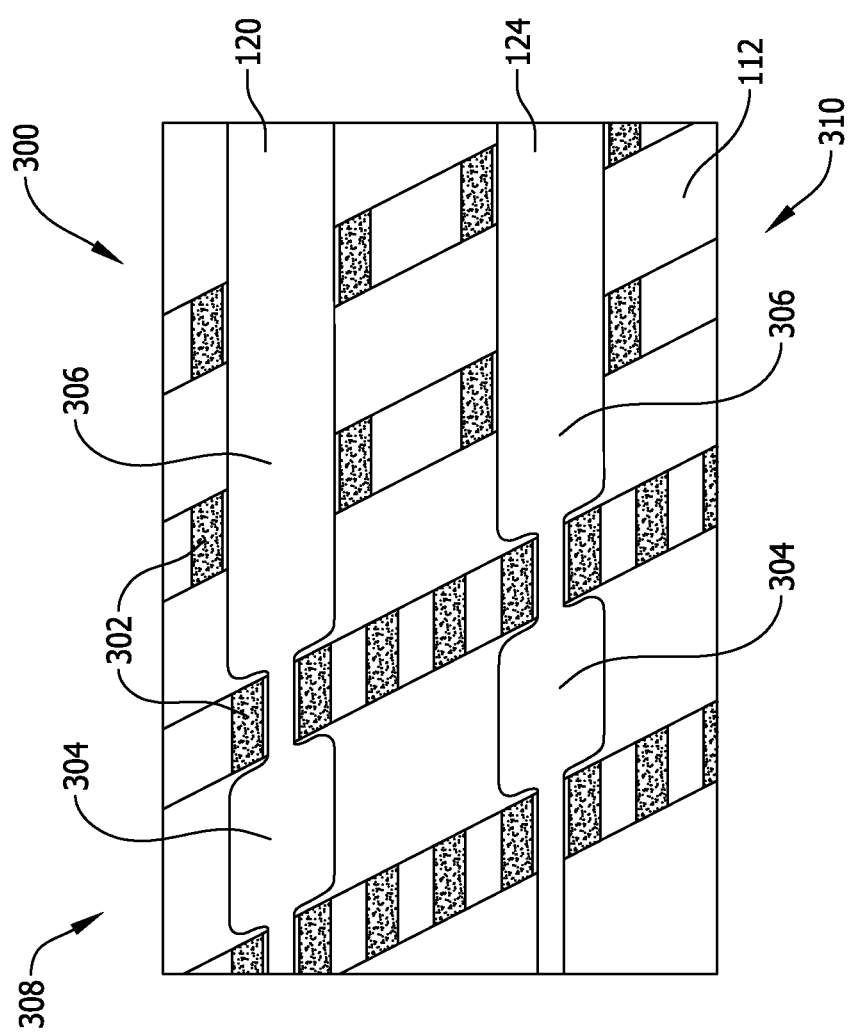
FIG. 15 is a schematic illustration of an elastic nonwoven material fabricated using an embodiment of the system of FIG. 1.

FIG. 15 illustrates an elastic nonwoven material 300 fabricated using the system 100. In the illustrated embodiment, an intermittent entrapment bonding process was performed on the nonwoven fabrics 112, 116 (with elastic strands 120, 124 sandwiched therebetween) using one of the embodiments of the apparatus 200 set forth above. The embodiment of the anvil 220 utilized to fabricate the material 300 has an anvil face 226 with notches 286 that vary in size across circumferential regions 288 as set forth in some of the embodiments above. In this manner, with the nonwoven fabrics 112, 116 and the elastic strands 120, 124 held in tension across the apparatus 200, the horn face 216 and the anvil face 226 created bonds 302 at locations corresponding to the lands 284 of the anvil face 226.

Once the bonded nonwoven fabrics 112, 116 (and the elastic strands 120, 124 sandwiched therebetween) were subsequently removed from the system 100, the tension in the elastic strands 120, 124 was partly relieved such that segments of each elastic strand 120, 124 were permitted to contract to create material 300. More specifically, a first segment 304 of each elastic strand 120, 124 became entrapped between adjacent rows of bonds 302 that corresponded to the ridges 280 which defined notches 286 of smaller widths. Whereas, a second segment 306 of each elastic strand 120, 124 was permitted to slip across widthwise adjacent bonds 302 in rows that corresponded to the ridges 280 which defined notches 286 of larger widths. In this manner, the nonwoven fabrics 112, 116 were caused to gather in areas 308 of the material 300 that have widthwise adjacent bonds 302 of closer spacing (but not in areas 310 that have widthwise adjacent bonds 302 of greater spacing) to effectively provide the material 300 with an elastic property. Notably, if a continuous entrapment operation had been utilized instead of an intermittent entrapment operation, the material 300 would not have second segments 306 that are permitted to slip, but would instead only have first segments 304 such that the nonwoven fabrics 112, 116 would gather along the entire material 300.

FIGS. 16-24 are laid-flat illustrations of portions of annular faces 226 of embodiments of anvils 220 for use in the apparatuses 200 shown in FIGS. 2-7. The anvil faces 226 shown in FIGS. 16-24 include ridges 280 arranged in patterns that enable the anvil 220 and the horn 208 to provide continuous running contact during operation of the apparatus 200. As used herein, the term "continuous running contact" means that the annular face 226 of the anvil 220 is configured to receive forces from the horn 208 substantially continuously throughout operation of the apparatus 200. In the example embodiments, continuous running contact allows the anvil 220 and the horn 208 to experience substantially uniform forces throughout operation. Thus, the energy required to operate the apparatus 200 is reduced. In addition, wear of the horn 208 and the anvil 220 is reduced in comparison to known systems. Moreover, vibration and/or noise associated with operation of the apparatus 200 can be reduced.

Embodiments of the of the annular faces 226 may allow for increased spacing between attachment points in the elastic nonwoven material and allow more independent movement of individual elastic strands 120, 124, 128, 132 relative to the elastic nonwoven fabric. Accordingly, the elastic strands 120, 124, 128, 132 may have increased elastic characteristics and function similar to an unattached elastic strand. For example, the annular faces 226 may allow for attachment points to be spaced apart by a distance up to about 150 mm or in a range of about 100 mm to about 150 mm. In alternative embodiments, the elastic strands 120, 124, 128, 132 may have any attachment points that allow the elastic strands to function as described herein. In some embodiments, bond points may be used between attachment points to orient the elastic strands 120, 124, 128, 132 without attaching the strands. In addition, the bond points may be used to provide continuous running contact.

Figure 16:
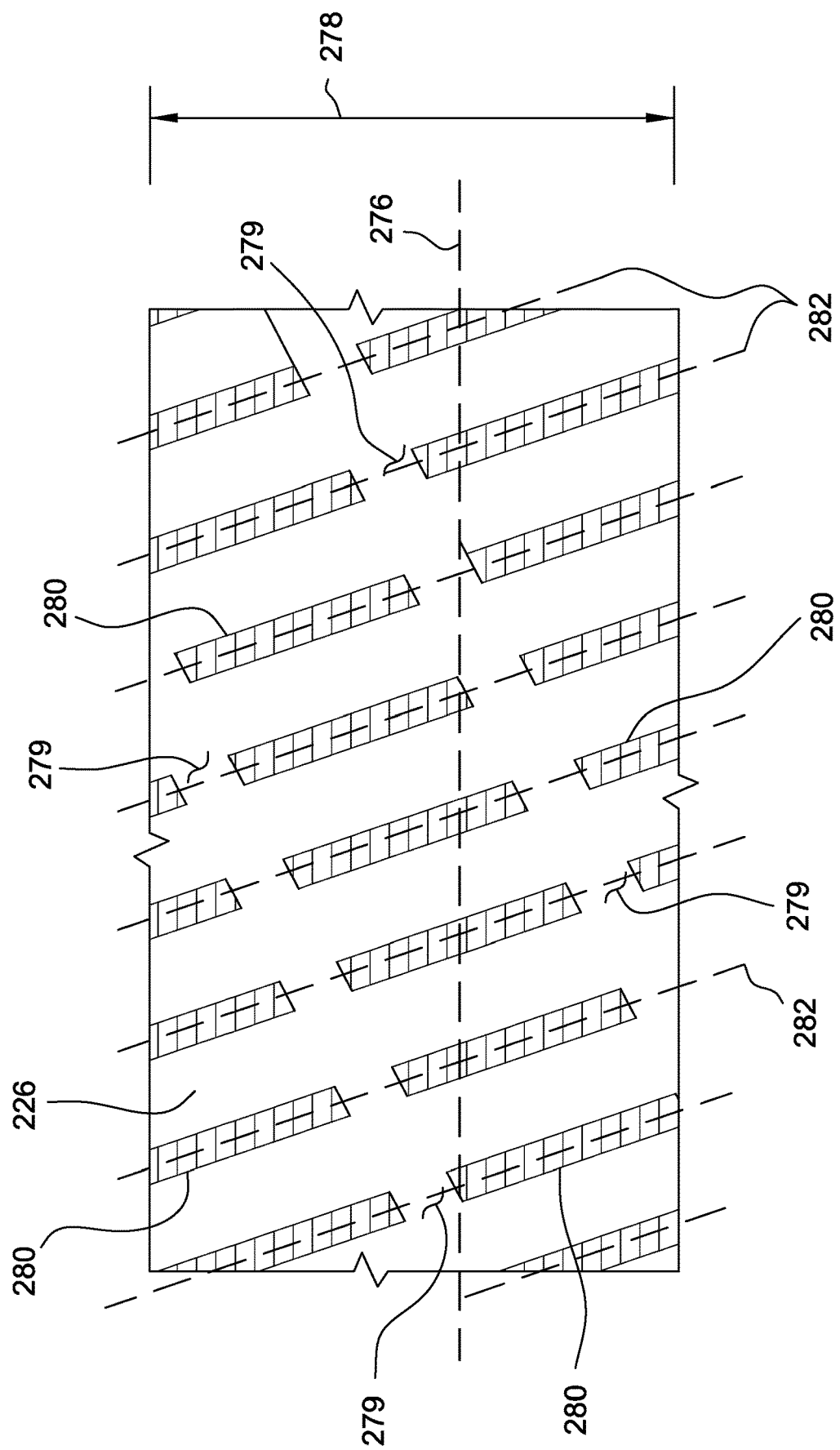
FIG. 16 is a laid-flat illustration of a portion of an annular face of yet another embodiment of an anvil for use in the apparatuses of FIGS. 2-7, the annular face including discontinuous ridges.

FIG. 16 is a laid-flat illustration of an embodiment of the anvil face 226 including ridges 280 and gaps 279. In the illustrated embodiment, each ridge 280 extends substantially linearly across the circumferential axis 276 and spans a portion of the width dimension 278 of the anvil face 226. In addition, the ridges 280 are discontinuous such that gaps 279 are defined between adjacent ridges 280. The gaps 279 extend substantially linearly across the circumferential axis 276 between adjacent ridges 280 and span a portion of the width dimension 278 of the anvil face 226. Accordingly, the gaps 279 reduce the amount of surface area of the anvil face 226 that receives forces from the horn 208 (shown in FIGS. 2-7). As a result, during operation of the apparatus 200, the force required to form bonds in the nonwoven fabric is reduced. In addition, the elastic strands 120, 124, 128, 132 (shown in FIG. 1) may move more independently relative to each other than if the strands were uniformly attached in the width dimension 278.

Each ridge 280 has an extension axis 282 oriented oblique to the circumferential axis 276. In addition, the ridges 280 are positioned such that each ridge 280 overlaps adjacent ridges 280 along the circumferential axis 276. Accordingly, the ridges 280 are configured to provide continuous running contact between the horn 208 (shown in FIGS. 2-7) and the anvil 220 (shown in FIGS. 2-7) during operation of the apparatus 200 (shown in FIGS. 2-7). Moreover, the oblique extension axes 282 allow for increased spacing between the ridges 280. Also, the portion of anvil 220 that receives forces from the horn 208 may be decreased because the ridges 280 provide continuous running contact without requiring additional contact points.

In addition, in the illustrated embodiment, the ridges 280 are aligned and an alternating pattern of ridges 280 and gaps 279 extends along each extension axis 282. In alternative embodiments, the ridges 280 are arranged in any pattern that enables the anvil face 226 to function as described herein. For example, in some embodiments, at least some adjacent ridges 280 may be positioned at angles relative to each other.

In some embodiments, each ridge 280 may extend along the respective extension axis 282 a distance in a range of about 1.5 mm to about 10 mm. The gaps 279 may extend along the respective extension axis 282 a distance in range of about 0.5 mm to about 20 mm. In alternative embodiments, the ridges 280 and the gaps 279 may extend any distance that enables the anvil face 226 to function as described herein.

Figure 17:
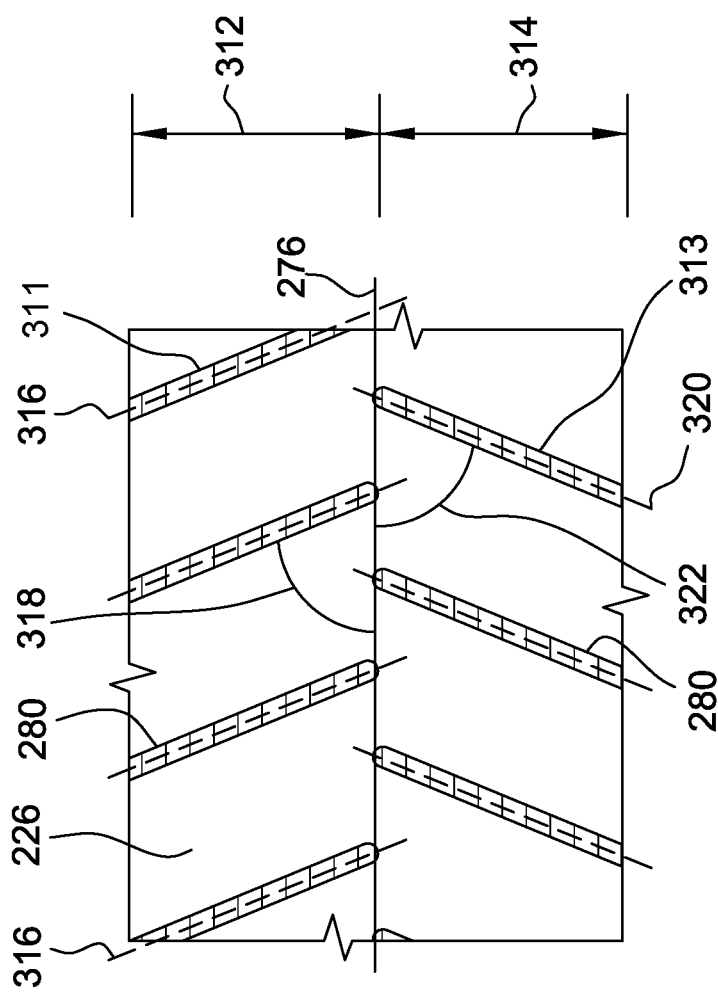
FIG. 17 is a laid-flat illustration of a portion of an annular face of yet another embodiment of an anvil for use in the apparatuses of FIGS. 2-7, the annular face including ridges extending along oblique axes.

FIG. 17 is a laid-flat illustration of another embodiment of the anvil face 226 of the apparatus 200 (shown in FIGS. 1-7). The anvil face 226 includes first ridges 311 in a first region 312 and second ridges 313 in a second region 314. In the first region 312, each ridge 311 extends along an extension axis 316. Each extension axis 316 is oriented oblique to the circumferential axis 276 such that the extension axis and the circumferential axis 276 define an angle 318. In the second region 314, each ridge 313 extends along an extension axis 320. Each extension axis 320 is oriented oblique to the circumferential axis 276 such that the circumferential axis 276 and extension axis define an angle 322. The extension axes 320 are oriented oblique to the extension axes 316. In addition, the ridges 311 in the first region 312 are offset from the ridges 313 in the second region 314. As a result, the spacing between the ridges 311, 313 may be increased and the ridges 311, 313 may be configured for continuous running contact.

Figure 18:
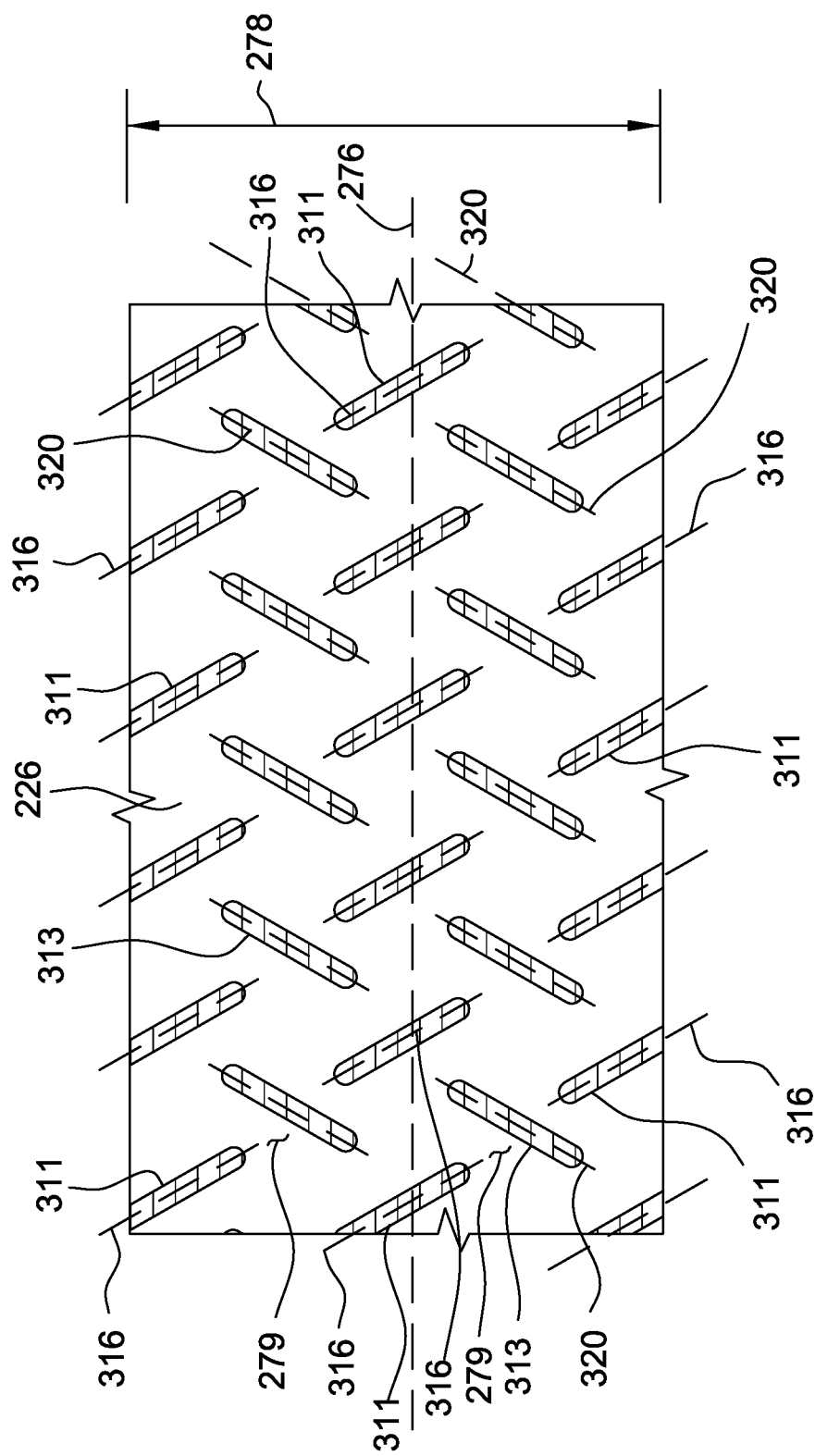
FIG. 18 is a laid-flat illustration of a portion of an annular face of yet another embodiment of an anvil for use in the apparatuses of FIGS. 2-7, the annular face including a plurality of discrete ridges.

FIG. 18 is a laid-flat illustration of yet another embodiment of the anvil face 226 of the apparatus 200 (shown in FIGS. 1-7). The anvil face 226 includes first ridges 311 and second ridges 313. In the illustrated embodiment, each first ridge 311 has an extension axis 316 oriented oblique to the circumferential axis 276 and the width dimension 278. In addition, each first ridge 311 is spaced from adjacent first ridges in the width dimension 278 and along the circumferential axis 276. Each second ridge 313 has an extension axis 320 oriented oblique to the circumferential axis 276 and the width dimension 278. Also, each second ridge 313 is spaced from adjacent second ridges in the width dimension 278 and along the circumferential axis 276. Moreover, the first extension axes 316 are oriented oblique to the second extension axes 320. In alternative embodiments, the anvil face 226 may include any ridges 311, 313 that enable the anvil face to function as described herein.

The first ridges 311 and the second ridges 313 are intermixed throughout the anvil face 226. For example, the second ridges 313 extend through the gaps 279 defined between the first ridges 311. Also, the first ridges 311 extend through the gaps 279 defined between the second ridges 313. Accordingly, each first ridge 311 overlaps adjacent second ridges 313 along the circumferential axis 276 and the width dimension 278. Each second ridge 313 overlaps adjacent first ridges 311 along the circumferential axis 276 and the width dimension 278.

The ridges 311, 313 define a pattern on the anvil face 226. In some embodiments, the pattern of ridges 311, 313 is configured to provide desired characteristics of the nonwoven elastic material. For example, the pattern of overlapping ridges 311, 313 may be configured to provide ruffling having desired characteristics (size, spacing, tension, etc.). As a result, the ruffling may provide (1) aesthetic qualities (e.g., appearance, softness), and/or (2) functional properties (e.g., for a waistband, panel, leg cuff, etc.) in one or more zones of the elastic nonwoven material. In alternative embodiments, the first ridges 311 and the second ridges 313 may be positioned in any pattern that enables the anvil face 226 to function as described herein.

Also, in some embodiments, the first ridges 311 and/or the second ridges 313 may include at least one shape of the following shapes: circular, polygonal, rectangular, sinusoidal, and ovular. In further embodiments, the first ridges 311 and/or the second ridges 313 may be configured to define an image and/or alpha-numeric character in the elastic nonwoven material. In such embodiments, some of the first ridges 311 and/or the second ridges 313 may have a substantially continuous surface to facilitate forming the desired appearance of the elastic nonwoven material.

Figure 19:
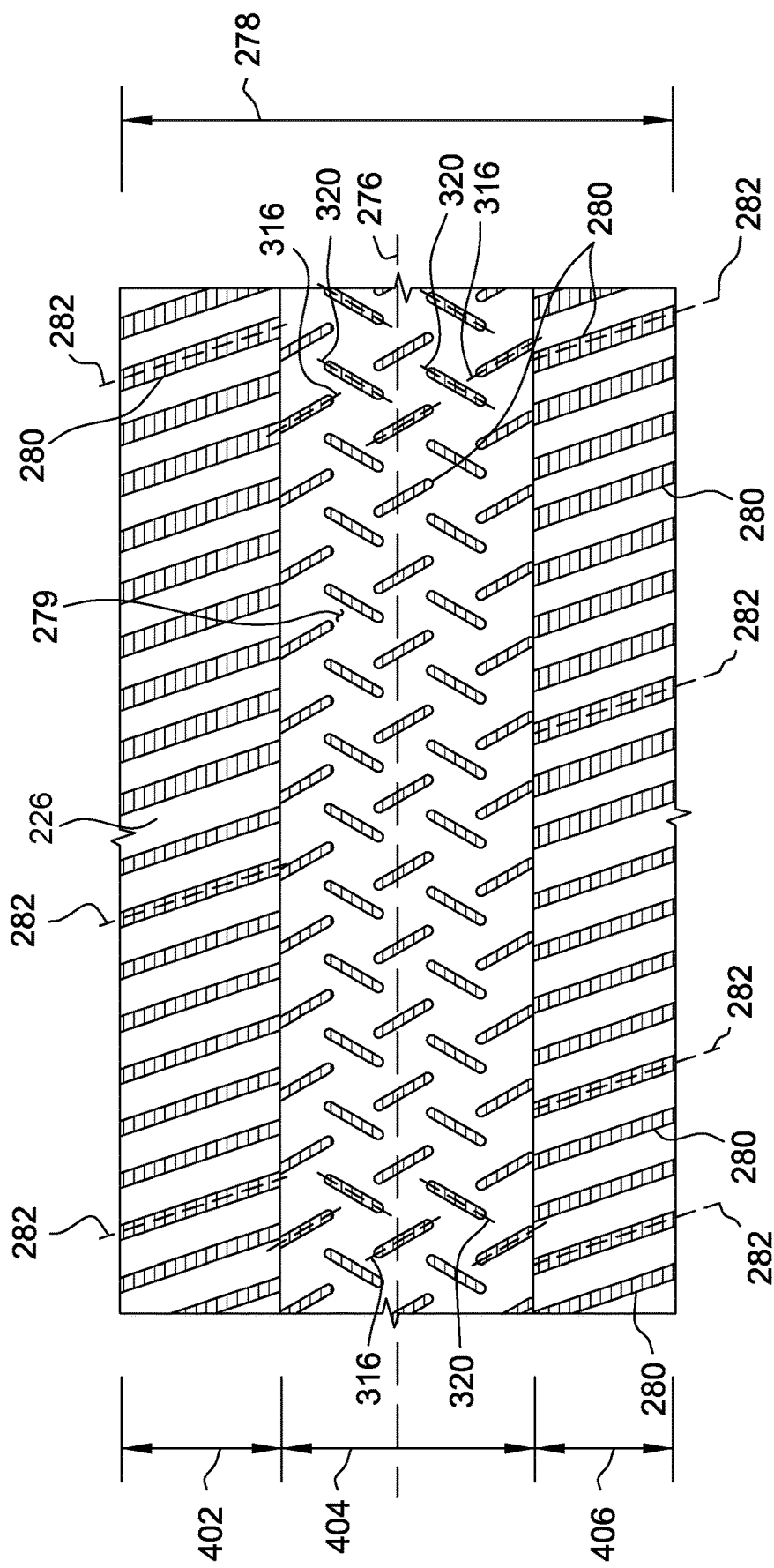
FIG. 19 is a laid-flat illustration of a portion of an annular face of yet another embodiment of an anvil for use in the apparatuses of FIGS. 2-7, the annular face including different patterns of ridges.

FIG. 19 is a laid-flat illustration of another embodiment of the anvil face 226 of the apparatus 200 (shown in FIGS. 1-7) including ridges 280 arranged in patterns. As shown in FIG. 19, the anvil face 226 includes a first region 402, a second region 404, and a third region 406. In the first region 402 and the third region 406, the ridges 280 are arranged in a first pattern in which each ridge 280 has an extension axis 282 oriented oblique to the circumferential axis 276 and the width dimension 278. In the second region 404, the ridges 280 are arranged in a second pattern in which each ridge 280 has an extension axis 316, 320 oriented oblique to the circumferential axis 276 and the width dimension 278. The extension axes 316 are oriented oblique to the extension axis 320. In addition, in the second region 404, the ridges 280 define gaps 279 therebetween and are intermixed such that adjacent ridges overlap along the circumferential axis 276 and in the width dimension. Accordingly, the first pattern and the second pattern increase the portion of the anvil face 226 that is utilized during operation of the apparatus 200.

Figure 20:
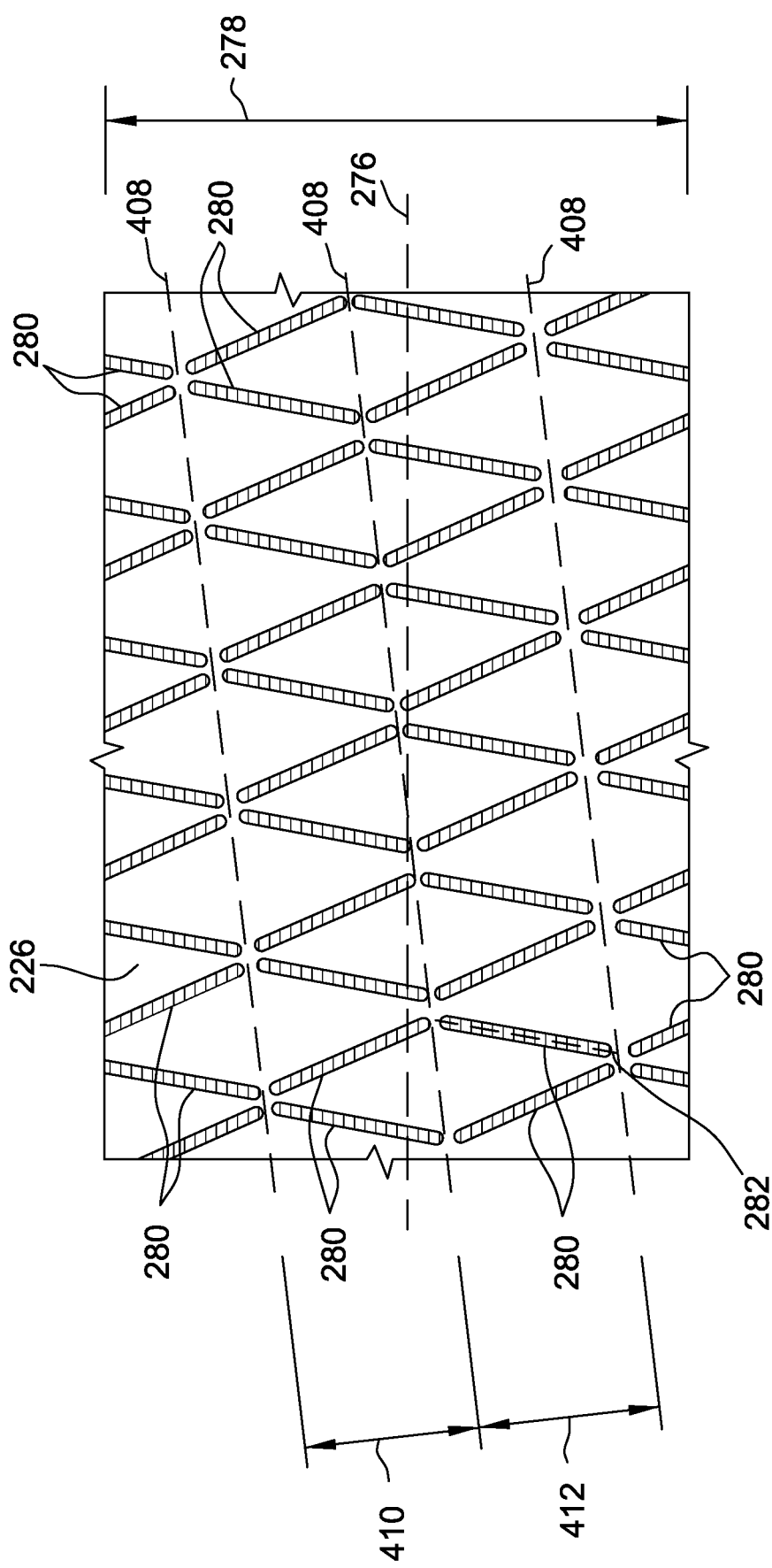
FIG. 20 is a laid-flat illustration of a portion of an annular face of yet another embodiment of an anvil for use in the apparatuses of FIGS. 2-7, the annular face including symmetric patterns of ridges.

FIG. 20 is a laid-flat illustration of another embodiment of the anvil face 226 of the apparatus 200 (shown in FIGS. 1-7) including a symmetric pattern of ridges 280. The anvil face 226 includes a first region 410 including ridges 280 and a second region 412 including ridges 280. In the first region 410, each ridge 280 has an extension axis 282 oriented oblique to the circumferential axis 276 and the width dimension 278. In the second region 412, each ridge 280 has an extension axis 282 oriented oblique to the circumferential axis 276 and the width dimension 278. An axis of symmetry 408 extends between the first region 410 and the second region 412. The ridges 280 in the first region 410 are symmetric to the ridges 280 in the second region 412 about the axis of symmetry 408. Moreover, the anvil face 226 includes a plurality of axes of symmetry 408 such that the ridges 280 form a repeating, symmetric pattern. In the illustrated embodiment, each axis of symmetry 408 is oblique to the circumferential axis 276. In alternative embodiments, the anvil face 226 may have any axis of symmetry 408 that enables the anvil face to function as described herein.

Figure 21:
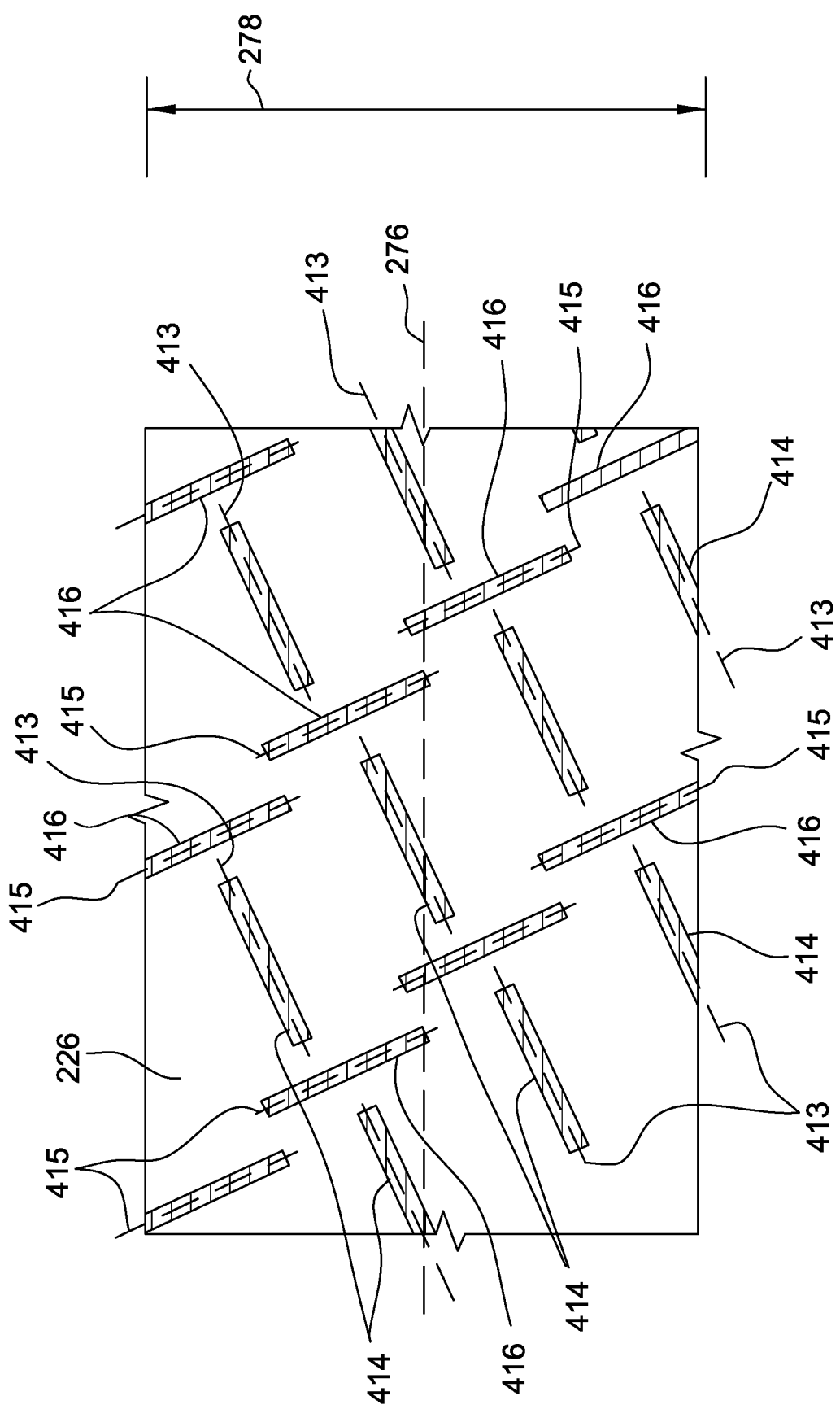
FIG. 21 is a laid-flat illustration of a portion of an annular face of yet another embodiment of an anvil for use in the apparatuses of FIGS. 2-7, the annular face including ridges that are oriented at substantially perpendicular angles to each other.

FIG. 21 is a laid-flat illustration of another embodiment of the anvil face 226 including ridges 414, 416 that are oriented at substantially perpendicular angles. The anvil face 226 includes first ridges 414 and second ridges 416. The first ridges 414 have extension axes 413 oriented oblique to the circumferential axis 276 and the width dimension 278. The second ridges 416 have extension axes 415 oriented oblique to the circumferential axis 276 and the width dimension 278. The extension axes 413 of the first ridges 414 are perpendicular to the extension axes 415 of the second ridges 416. Accordingly, the first ridges 414 and the second ridges 416 form patterns that (1) provide continuous running contact, (2) reduce the contact area of the horn 208 and the anvil 220, and (3) distribute loads throughout the anvil 220.

Figure 22:
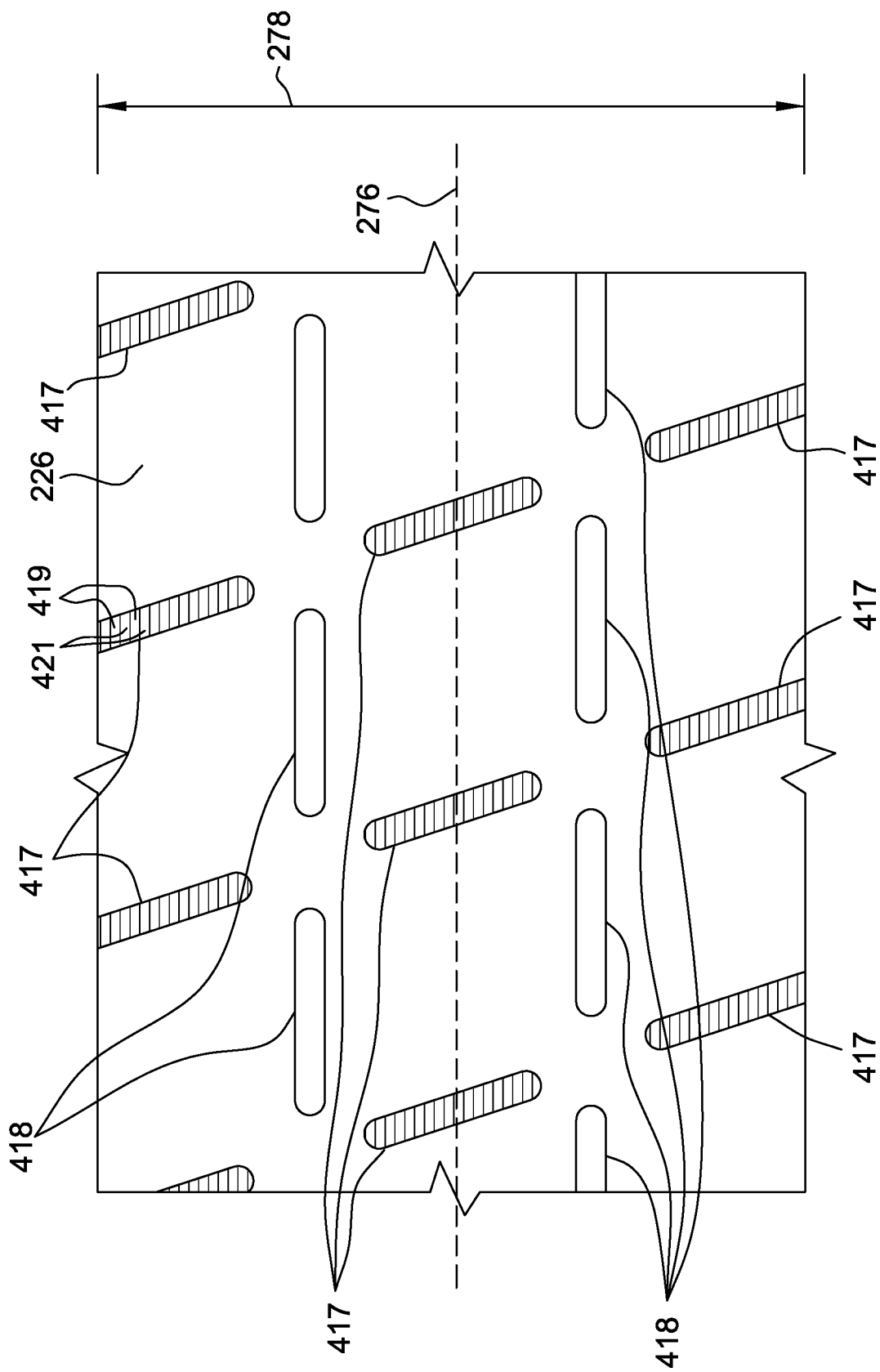
FIG. 22 is a laid-flat illustration of a portion of an annular face of yet another embodiment of an anvil for use in the apparatuses of FIGS. 2-7, the annular face including ridges.

FIG. 22 is a laid-flat illustration of another embodiment of the anvil face 226 of the apparatus 200 including first ridges 417 and second ridges 418. Each first ridge 417 may include a plurality of lands 419 and notches 421. Each second ridge 418 has a substantially continuous contour and provides a bond point in the nonwoven fabric. The first ridges 417 and the second ridges 418 are intermixed throughout the anvil face 226. Specifically, each first ridge 417 extends between adjacent second ridges 418 and each second ridge 418 extends between adjacent first ridges 417. The second ridges 418 allow for increased spacing between the first ridges 417 and provide increased bonding in the elastic nonwoven material and/or continuous running contact.

The first ridges 417 and the second ridges 418 may have any suitable shapes. For example, the first ridges 417 and/or the second ridges 418 may include orthogonal lines, dots, ovals, polygons, polygonal lines, sinusoidal lines, text, and/or any other suitable shape. In the illustrated embodiment, the first ridges 417 and the second ridges 418 are rectangular.

In addition, the first ridges 417 extend oblique to the circumferential axis 276 and the width dimension 278. The second ridges 418 extend parallel to the circumferential axis 276. Accordingly, the first ridges 417 are oblique to the second ridges 418. In alternative embodiments, the first ridges 417 and the second ridges 418 may extend in any direction that enables the apparatus 200 to operate as described herein. For example, in some embodiments, at least some of the second ridges 418 may extend oblique to the circumferential axis 276 and/or the width dimension 278.

Figure 23:
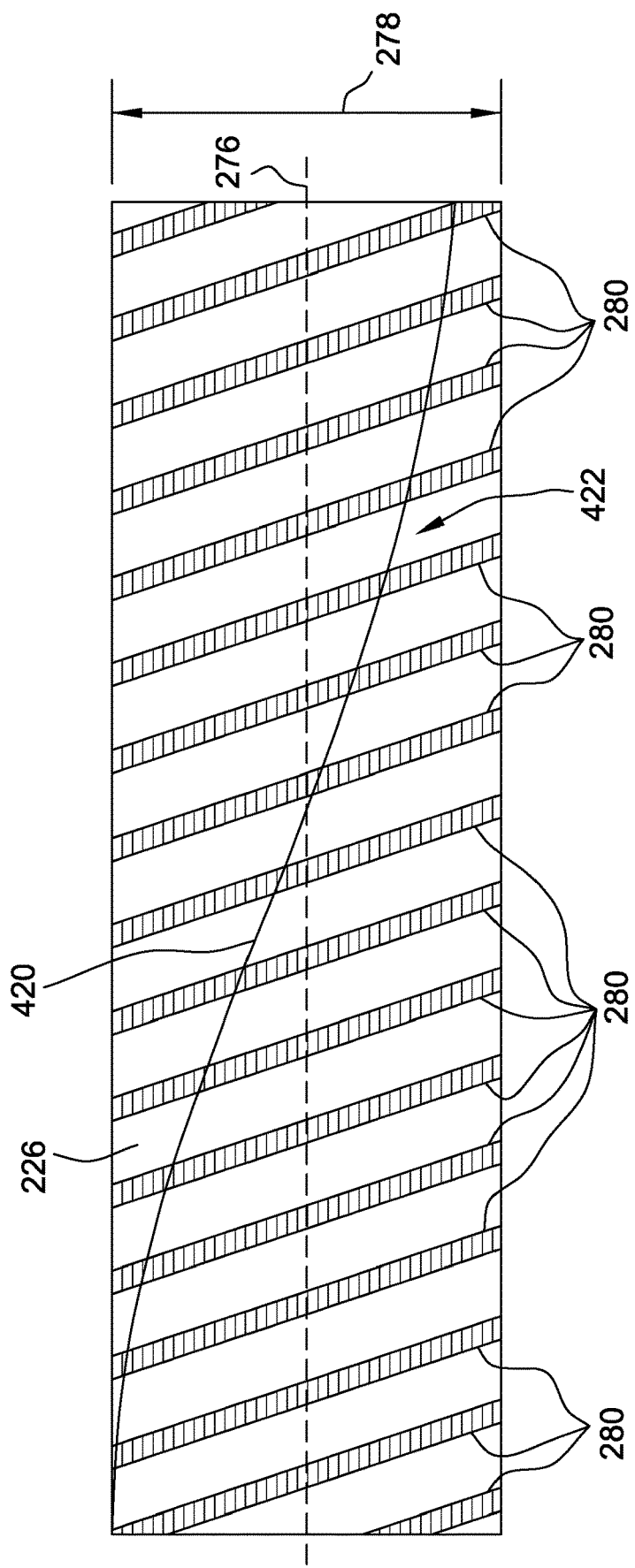
FIG. 23 is a laid-flat illustration of a portion of an annular face of yet another embodiment of an anvil for use in the apparatuses of FIGS. 2-7, and an elastic strand extending across the width of the anvil face along a curve.

FIG. 23 is a laid-flat illustration of another embodiment of the anvil face 226 of the apparatus 200. An elastic strand 420 extends across the width dimension 278 of the anvil face 226 along a curve 422 relative to the circumferential axis 276. The elastic strand 420 may be directed along the curve 422 by the supply station 102 (shown in FIG. 1). For example, with reference to FIGS. 1, 2, and 23, the supply station 102 may be configured to reciprocate and dispense the elastic strand 420 as the anvil 220 rotates such that the elastic strand 420 is received by ridges 280 on the anvil face. Due to the reciprocating motion, the elastic strand 420 may be received by varying portions of the ridges 280 such that the elastic strand 420 is directed along the curve 422. In alternative embodiments, the elastic strand 420 may be directed in any manner that enables the elastic nonwoven material to function as described herein.

Figure 24:
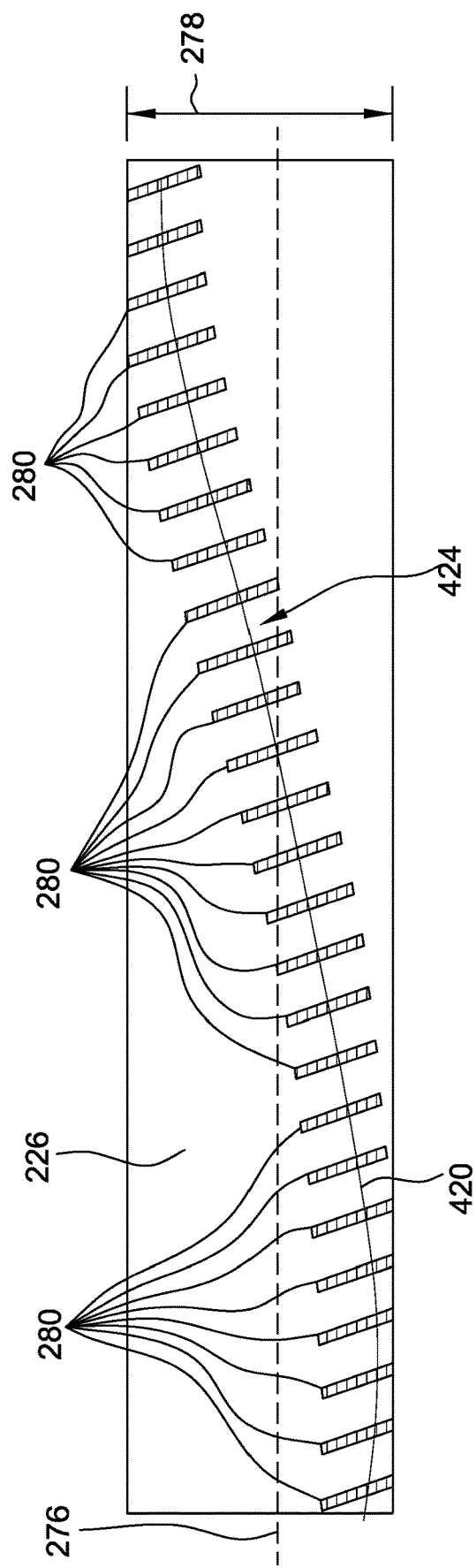
FIG. 24 is a laid-flat illustration of a portion of an annular face of yet another embodiment of an anvil for use in the apparatuses of FIGS. 2-7, and an elastic strand received and directed along a curve by ridges of the annular face.

FIG. 24 is a laid-flat illustration of another embodiment of the anvil face 226 of the apparatus 200. The anvil face 226 includes ridges 280 that extend across a portion of the width dimension 278 of the anvil face 226. The position of the ridges 280 corresponds to a curve 424 relative to the circumferential axis 276. The ridges 280 are configured to direct an elastic strand 420 along the curve 424 across the width of the anvil face 226 as the anvil 220 (shown in FIG. 2) rotates. In alternative embodiments, the elastic strand 420 may be directed in any manner that enables the elastic nonwoven material to function as described herein.

In some embodiments, the elastic strand 420 may be at least partially directed by the supply station 102 (shown in FIG. 1). For example, the ridges 280 may be configured to receive the elastic strand 420 and direct the elastic strand along a curve 424 corresponding to the reciprocating motion. In other embodiments, the supply station 102 may dispense the elastic strand 420 from a stationary position and the elastic strand may be directed along the curve 424 by any suitable means.

The elastic strand 420 may be directed along the curve 424 during a continuous entrapment process and/or an intermittent entrapment process. In addition, the elastic strand 420 may be directed along the curve 424 in a portion of the elastic nonwoven material and not necessarily throughout the entirety of the material.

Figure 25:
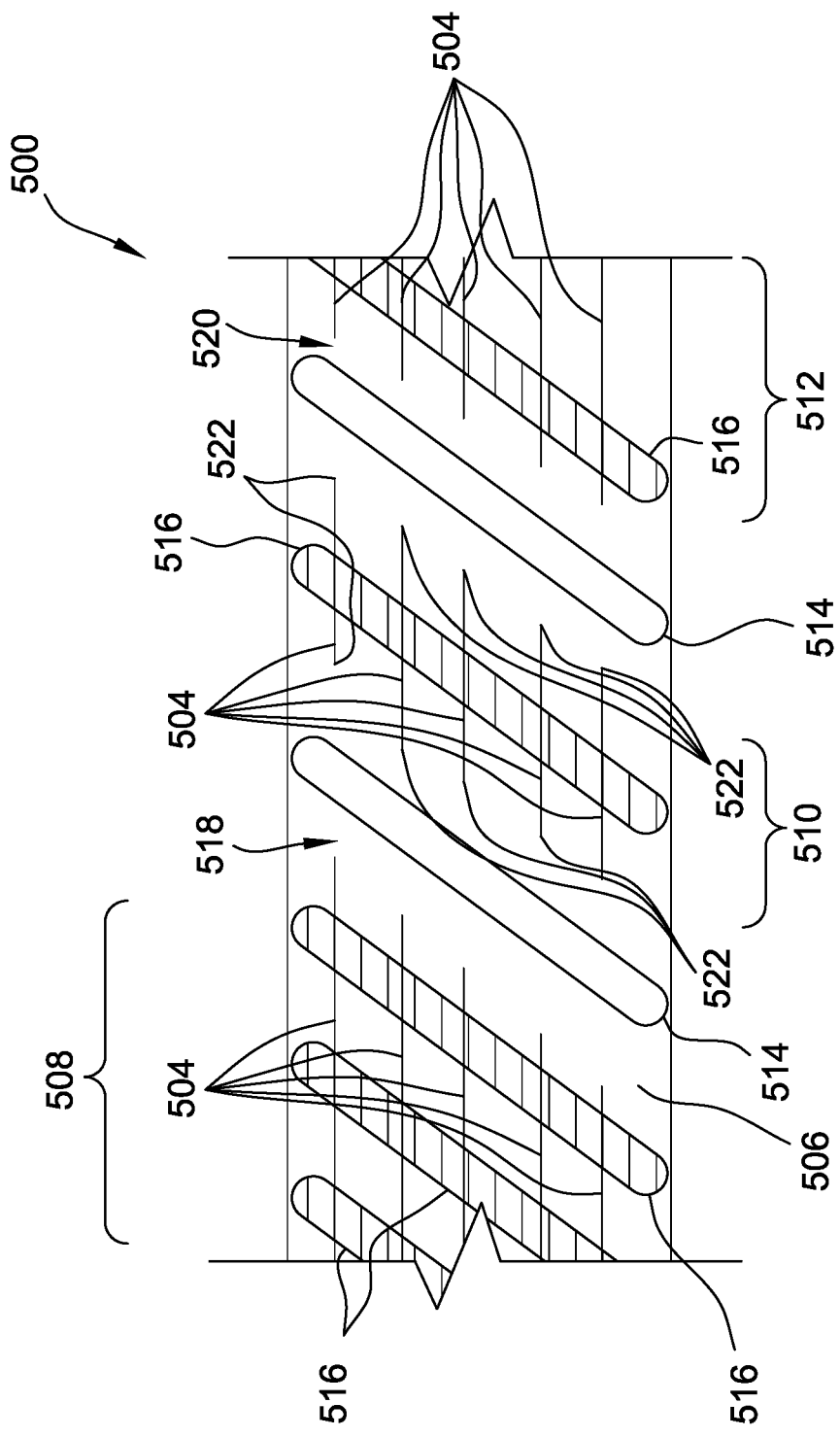
FIG. 25 is a schematic illustration of an elastic nonwoven material fabricated using an embodiment of the system of FIG. 1 and an intermittent entrapment process.

FIG. 25 is a schematic illustration of an elastic nonwoven material 500 fabricated using the system 100 and an intermittent elastic entrapment process. The elastic nonwoven material 500 includes at least one elastic strand 504 and a nonwoven fabric 506. The elastic nonwoven material 500 further includes a first region 508, a second region 510, and a third region 512. The elastic strand 504 is retained on the nonwoven fabric 506 in at least the first region 508 and the third region 512. For example, the elastic strand 504 may be entrapped within the nonwoven fabric 506 using the systems and methods described herein.

In the illustrated embodiment, the elastic strands 504 may be severed or cut by a cutting apparatus 514 between the first region 508 and the second region 510 and between the second region 510 and the third region 512. As a result, the elastic strands 504 are at least partially free in the second region 510. In some embodiments, the elastic strands 504 may be cut along a line substantially perpendicular to a longitudinal direction of the elastic nonwoven material 500. In other embodiments, the elastic strands 504 may be cut along a line extending at least partially at an oblique angle and/or parallel to the longitudinal direction. In further embodiments, the elastic strands 504 may be cut along a curve. In alternative embodiments, the elastic strands 504 may be severed in any manner that enables the elastic nonwoven material 500 to function as described herein.

The elastic nonwoven material 500 may have different elastic properties and appearances in the regions 508, 510, 512. For example, in the first region 508 and the third region 512, the elastic strands 504 are under tension and may cause the nonwoven fabric 506 to gather. In the second region 510, the elastic strands 504 are relaxed and the nonwoven fabric 506 is not caused to gather by the elastic strands.

The nonwoven fabric 506 includes at least one bond 516 in the second region 510 that is configured to retain the elastic strands 504 on the nonwoven fabric when the elastic strands are severed by the cutting apparatus 514. Specifically, the nonwoven fabric 506 is bonded between a first cut 518 and a second cut 520 such that free ends 522 of the elastic strands 504 extend on either side of the bond 516. Moreover, the bond 516 prevents free elastic strands 504 from being disbursed as debris and causing damage to or cluttering the elastic nonwoven material 500 and the apparatus 200 (shown in FIG. 1). As a result, the bond 516 reduces the cost to assemble the elastic nonwoven material 500.

Figure 26:
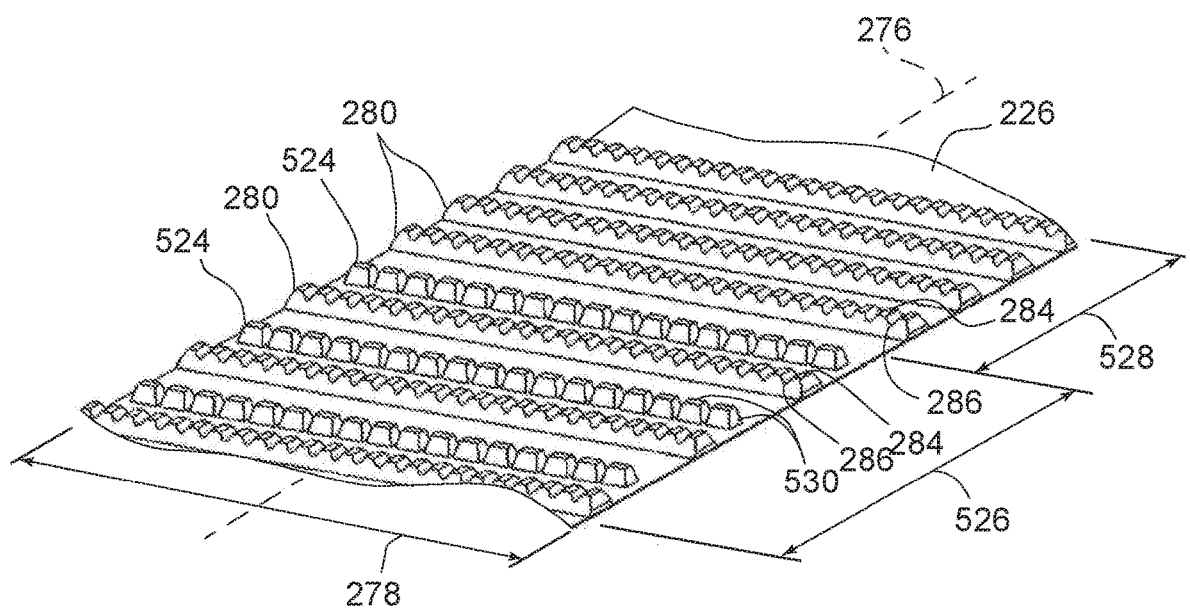
FIG. 26 is a laid-flat perspective view of an annular face of yet another embodiment of an anvil for use in the apparatuses of FIGS. 2-7.

FIG. 26 is a laid-flat perspective view of an annular face of yet another embodiment of an anvil for use in the apparatuses of FIGS. 2-7. In the illustrated embodiment, the anvil face 226 has a plurality of ridges formed thereon, including ridges 280 (i.e., first ridges) and cutting and bonding ridges 524 (i.e., second ridges). The ridges 280 and 524 extend linearly and/or obliquely across the circumferential axis 276, extend across substantially the entire width dimension 278 of the anvil face 226, and adjacent ridges 280 and 524 are substantially equally spaced apart from one another along the circumferential axis 276. The ridges 280 and 524 may also extend non-linearly across the circumferential axis 276, and may be spaced from one another by any suitable regular or irregular distance along the circumferential axis 276.

In one suitable embodiment, at least one ridge 280 is positioned between a pair of ridges 524 along the circumferential axis 276. For example, the ridges 280 and 524 are arranged on the anvil face 226 to define a first region 526 and a second region 528 along the circumferential axis 276. The first region 526 includes the at least one ridge 280 positioned between the pair of ridges 524 and, more specifically, includes a plurality of ridges 280 and a plurality of ridges 524 alternatingly arranged along the circumferential axis 276. The second region 528 includes a plurality of ridges 280 arranged sequentially along the circumferential axis 276.

Each ridge 524 includes a plurality of bonding and cutting members 530 arranged to extend along the width dimension 278 of the anvil face 226. As will be described in more detail below, the bonding and cutting members 530 of the ridges 524 are configured to perform a bonding and cutting operation on elastic nonwoven material, such as the elastic nonwoven material 500 (shown in FIG. 25). During a bonding operation, the elastic strands 504 are directed along notches 286 of adjacent ridges 280, and retained on the nonwoven fabric 506 with bonds 516 (shown in FIG. 25). In addition, the elastic strands 504 are severed by the bonding and cutting members 530 such that the free ends 522 of the elastic strands 504 extend on either side of the bonds 516. As such, in one suitable embodiment, at least one bonding and cutting member 530 is aligned along the circumferential axis with adjacent notches 286 of the adjacent ridges 280.

Figure 27:
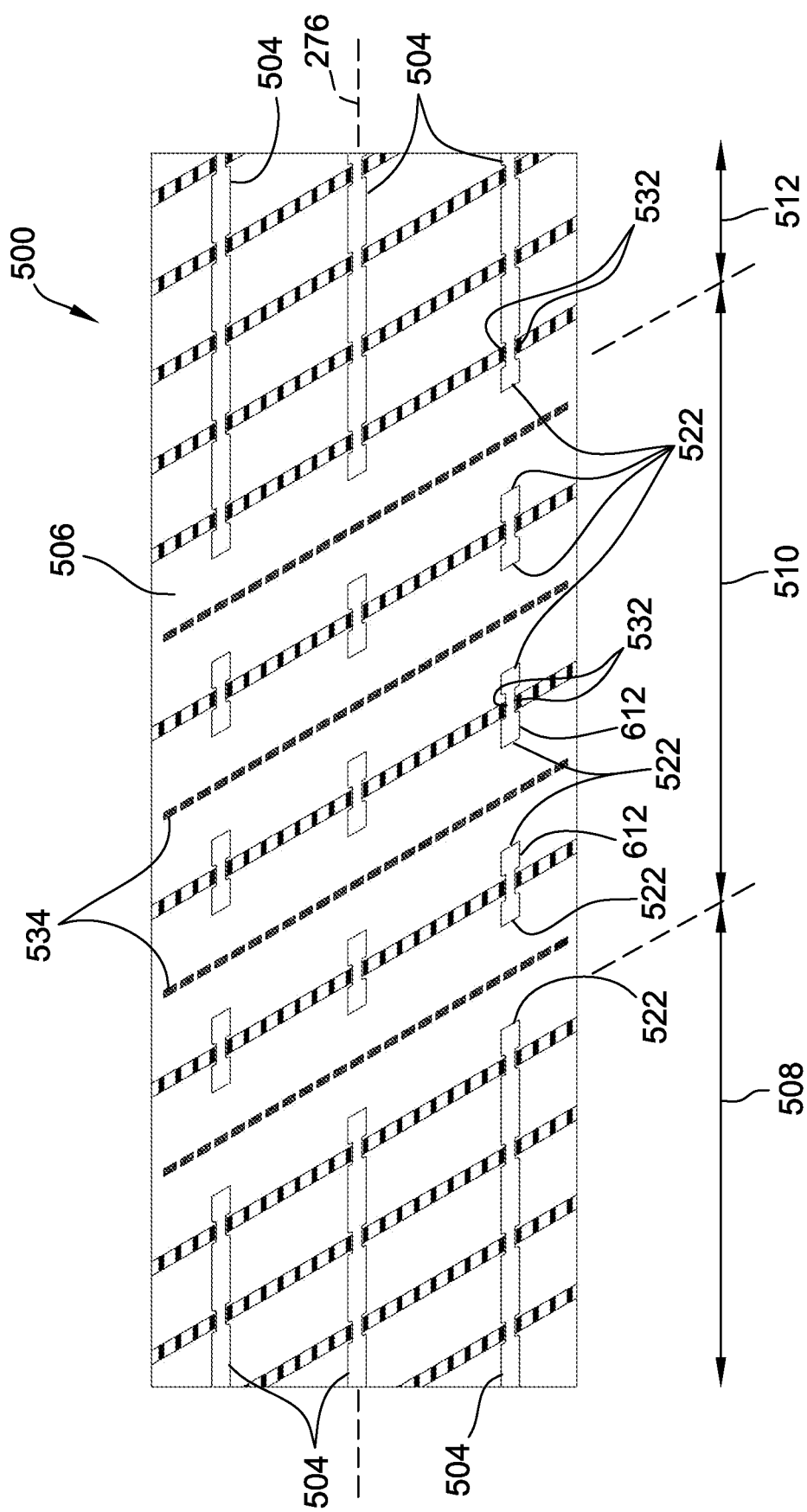
FIG. 27 is a schematic illustration of an elastic nonwoven material fabricated using an embodiment of the system of FIG. 26.
Figure 28:
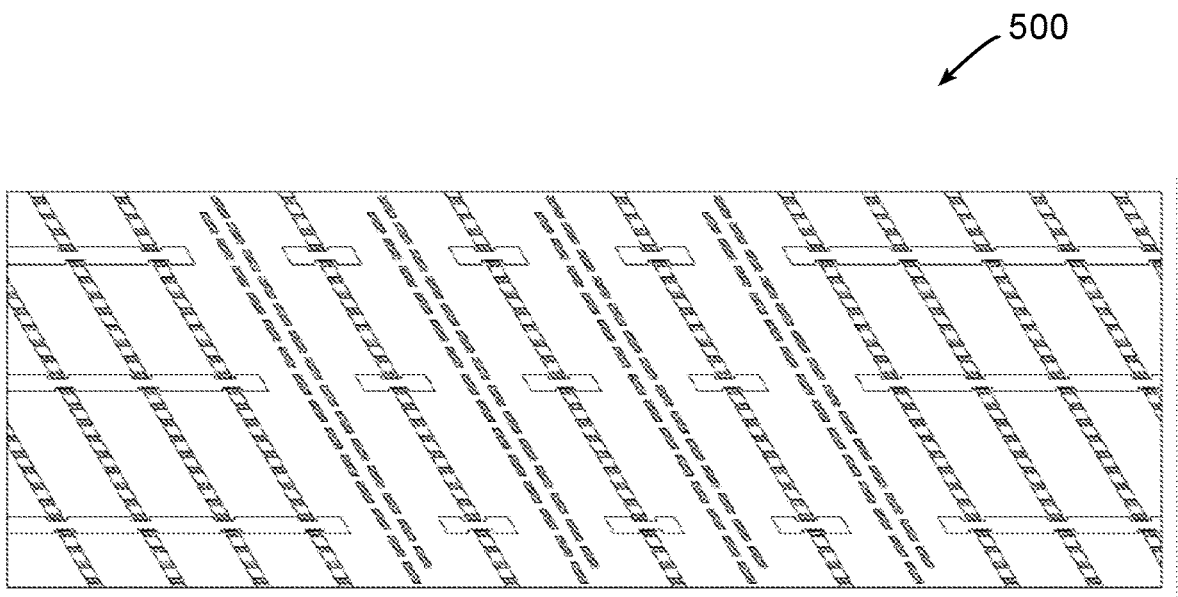
FIG. 28 is a schematic illustration of an elastic nonwoven material fabricated using another embodiment of the system of FIG. 26.
Figure 29:
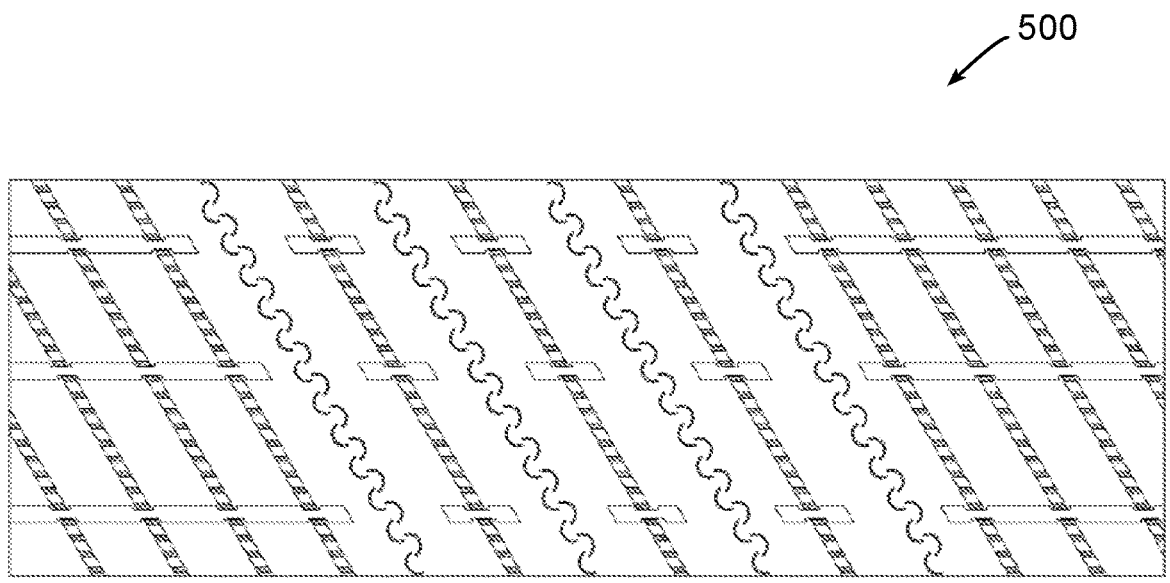
FIG. 29 is a schematic illustration of an elastic nonwoven material fabricated using another embodiment of the system of FIG. 26.
Figure 30:
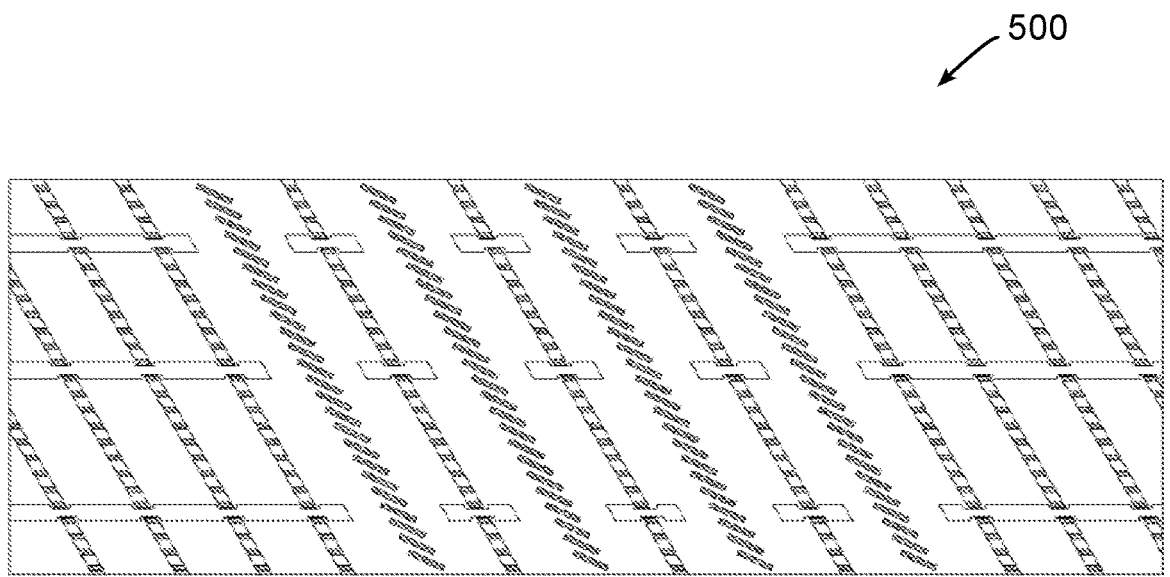
FIG. 30 is a schematic illustration of an elastic nonwoven material fabricated using another embodiment of the system of FIG. 26.
Figure 31:
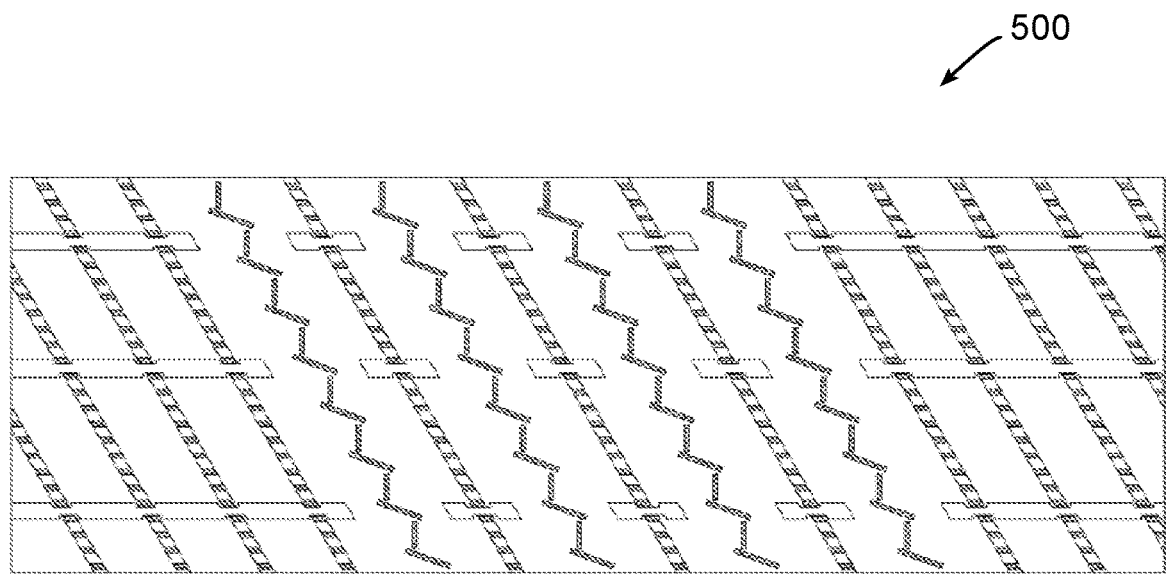
FIG. 31 is a schematic illustration of an elastic nonwoven material fabricated using another embodiment of the system of FIG. 26.
Figure 32:
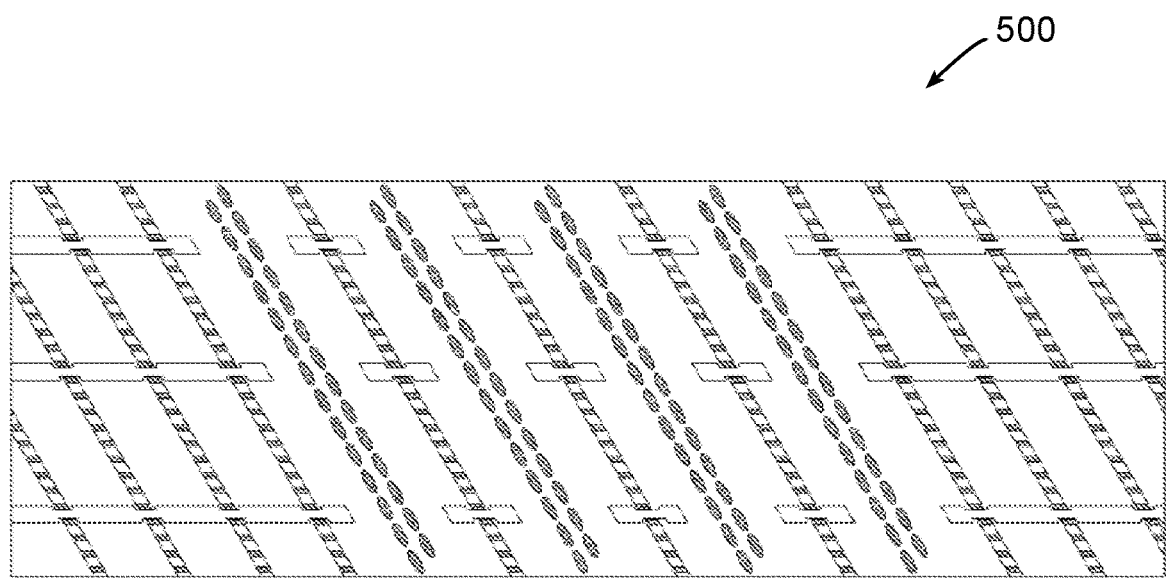
FIG. 32 is a schematic illustration of an elastic nonwoven material fabricated using another embodiment of the system of FIG. 26.
Figure 33:
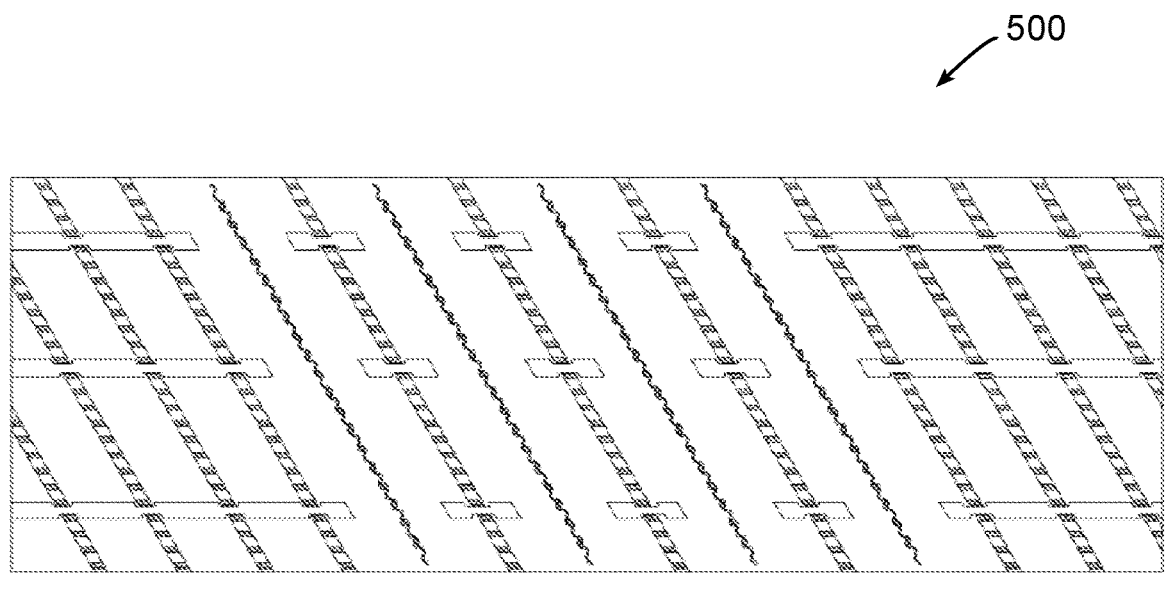
FIG. 33 is a schematic illustration of an elastic nonwoven material fabricated using another embodiment of the system of FIG. 26.
Figure 34:
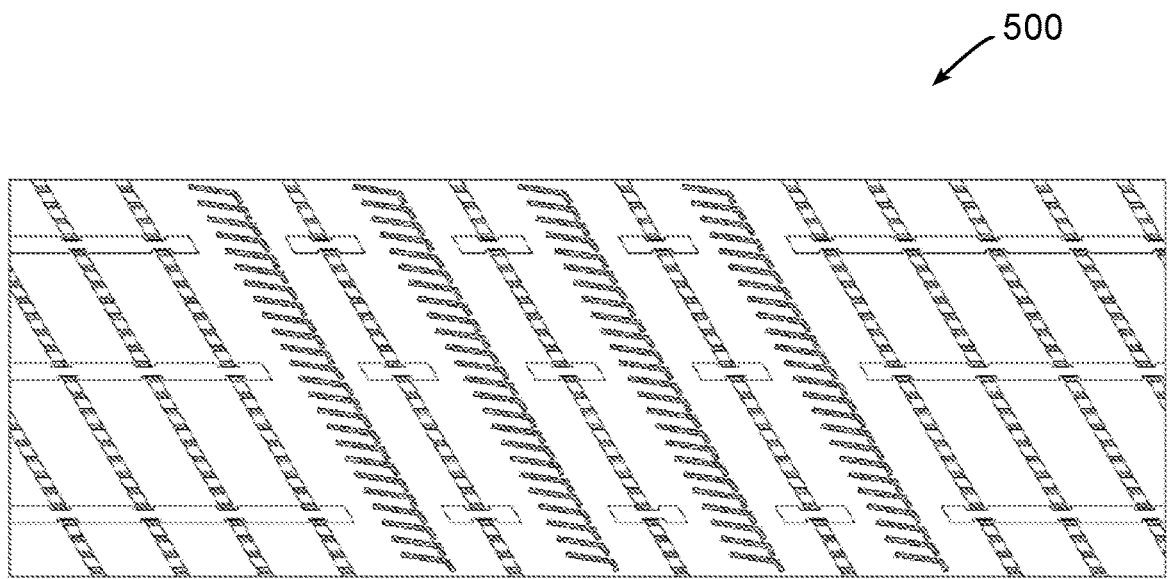
FIG. 34 is a schematic illustration of an elastic nonwoven material fabricated using another embodiment of the system of FIG. 26.
Figure 35:
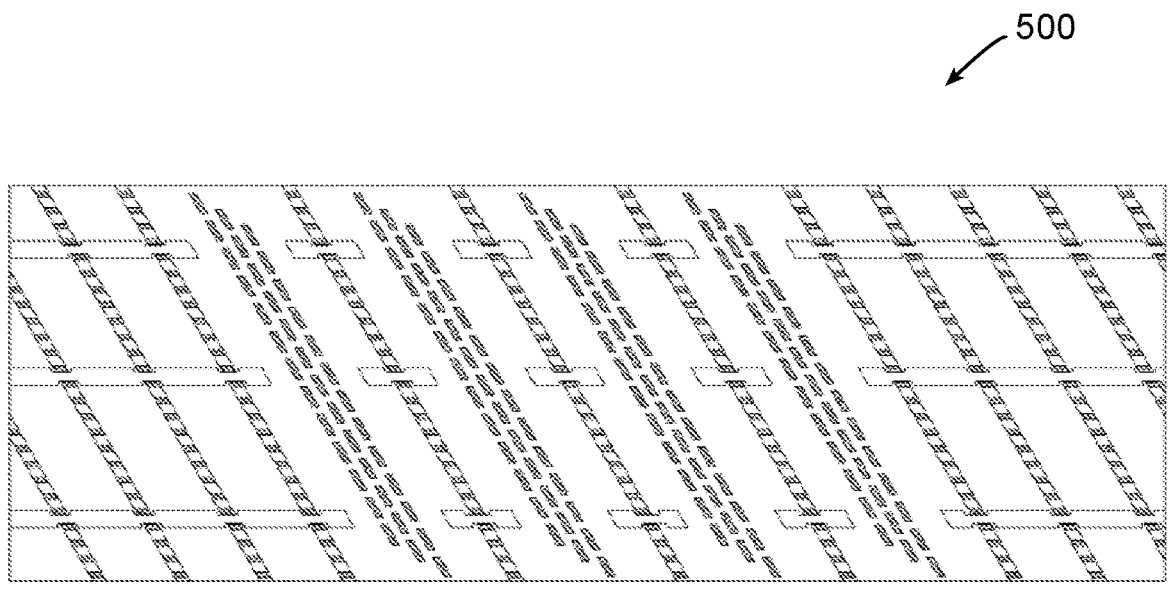
FIG. 35 is a schematic illustration of an elastic nonwoven material fabricated using another embodiment of the system of FIG. 26.

FIG. 27 is a schematic illustration of an elastic nonwoven material fabricated using an embodiment of the system of FIG. 26. In the illustrated embodiment, the elastic nonwoven material 500 includes at least one elastic strand 504 and the nonwoven fabric 506. The elastic nonwoven material 500 further includes the first region 508, the second region 510, and the third region 512. The elastic strand 504 is retained on the nonwoven fabric 506 in at least the first region 508 and the third region 512. For example, the elastic strand 504 may be entrapped within the first region 508 and the third region 512 of the nonwoven fabric 506 by the ridges 280 in the second region 528 on the anvil face 226 (shown in FIG. 26). For example, the lands 284 (shown in FIG. 26) on the ridges 280 define a plurality of bond points 532 on the elastic nonwoven material 500, and the bond points 532 are spaced to facilitate retaining and entrapping the elastic strands 504 between adjacent bond points 532.

In the second region 510, the elastic strands 504 may be severed or cut by the bonding and cutting members 530 of the ridges 524. As a result, the elastic strands 504 are at least partially free in the second region 510, such that free ends 522 of the elastic strands 504 extend on either side of the bond points 532. Moreover, the bond points 532 prevent free elastic strands 504 from being disbursed as debris and causing damage to or cluttering the elastic nonwoven material 500 and the apparatus 200 (shown in FIG. 1).

In the illustrated embodiment, the bonding and cutting members 530 (shown in FIG. 26) act on the nonwoven fabric 506 to cut the elastic strands 504 and to simultaneously bond the nonwoven sheets 112 and 116 (shown in FIG. 1) of the nonwoven fabric 506. For example, the bonding and cutting members 530 define a plurality of bond points 534 on the nonwoven fabric 506 during performance of the bonding and cutting operation. Thus, the nonwoven sheets 112 and 116 are bonded together in the second region 510, but may have different elastic properties than in the regions 508 and 512. For example, in the first region 508 and the third region 512, the elastic strands 504 are under tension and may cause the nonwoven fabric 506 to gather. In the second region 510, the elastic strands 504 are relaxed and the nonwoven fabric 506 is not caused to gather by the elastic strands. As such, the nonwoven material 506 in the regions 508, 510, and 512 may be formed with a pattern having a similar overall appearance, but that have different elastic properties.

FIGS. 28-35 are schematic illustrations of an elastic nonwoven material fabricated using other embodiments of the system of FIG. 26. That is, the ridges 524 and the bonding and cutting members 530 may have any shape, size, and/or configuration that enables the system to function as described herein. Variations of different bond points, and groupings of bond points, that may be formed in the elastic nonwoven material 500 by the various ridges 524 and bonding and cutting members 530 are illustrated in FIGS. 28-35.

Figure 36:
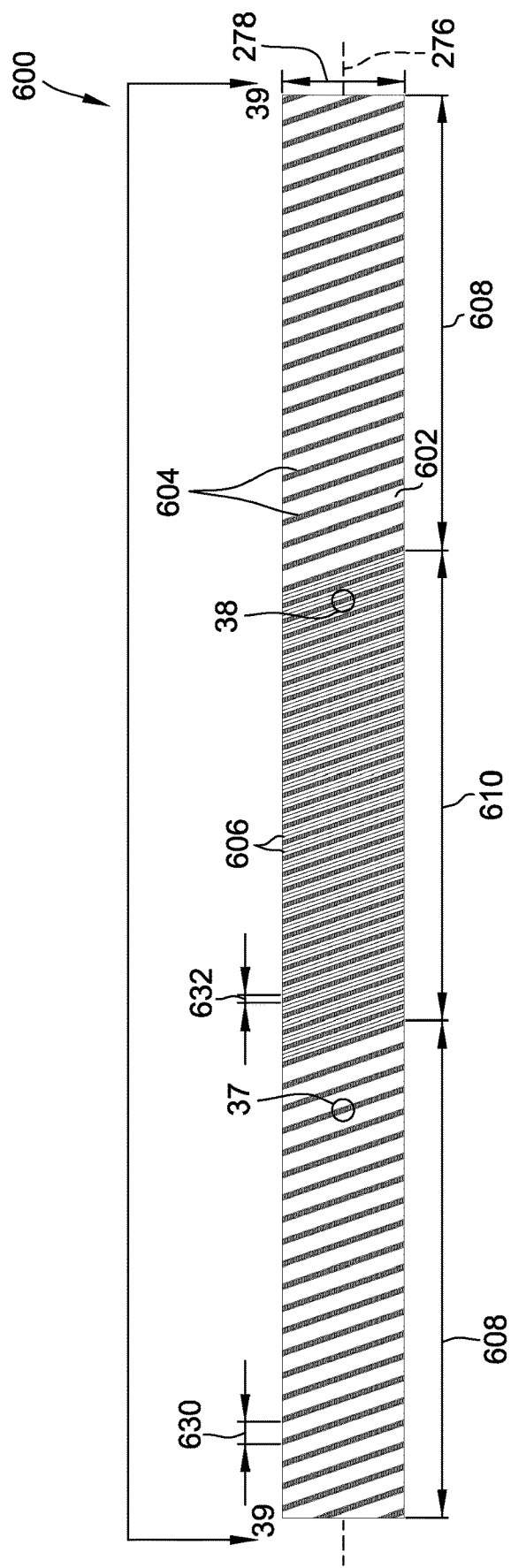
FIG. 36 is a laid-flat illustration of an annular face of one embodiment of an anvil for use in the apparatuses of FIGS. 2-7.
Figure 37:
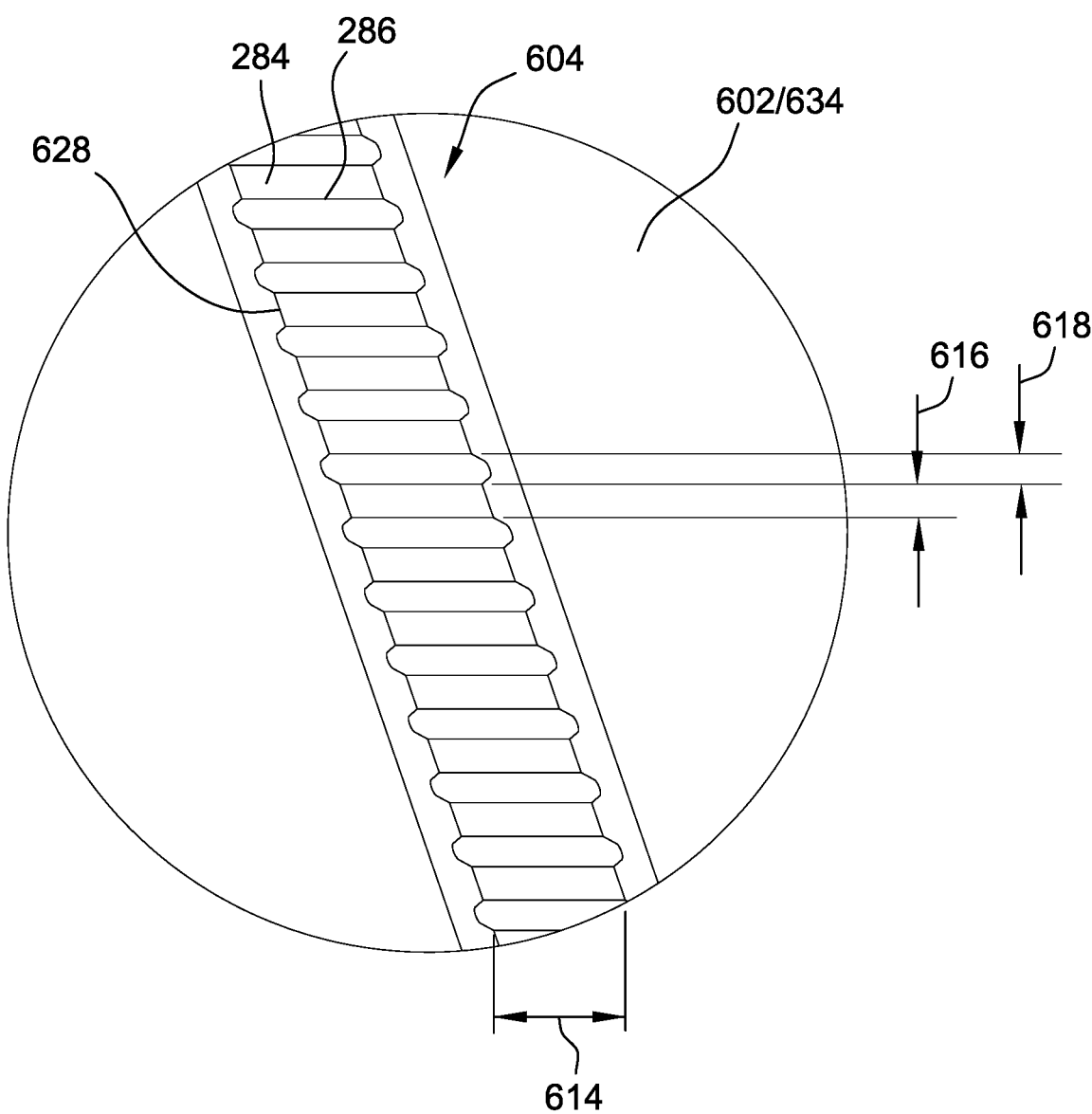
FIG. 37 is an enlarged segment of the annular face of FIG. 36 taken within area 37 of FIG. 36.
Figure 38:
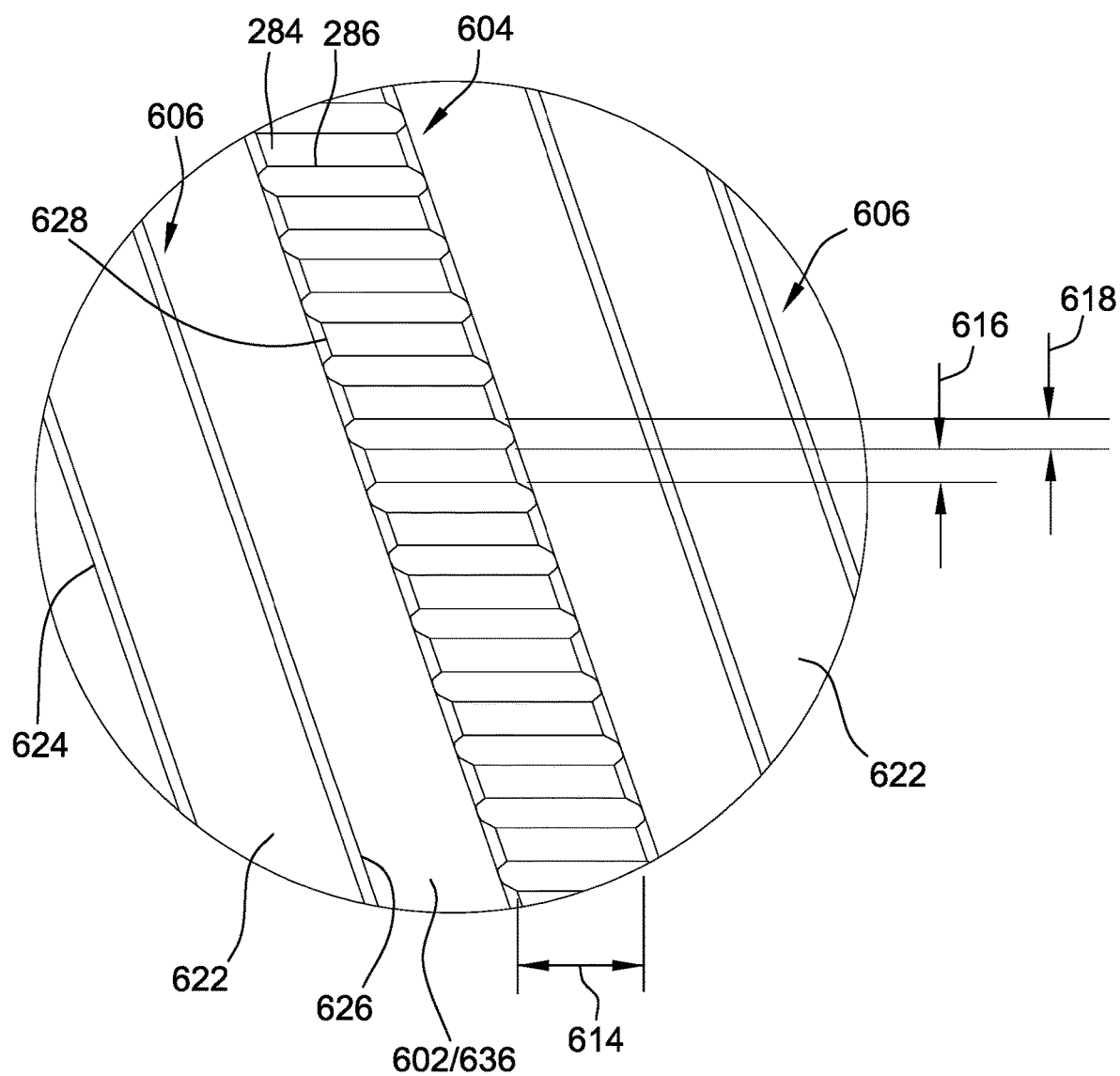
FIG. 38 is an enlarged segment of the annular face of FIG. 36 taken within area 38 of FIG. 36.

FIGS. 36-38 are laid-flat illustrations of an annular face of one embodiment of an anvil 600 for use in the apparatuses of FIGS. 2-7. In the illustrated embodiment, the anvil 600 includes an anvil face 602 having a plurality of ridges formed thereon, including a plurality of first ridges 604 and a plurality of second ridges 606. The ridges 604 and 606 extend linearly and/or obliquely across the circumferential axis 276, and extend across substantially the entire width dimension 278 of the anvil face 602. The ridges 604 and 606 may also extend non-linearly across the circumferential axis 276, and may be spaced from one another by any suitable regular or irregular distance along the circumferential axis 276, as will be described in more detail below.

In one suitable embodiment, the ridges 604 and 606 are arranged on the anvil face 602 to define a first zone 608 and a second zone 610 along the circumferential axis 276. The first zone 608 includes a plurality of first ridges 604 arranged sequentially along the circumferential axis 276. The plurality of first ridges 604 define a plurality of interspaced lands 284 and notches 286 that are configured to perform a continuous entrapment bonding operation, as described above. That is, in the first zone 608, each of the first ridges 604 has at least one notch 286 that is aligned in the width dimension 278 with a corresponding notch 286 of an adjacent first ridge 604, and the lands 284 that flank each aligned notch 286 are spaced to create a pair of widthwise adjacent bonds in the nonwoven fabrics 112, 116 (shown in FIG. 1) that are close enough together in the width dimension 278 to permanently hold (i.e., entrap) at least one of the elastic strands 504 (shown in FIG. 27) in tension therebetween.

The second zone 610 includes a plurality of first ridges 604 and a plurality of second ridges 606 alternatingly arranged along the circumferential axis 276 such that at least one first ridge 604 is positioned between a pair of second ridges 606 along the circumferential axis 276. The second ridges 606 are configured to sever or cut the elastic strands 504 extending within the second zone 610. As a result, the elastic strands 504 are severed to define a plurality of discrete strand segments 612 (shown in FIG. 27). In one suitable embodiment, the discrete strand segments 612 are entrapped between the nonwoven fabrics 112, 116 by the bond points 532 formed by the first ridge 604 positioned between the pair of second ridges 606. Thus, movement of the discrete strand segments 612 relative to the nonwoven fabrics 112, 116 is restricted.

Figure 40:
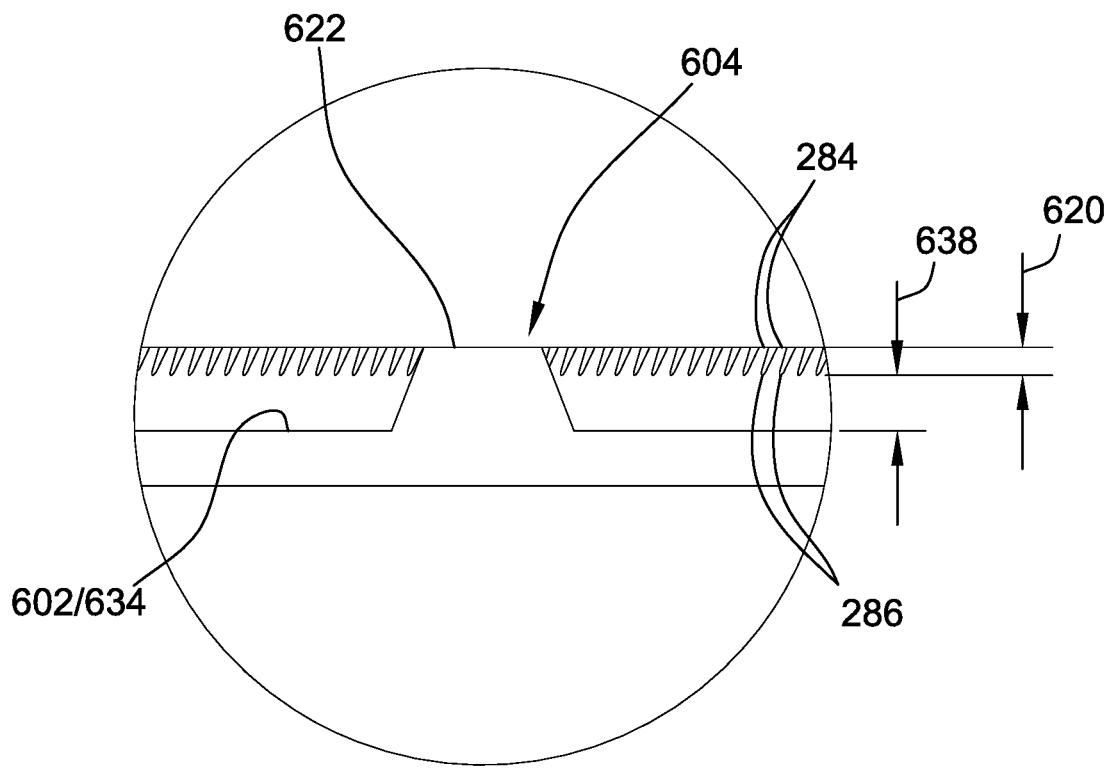
FIG. 40 is an enlarged segment of the anvil of FIG. 39 taken within area 40 of FIG. 39.
Figure 41:
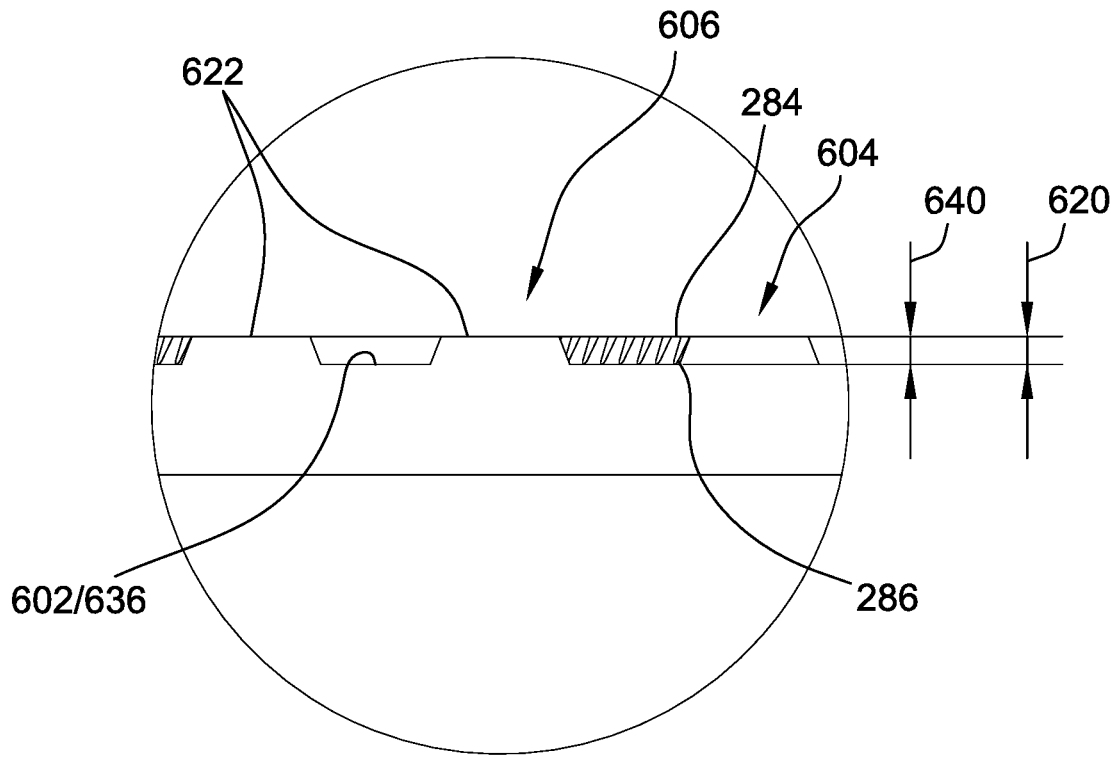
FIG. 41 is an enlarged segment of the anvil of FIG. 39 taken within area 41 of FIG. 39.

Referring to FIG. 37, the dimensions of lands 284 and notches 286 on the first ridges 604 are adapted to perform a continuous entrapment bonding operation while minimizing the occurrence of the elastic strands 504 being severed during the bonding operation. In one particular embodiment, if the elastic strands 504 have a decitex of between about 300 and about 1240, and if the nonwoven fabrics 112, 116 have a grammage (gsm) of between about 8 and about 30, the lands 284 may have lengths 614, relative to the circumferential axis 276, at their peaks of between about 0.010 inch and about 0.25 inch (e.g., between about 0.030 inch and about 0.060 inch), and widths 616 at their peaks of between about 0.008 inch and about 0.050 inch (e.g., between about 0.010 inch and about 0.030 inch). Also, in that example, the notches 286 may have widths 618 measured at the peaks of their flanking lands 284 of between about 0.006 inch and about 0.016 inch (e.g., between about 0.008 inch and about 0.015 inch), and widths measured at their bases of between about 0.002 inch and about 0.02 inch (e.g., between about 0.004 inch and about 0.015 inch). As illustrated in FIGS. 40 and 41, the notches 286 may also have notch depths 620 of between about 0.005 inch and about 0.02 inch (e.g., between about 0.075 inch and about 0.0125 inch).

Referring to FIG. 38, the second ridge 606 has a radial outer surface 622 defined between a leading edge 624 and a trailing edge 626 thereof. In the illustrated embodiment, the radial outer surface 622 is continuous and free of interspaced lands and notches. Thus, the second ridge 606 forms a substantially continuous bonding region in the nonwoven fabrics 112, 116. The substantially continuous bonding region is oriented to intersect with the path of the elastic strands 504 directed between the nonwoven fabrics 112, 116 in the machine direction. Thus, the heat and/or pressure generated during formation of the substantially continuous bonding region facilitates severing the elastic strands 504.

The second ridge 606 may have any suitable profile or cross-sectional shape that enables sufficient heat and/or pressure to be generated for severing the elastic strands 504. In the illustrated embodiment, the radial outer surface 622 is defined at a constant height from the anvil face 602 from the leading edge 624 to the trailing edge 626. Accordingly, a substantially uniform pressure distribution may be formed across the radial outer surface 622 for generating heat and/or pressure for severing the elastic strands 504 without piercing the nonwoven fabrics 112, 116. In an alternative embodiment, the second ridge 606 may have any cross-sectional shape that enables the elastic strands 504 to be severed. In one suitable embodiment, the second ridge 606 has a cross-sectional shape that defines a cutting edge on the anvil face 602. In such an embodiment, the second ridge 606 may have a shorter length along the circumferential axis 276, and/or have a lesser radius of curvature, than the radial outer surface 622 illustrated in FIG. 41.

As described above, the elastic strands 504 are fed between the nonwoven fabrics 112, 116 in a tensioned state when forming the elastic nonwoven material 134. Accordingly, when severed by the second ridges 606, the elastic strands 504 have a tendency to snap back in the machine direction, which may result in the elastic strands 504 retracting past an adjacent ridge before an entrapment bonding operation can be performed. The anvil 600 described herein includes one or more features for limiting the snap back potential of the elastic strands 504 that become severed between the horn 208 and anvil 600 during a bonding and cutting operation.

For example, in the illustrated embodiment, each first ridge 604 has a leading edge 628. In the first zone 608, the first ridges 604 are arranged sequentially along the circumferential axis 276, and a first pitch distance 630 is defined between the leading edges 628 of adjacent first ridges 604. The first pitch distance 630 may be any length that facilitates providing continuous running contact during operation of the apparatus 200. In one particular embodiment, the first pitch distance 630 is between about 0.2 inch and about 0.3 inch, such as between about 0.225 inch and about 0.275 inch.

To limit the snap back potential of the elastic strands 504, a second pitch distance 632 is defined between the leading edges 628 and 624 of adjacent first and second ridges 604 and 606 in the second zone 610. In the illustrated embodiment, the second pitch distance 632 is shorter than the first pitch distance 630. In one suitable embodiment, the second pitch distance 632 is shorter than the first pitch distance 630 by a factor of less than about 0.5 (e.g., less than about 0.4). Reducing the spacing between adjacent first and second ridges 604 and 606 in the second zone 610 reduces the snap back distance between the adjacent ridges 604 and 606. Thus, when the elastic strand 504 is severed by a second ridge 606, an adjacent first ridge 604 is positioned to contact and bond the severed elastic strand 504 to the nonwoven fabrics 112, 116 before it has time to retract past the adjacent first ridge 604. In one particular embodiment, the second pitch distance 632 is between about 0.075 inch and about 0.1 inch, such as between about 0.085 inch and about 0.095 inch.

Figure 39:
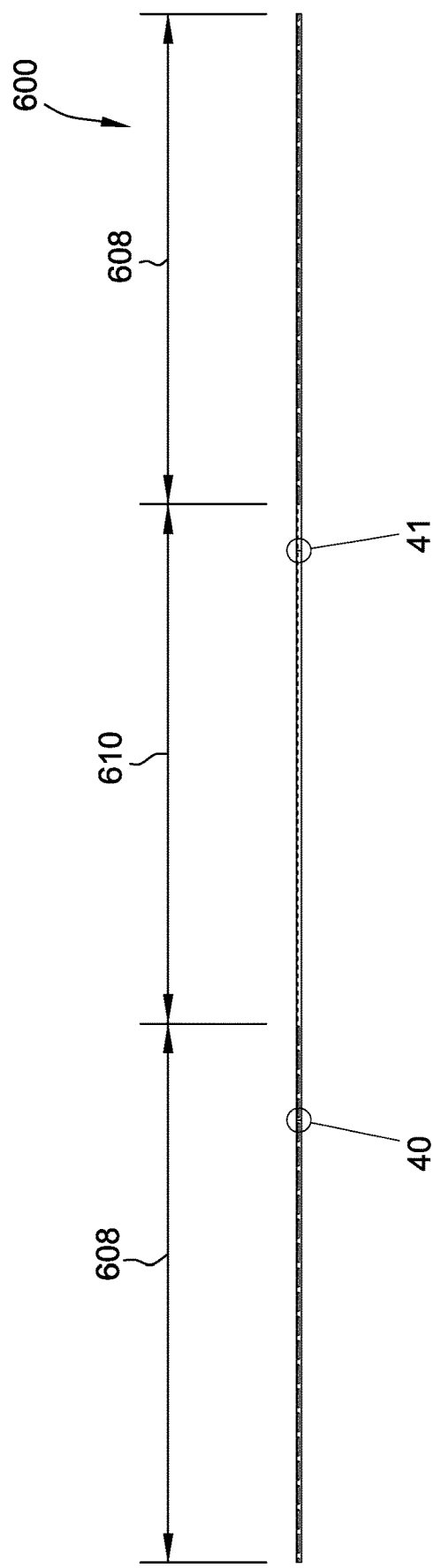
FIG. 39 is a side view illustration of the anvil shown in FIG. 36.
Figure 42:
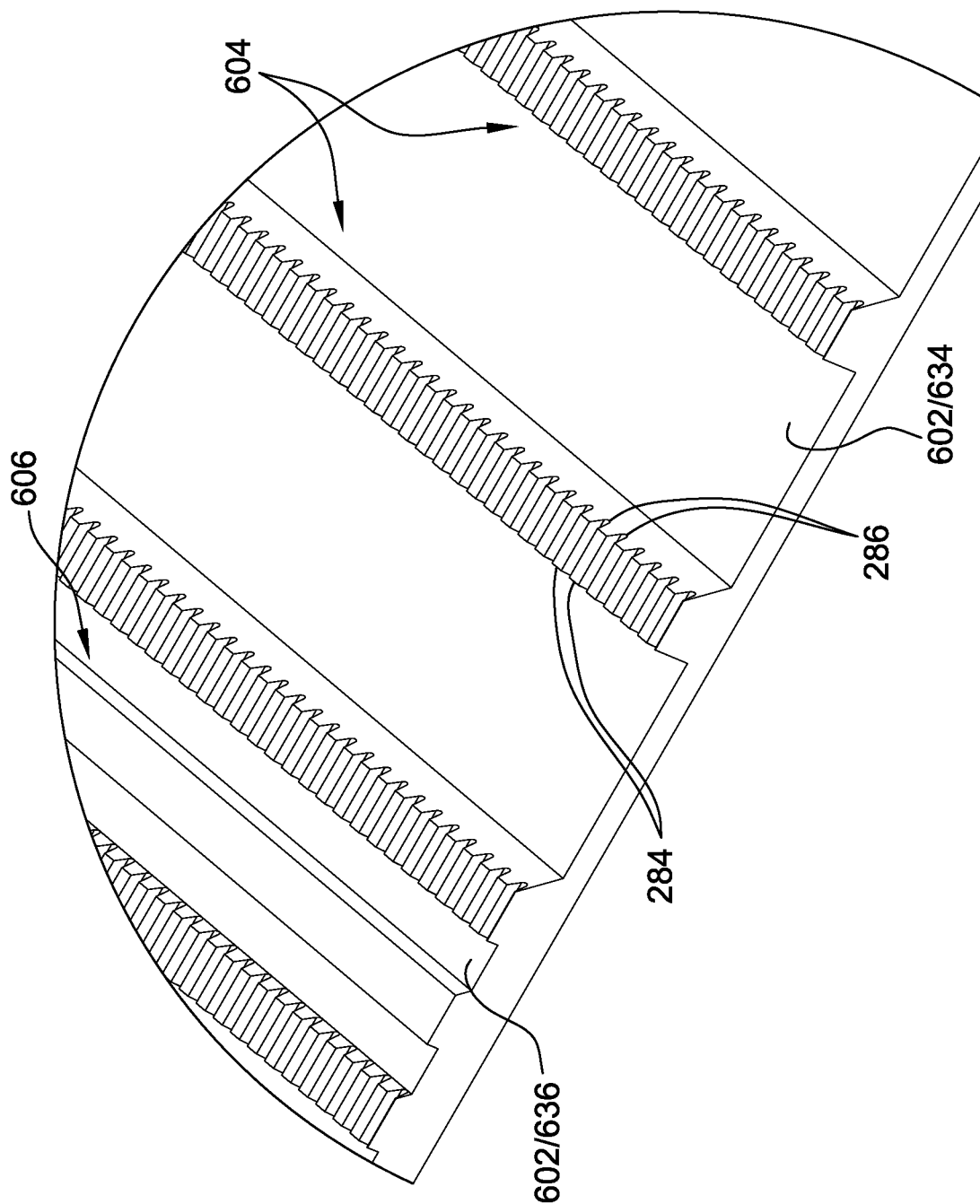
FIG. 42 is a perspective view of a portion of the annular face of FIG. 36.
Figure 43:
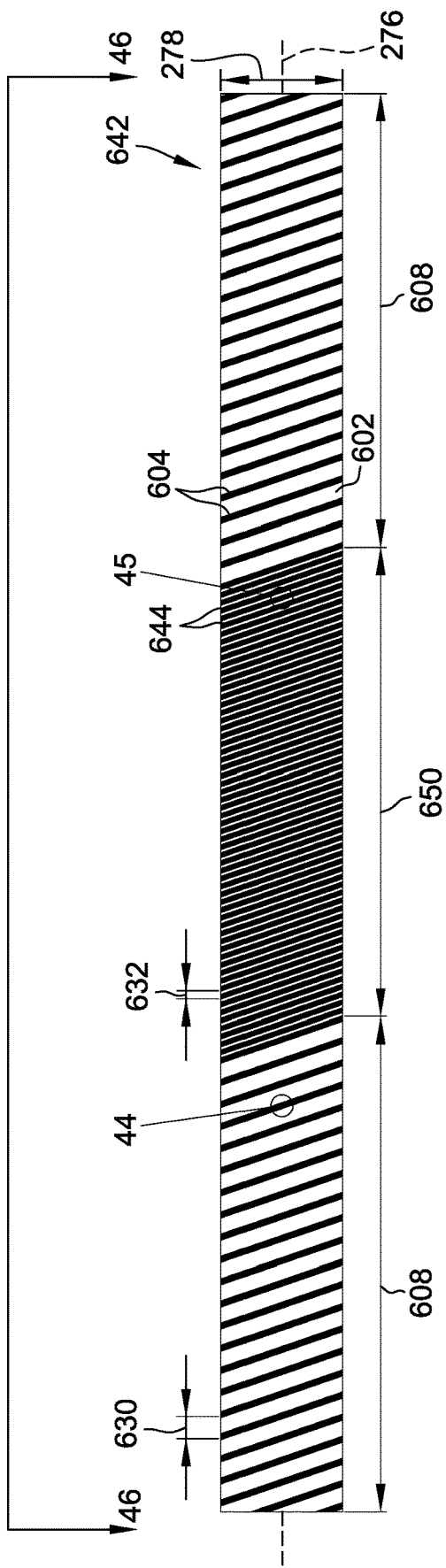
FIG. 43 is a laid-flat illustration of an annular face of one embodiment of an anvil for use in the apparatuses of FIGS. 2-7.
Figure 44:
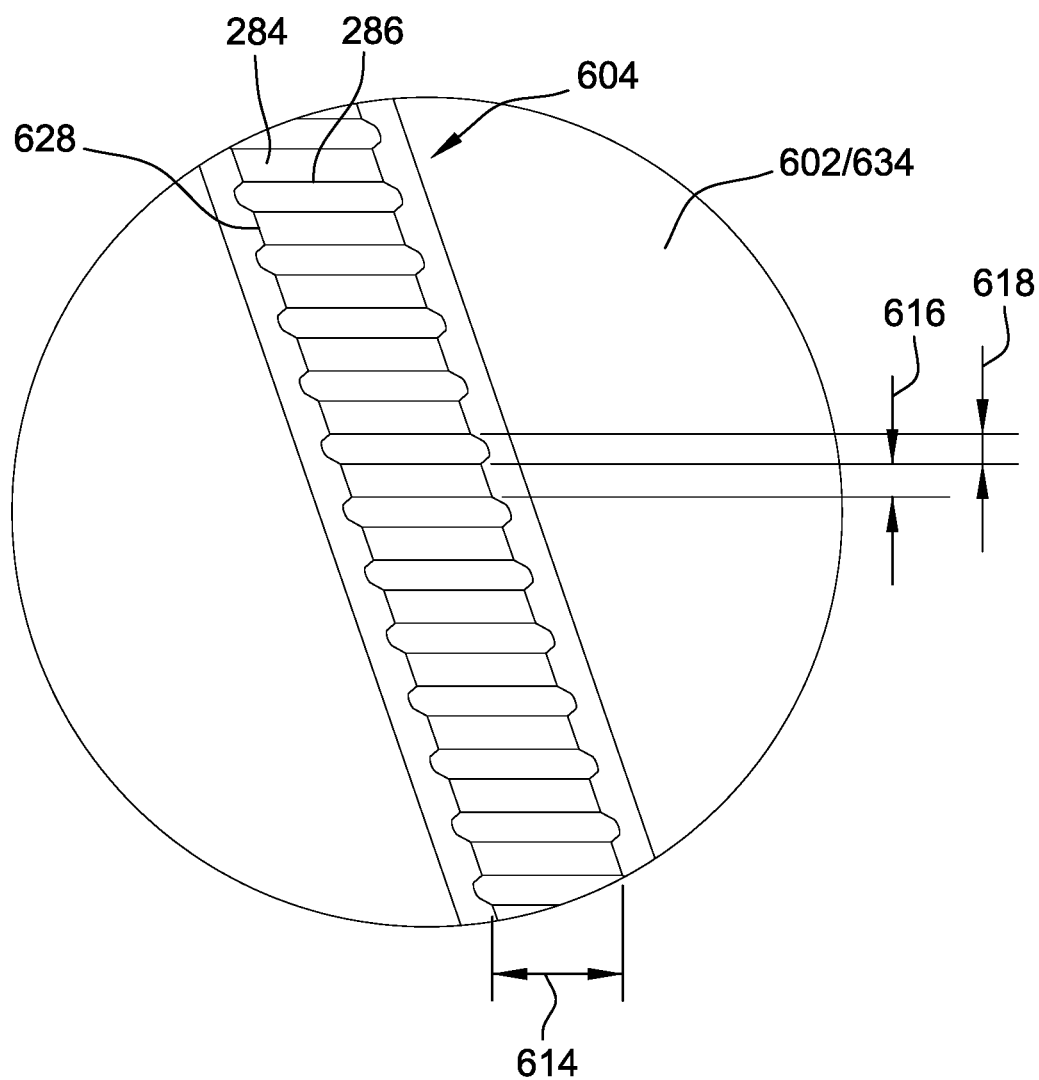
FIG. 44 is an enlarged segment of the annular face of FIG. 43 taken within area 44 of FIG. 43.
Figure 45:
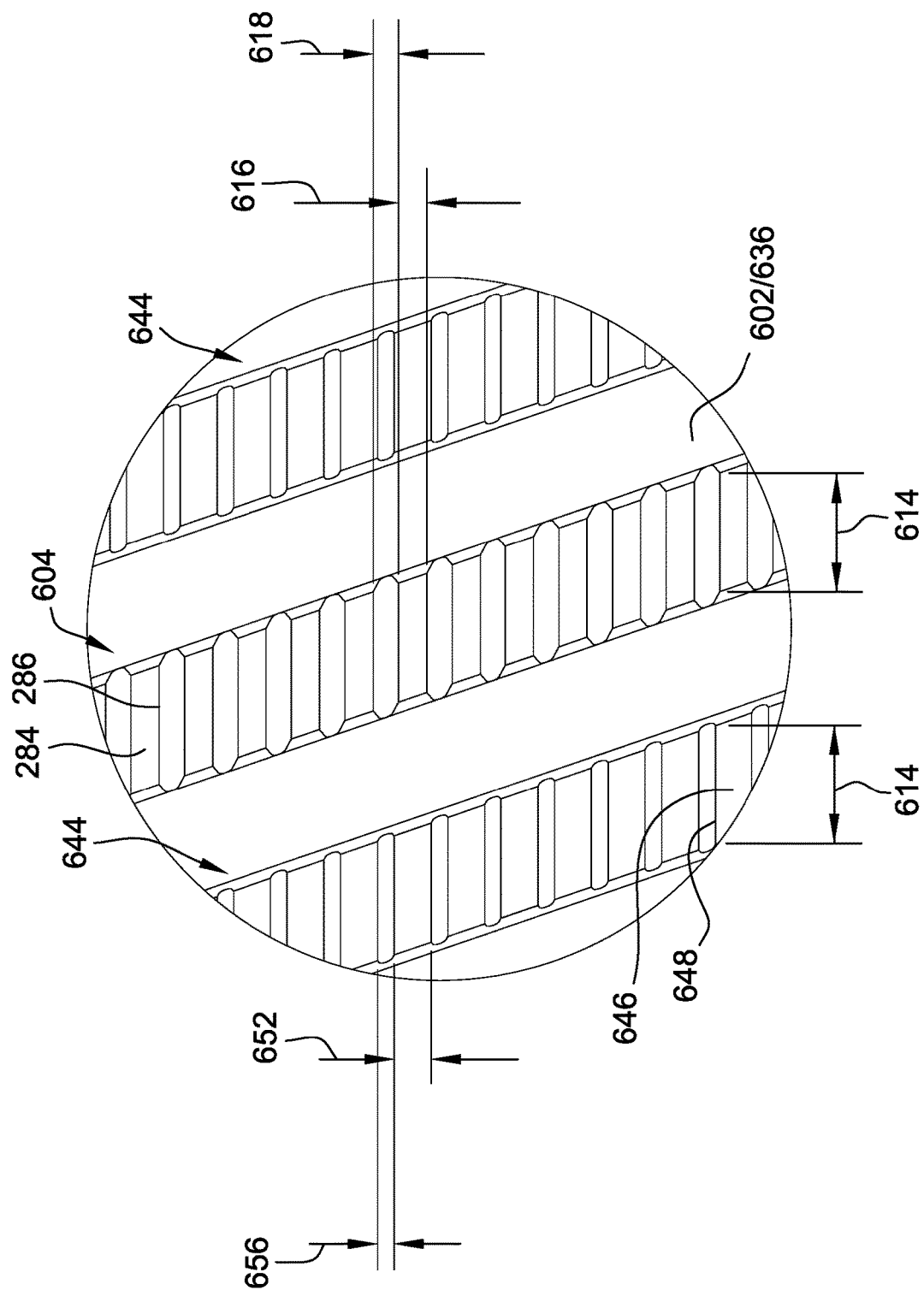
FIG. 45 is an enlarged segment of the annular face of FIG. 43 taken within area 45 of FIG. 43.
Figure 46:
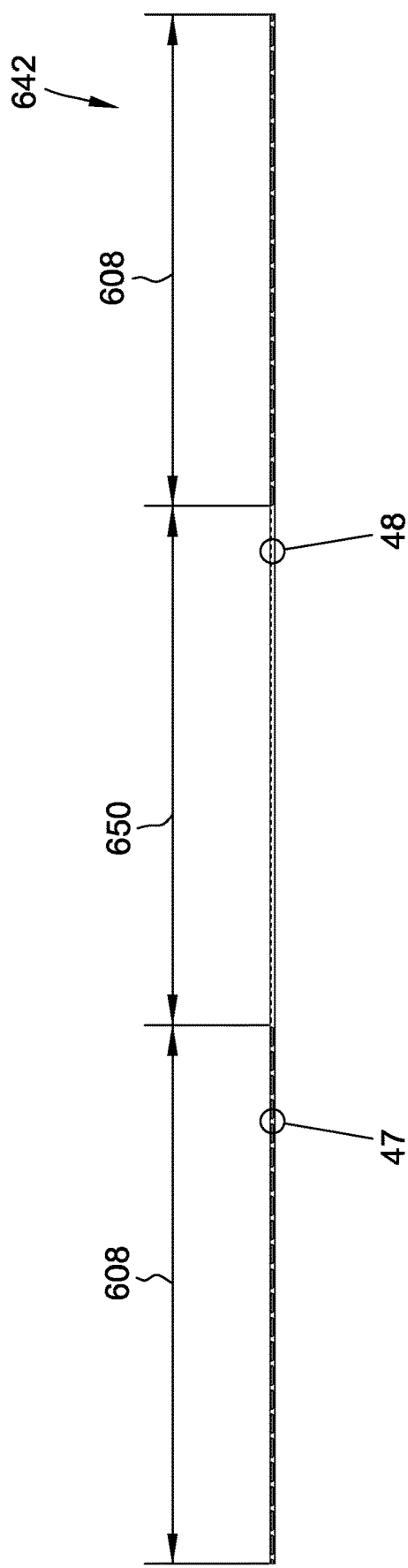
FIG. 46 is a side view illustration of the anvil shown in FIG. 43.

FIGS. 39-41 are side view illustrations of the anvil 600, and FIG. 42 is a perspective view of a portion of the anvil face 602. As described above, the anvil 600 described herein includes features for limiting the snap back potential of the elastic strands 504 that become severed between the horn 208 and the anvil 600 during a bonding and cutting operation. In the illustrated embodiment, the anvil face 602 of the anvil 600 is adapted to generate an increased friction force in the second zone 610, as compared to the first zone 608, to limit the snap back potential of the elastic strands 504. For example, the first and second ridges 604 and 606 are raised relative to the anvil face 602 such that a gap is defined between the horn 208 and the anvil face 602 when the horn 208 is positioned in close proximity to the anvil 600. The gap is sized to compress the nonwoven fabrics 112, 116 and the elastic strands 504 between the horn 208 and the anvil face 602 to generate a frictional force during performance of the bonding operation. The gap size in the first zone 608 and the second zone 610, and the frictional forces formed thereby, may be adapted to limit the snap back potential of the elastic strands 504.

In the illustrated embodiment, the anvil face 602 defines a surface 634 between adjacent first ridges 604 in the first zone 608, and defines a raised surface 636 between adjacent first and second ridges 604 and 606 in the second zone 610. Accordingly, a first gap is defined between the horn 208 and the surface 634, and a second gap is defined between the horn 208 and the raised surface 636. The surface 634 and the raised surface 636 are radially offset from each other relative to a centerline of the anvil 600 such that the first gap is larger than the second gap. The reduced gap distance between the anvil face 602 and the horn 208 within the second zone 610 provides additional compression of the nonwoven fabrics 112, 116 and the elastic strands 504 routed between the anvil face 602 and the horn 208 relative to the compression provided within the first zone 608. The additional compression generates an increased friction force in the second zone 610, as compared to the first zone 608, for limiting the snap back potential of the elastic strands 504. Accordingly, when the elastic strands 504 become severed, the increased friction force reduces the speed at which the elastic strands 504 retract relative to the nonwoven fabrics 112, 116, which enables the discrete strand segments 612 to be entrapped within the second zone 610.

When the horn 208 is positioned in close proximity to the anvil 600, the gaps defined between the horn 208 and the anvil face 602 is approximately equal to the height of the respective first and second ridges 604 and 606 relative to the anvil face 602. As illustrated in FIG. 40, a first ridge height 638 is defined between the surface 634 of the anvil face 602 and the radial outer surface 622 of the first ridge 604. As illustrated in FIG. 41, a second ridge height 640 is defined between the raised surface 636 of the anvil face 602 and the radial outer surfaces 622 of the first and second ridges 604 and 606.

In one particular embodiment, if the elastic strands 504 have a decitex of between about 300 and about 1240, and if the nonwoven fabrics 112, 116 have a grammage (gsm) of between about 8 and about 30, the first ridge height 638 (i.e., the first gap between the horn 208 and the surface 634) may be between about 0.02 inch and about 0.04 inch, such as between about 0.025 inch and about 0.035 inch), and the second ridge height 640 (i.e., the second gap between the horn 208 and the raised surface 636) may be between about 0.005 inch and about 0.02 inch, such as between about 0.075 inch and about 0.0125 inch). The grammage of the nonwoven fabrics 112, 116 may be substantially the same, or may be different from each other.

In such an example, the gap between the horn 208 and the anvil face 602 in the first zone 608 is larger than the gap between the horn 208 and the anvil face 602 in the second zone 610. Accordingly, the elastic nonwoven material 134 is frictionally engaged between the horn 208 and the anvil face 602 with a first friction force in the first zone 608, and is frictionally engaged between the horn 208 and the anvil face 602 with a second friction force in the second zone 610. The second friction force is greater than the first friction force since the same volume and/or mass of material (i.e., the nonwoven fabrics 112, 116 and the elastic strands 504) is passed between the horn 208 and the anvil face 602 in the second zone 610 as in the first zone 608. The second friction force generated as a result of the increased compression of the nonwoven fabrics 112, 116 and the elastic strands 504 limits the snap back potential of the elastic strands 504.

FIGS. 43-49 are illustrations of an annular face of one embodiment of an anvil 642 for use in the apparatuses of FIGS. 2-7. In the illustrated embodiment, the anvil 642 includes the anvil face 602 having a plurality of ridges formed thereon, including a plurality of first ridges 604 and a plurality of third ridges 644. The plurality of third ridges 644 each define a plurality of interspaced lands 646 and notches 648.

In one suitable embodiment, the first and third ridges 604 and 644 are arranged on the anvil face 602 to define a first zone 608 and a second zone 650 along the circumferential axis 276. The first zone 608 includes the plurality of first ridges 604 arranged sequentially along the circumferential axis 276. The second zone 650 includes a plurality of first ridges 604 and a plurality of third ridges 644 alternatingly arranged along the circumferential axis 276 such that at least one first ridge 604 is positioned between a pair of third ridges 644 along the circumferential axis 276. The third ridges 644 are configured to sever or cut the elastic strands 504 (shown in FIG. 27) extending within the second zone 650.

In the illustrated embodiment, the notches 648 of the third ridges 644 are configured to sever or cut the elastic strands 504 extending within the second zone 650. That is, in the second zone 650, the notches 648 in the third ridges 644 have at least one of a reduced width or a reduced depth relative to the notches 286 in the first ridges 604, such that the notches 648 have a smaller volume than the notches 286. Throughout performance of a bonding operation, a volume of material (i.e., the nonwoven fabrics 112, 116 and the elastic strands 504) is passed between the horn 208 and the anvil 642. The width and depth dimensions of the notches 648 are adapted to constrict the volume of material passed therethrough for severing the elastic strands 504 included therein. The elastic strands 504 may be severed as a result of heat and/or pressure generated by the lands 646 flanking the notches 648.

In the illustrated embodiment, the lands 284 of the first ridges 604 are aligned in the width dimension 278 with corresponding lands 646 of adjacent third ridges 644, and notches 286 of the first ridges 604 are aligned in the width dimension 278 with corresponding notches 648 of adjacent third ridges 644. Accordingly, the elastic strands 504 circumferentially aligned with the notches 286 and correspondingly aligned notches 648 may be entrapped by the first ridge 604 and severed by the second ridge 606.

The lands 646 that flank each aligned notch 648 are spaced to create a plurality of bond points (e.g., the bond points 534 shown in FIG. 27) in the nonwoven fabrics 112, 116 (shown in FIG. 1), rather than a continuous bonding region formed by the second ridge 606 (shown in FIG. 36). Accordingly, the aesthetic appearance of the elastic nonwoven material 134 may be enhanced by providing consistency in the bond pattern created by the first and third ridges 604 and 644.

Figure 47:
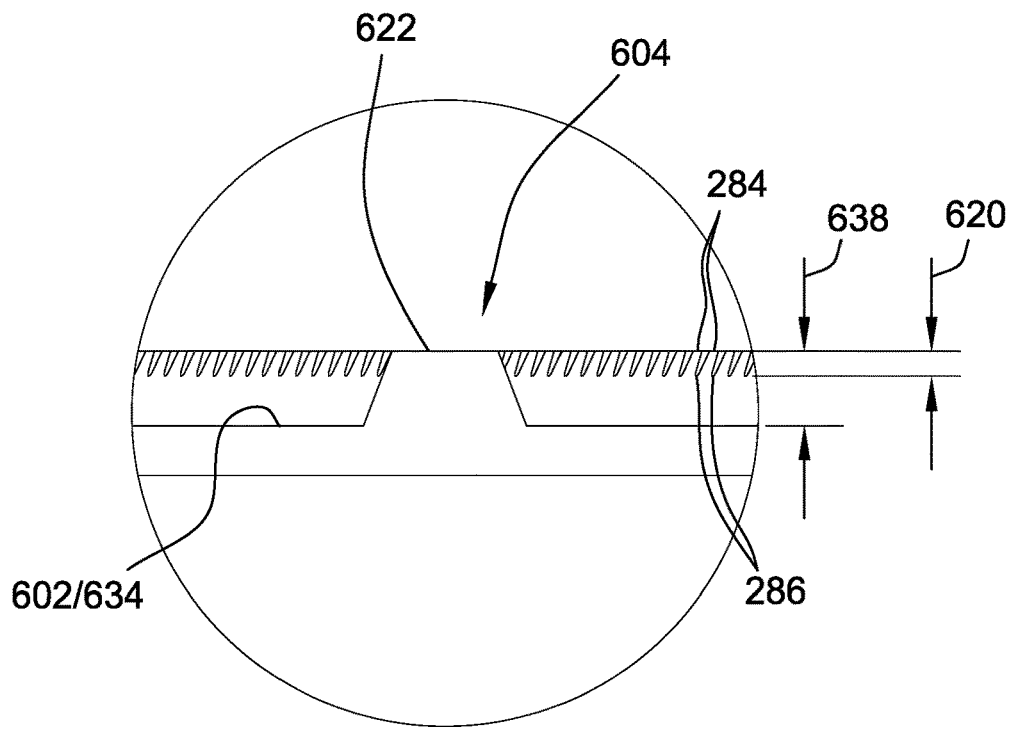
FIG. 47 is an enlarged segment of the anvil of FIG. 46 taken within area 47 of FIG. 46.
Figure 48:
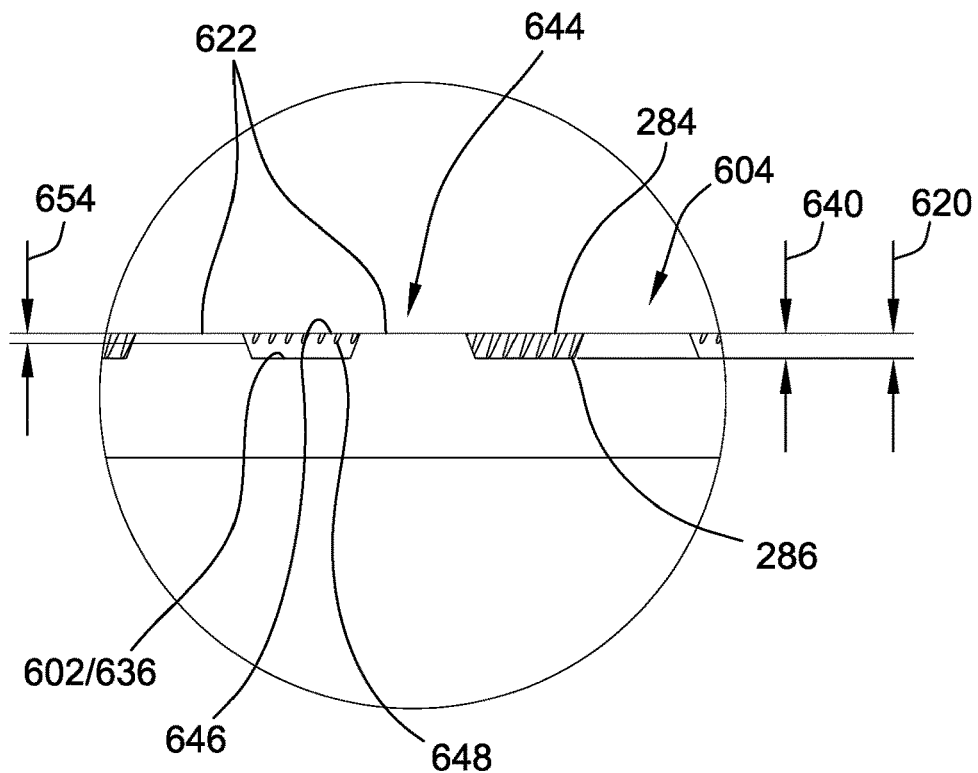
FIG. 48 is an enlarged segment of the anvil of FIG. 46 taken within area 48 of FIG. 46.
Figure 49:
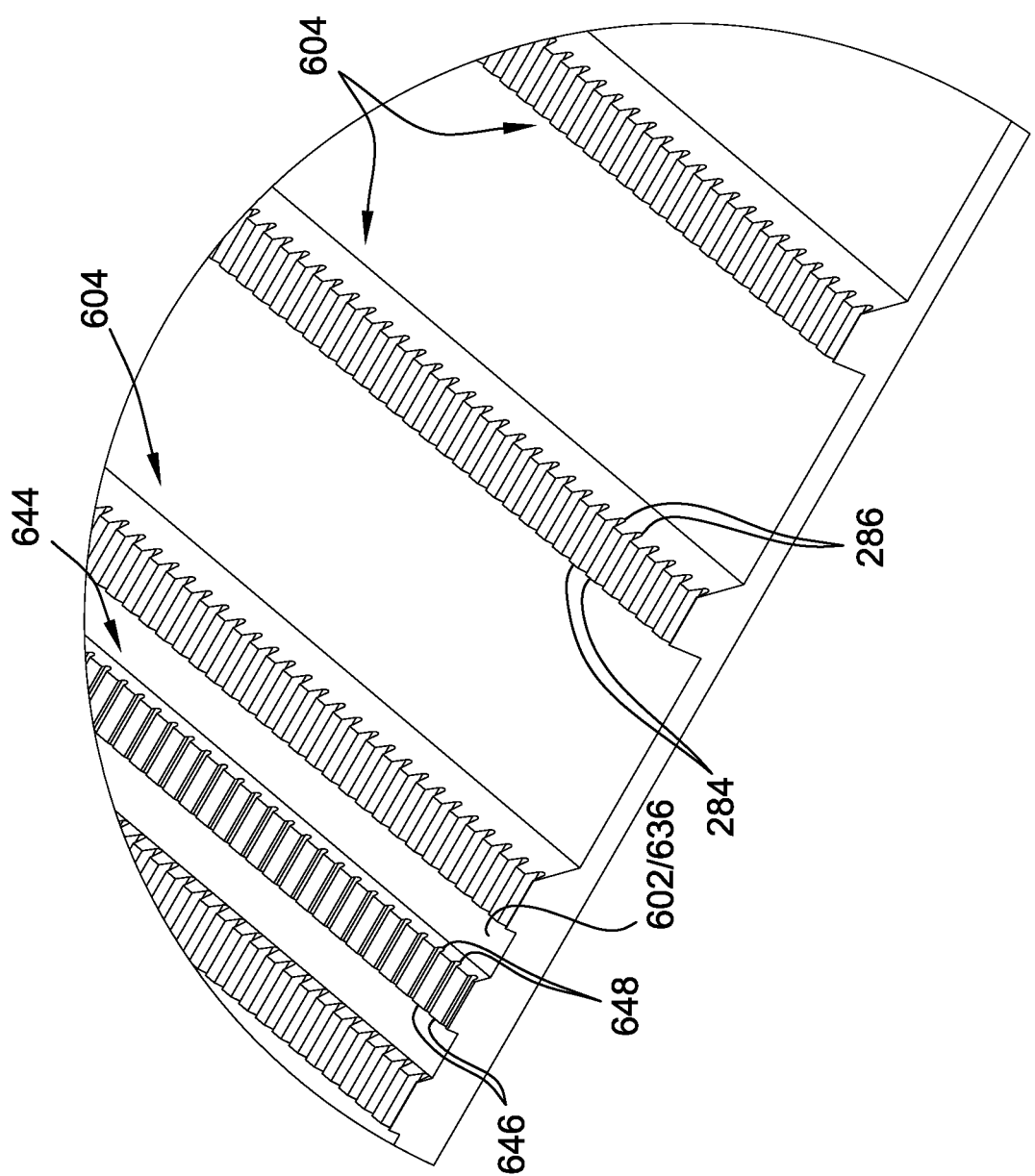
FIG. 49 is a perspective view of a portion of the annular face of FIG. 43.
Figure 50:
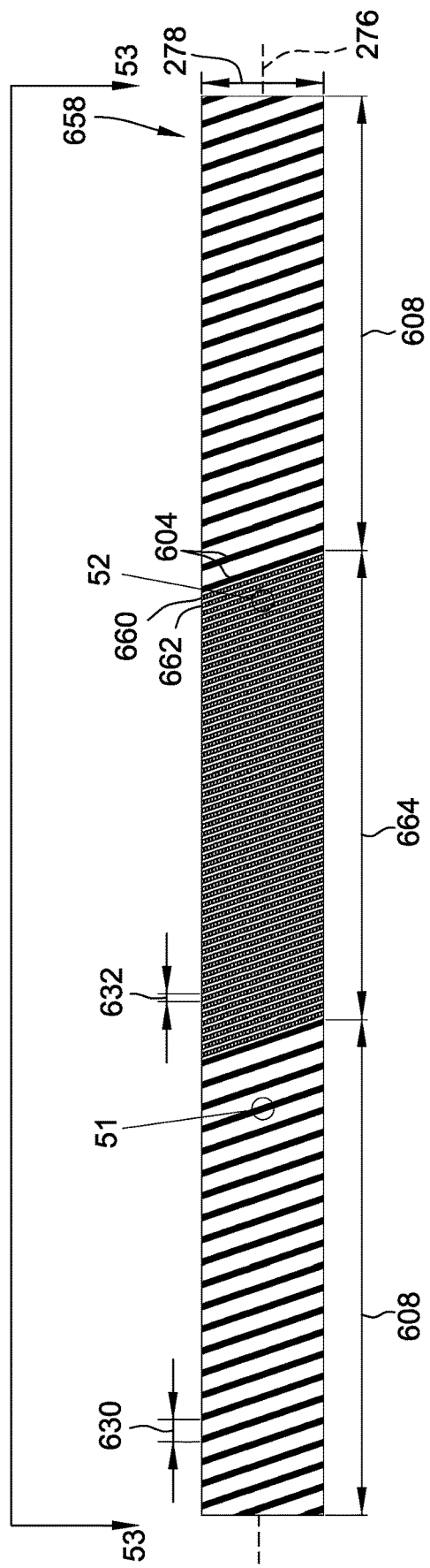
FIG. 50 is a laid-flat illustration of an annular face of one embodiment of an anvil for use in the apparatuses of FIGS. 2-7.
Figure 51:
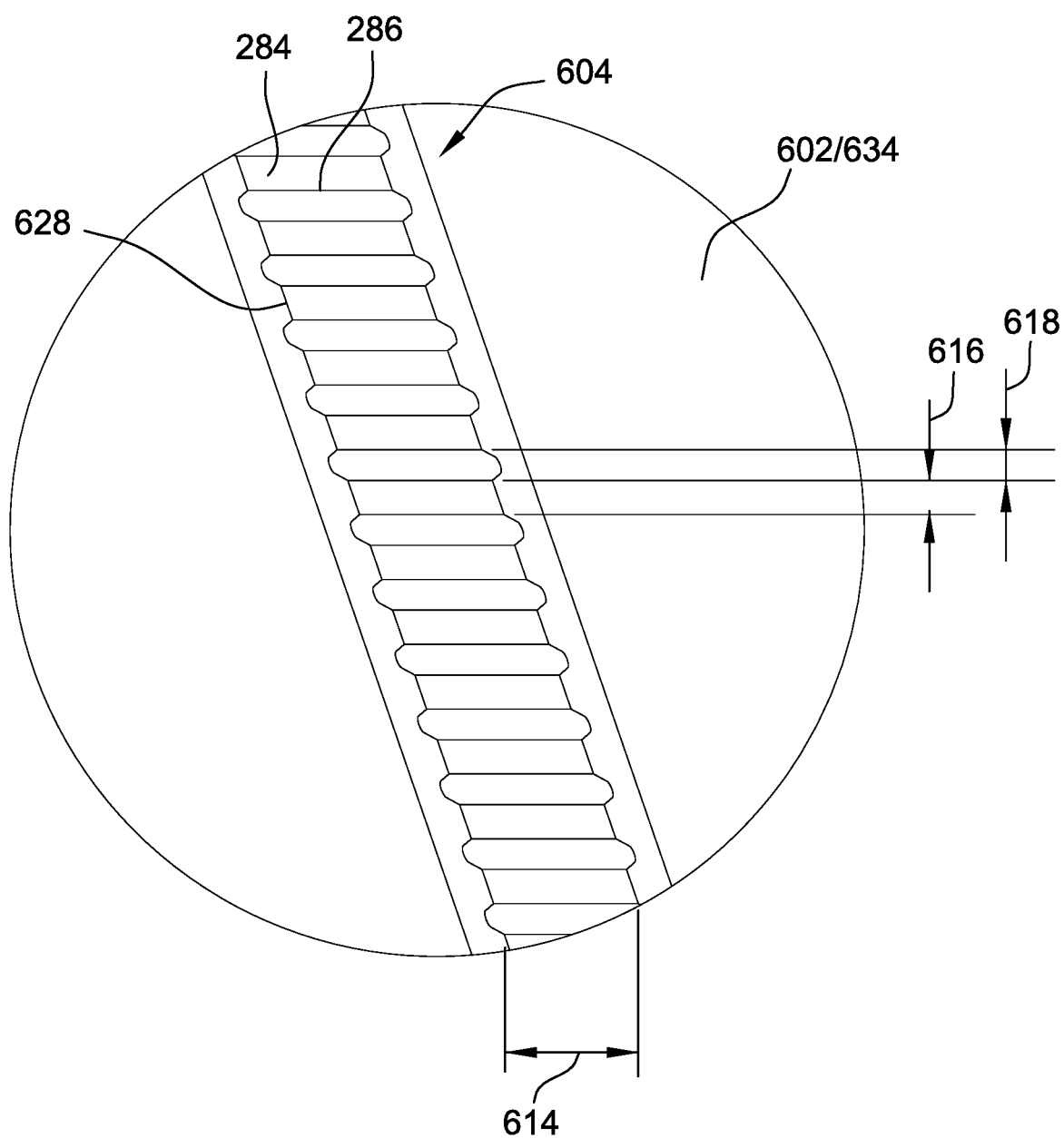
FIG. 51 is an enlarged segment of the annular face of FIG. 50 taken within area 51 of FIG. 50.
Figure 52:
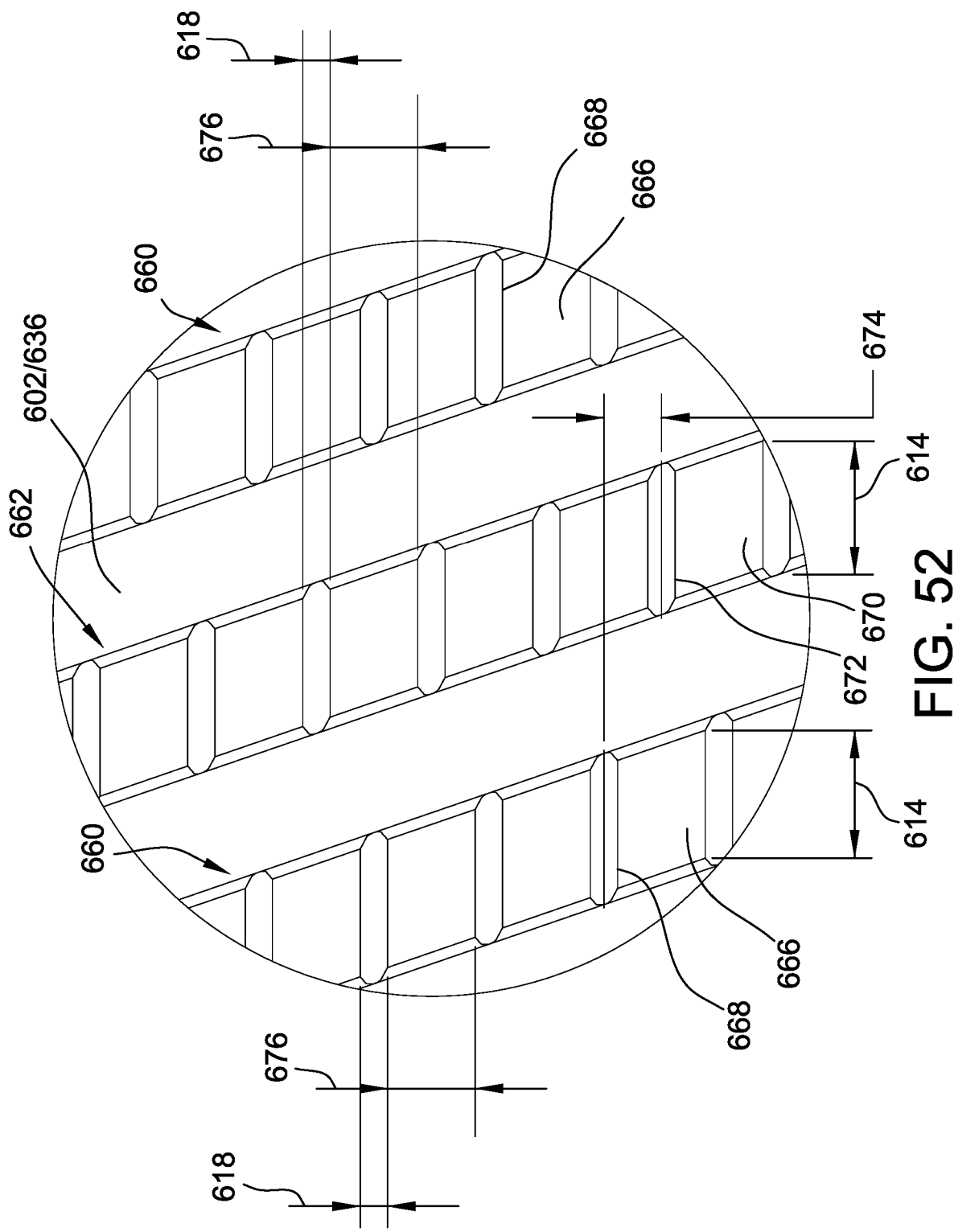
FIG. 52 is an enlarged segment of the annular face of FIG. 50 taken within area 52 of FIG. 50.
Figure 53:
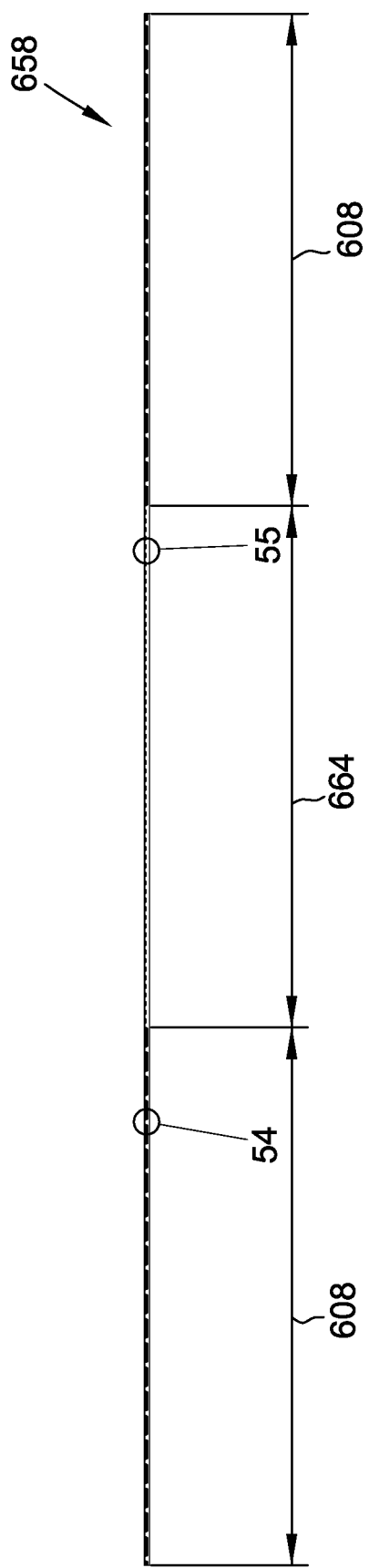
FIG. 53 is a side view illustration of the anvil shown in FIG. 50.

In one particular embodiment, if the elastic strands 504 have a decitex of between about 300 and about 1240, and if the nonwoven fabrics 112, 116 have a grammage (gsm) of between about 8 and about 30, the lands 646 may have lengths 614, relative to the circumferential axis 276, at their peaks of between about 0.010 inch and about 0.25 inch, such as between about 0.030 inch and about 0.060 inch, and widths 652 at their peaks of between about 0.008 inch and about 0.050 inch, such as between about 0.010 inch and about 0.020 inch. Also, in that example, the notches 648 may have widths 656 measured at the peaks of their flanking lands 646 of between about 0.0025 inch and about 0.01 inch, such as between about 0.005 inch and about 0.007 inch, and widths measured at their bases of equal to or less than about 0.007 inch, such as equal to or less than about 0.005 inch. As illustrated in FIGS. 47 and 48, the notches 286 may also have notch depths 620 of between about 0.005 inch and about 0.02 inch, such as between about 0.075 inch and about 0.0125 inch, and the notches 648 may have notch depths 654 measured from the peaks of their flanking lands 646 of between about 0.001 inch and about 0.005 inch, such as between about 0.003 inch and about 0.0045 inch.

The shape of the bottom of the notches 286, 648, and the angle of the notches 286, 648 as illustrated, are the result of the current manufacturing technique. These features may not necessarily, in and of themselves, be critical to the function of the anvil and may vary if necessary. For example, as illustrated, the notch bases are defined by a radius fillet. However, the notch bases may be triangular, squared, or a variety of other shapes. Likewise, the wall angle of the notches 286, 648 could be vertical or less steep if desired. In addition, the depth and the width of each notch 286, 648 may be controlled and defined independently from other notches 286, 648 on the anvil. The volume (or the cross-sectional area) of the notches 286, 648 define the ability of the anvil to entrap and/or sever the elastic strands, such that the severing ability is likewise dependent on the width of the notches 286, 648 based on the materials that we are processing. Thus, independently and accurately controlling the depth of the notches 286, 648 facilitates defining a notch volume (or cross-sectional area) for entrapping and/or severing the elastic strands.

FIGS. 50-56 are illustrations of an annular face of one embodiment of an anvil 658 for use in the apparatuses of FIGS. 2-7. In the illustrated embodiment, the anvil 658 includes the anvil face 602 having a plurality of ridges formed thereon, including a plurality of first ridges 604, a plurality of fourth ridges 660, and a plurality of fifth ridges 662. In one suitable embodiment, the first, fourth, and fifth ridges 604, 660, and 662 are arranged on the anvil face 602 to define a first zone 608 and a second zone 664 along the circumferential axis 276. The first zone 608 includes the plurality of first ridges 604 arranged sequentially along the circumferential axis 276 for performing a continuous bonding operation, as described above.

The second zone 664 includes the plurality of fourth ridges 660 and the plurality of fifth ridges 662 alternatingly arranged along the circumferential axis 276. The fourth ridges 660 define a plurality of interspaced lands 666 and notches 668, and the fifth ridges 662 define a plurality of interspaced lands 670 and notches 672. The fourth ridges 660 and the fifth ridges 662 are configured to perform an intermittent entrapment and cutting operation on the elastic strands 504 (shown in FIG. 27). That is, in the illustrated embodiment, the lands 666, 670 and the notches 668, 672 of adjacent ridges 660 and 662 are misaligned from each other in the width dimension 278 to provide intermittent entrapping and cutting of the elastic strands 504 in the second zone 664. More specifically, the notches 668, 672 of adjacent ridges 660 and 662 may be misaligned from each other in the width dimension 278 to define a groove offset 674 of between about 0.01 inch and about 0.03 inch, such as between about 0.015 inch and about 0.025 inch.

In the illustrated embodiment, a first ridge 604, a fourth ridge 660, and a fifth ridge 662 are arranged sequentially as the anvil face 602 transitions from the first zone 608 to the second zone 664. Accordingly, in operation, the fourth ridge 660 receives the elastic strands 504 routed in the machine direction from the adjacent first ridge 604, and the fifth ridge 662 receives the elastic strands 504 routed in the machine direction from the adjacent fourth ridge 660.

In one suitable embodiment, the lands 666 of the fourth ridge 660 may be aligned in the width dimension 278 with at least two lands 284, and every other notch 286, of the adjacent first ridge 604. The notches 668 of the fourth ridge 660 may be aligned in the width dimension 278 with corresponding notches 286 of the adjacent first ridge 604. In the illustrated embodiment, the corresponding notches 286 aligned with the notches 668 are those that are not aligned with the lands 666 of the fourth ridge 660. Accordingly, the elastic strands 504 circumferentially aligned with the aligned notches 286, 668 may be entrapped by the first ridge 604 and the fourth ridge 660 within the nonwoven fabrics 112, 116. Alternatively, the elastic strands 504 circumferentially aligned with the notches 286 and correspondingly aligned lands 666 may be entrapped by the first ridge 604 and severed by the fourth ridge 660.

In addition, the lands 666 of the fourth ridge 660 may be aligned in the width dimension 278 with corresponding notches 672 of the adjacent fifth ridge 662, and notches 668 of the fourth ridge 660 may be aligned in the width dimension 278 with corresponding lands 670 of the adjacent fifth ridge 662. Accordingly, the elastic strands 504 circumferentially aligned with the lands 666 and correspondingly aligned notches 672 may be severed by the fourth ridge 660 and entrapped within the nonwoven fabrics 112, 116 by the fifth ridge 662. The elastic strands 504 circumferentially aligned with the notches 668 and the correspondingly aligned lands 670 may be entrapped within the nonwoven fabrics 112, 116 by the fourth ridge 660 and severed by the fifth ridge 662. Thus, the staggered alignment of corresponding lands 666, 670 and notches 668, 672 along the circumferential axis 276 accounts for cross-directional movement of the elastic strands 504 in the width dimension 278, thereby severing the elastic strands 504 at least once within the second zone 664.

Figure 54:
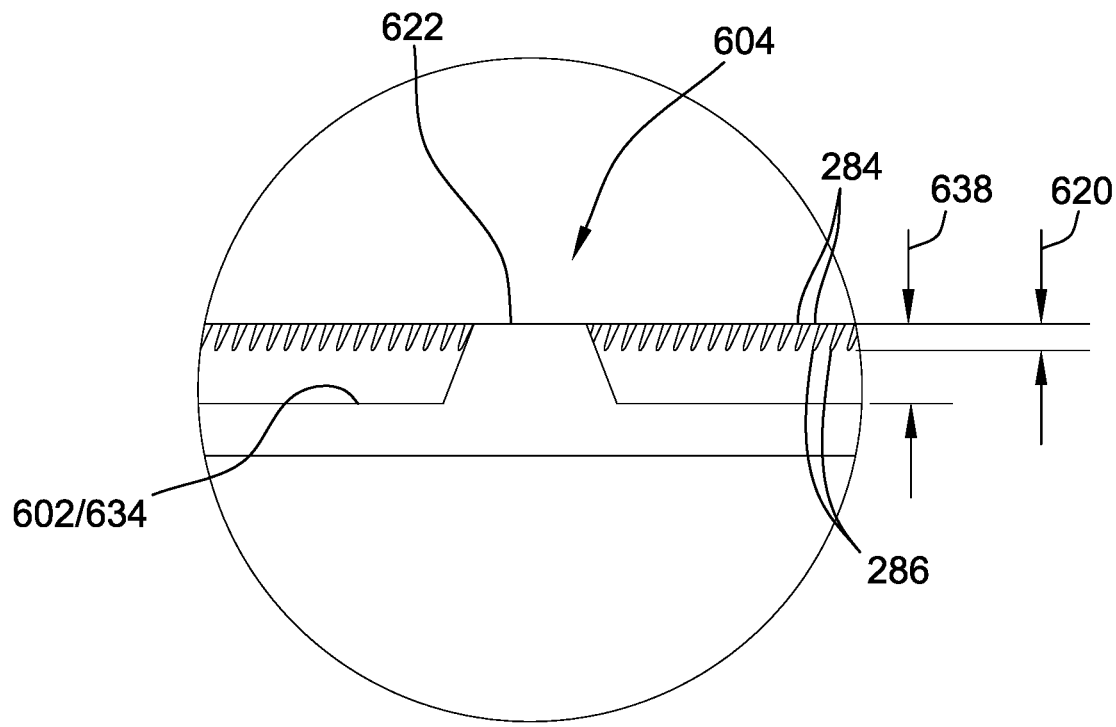
FIG. 54 is an enlarged segment of the anvil of FIG. 53 taken within area 54 of FIG. 53.
Figure 55:
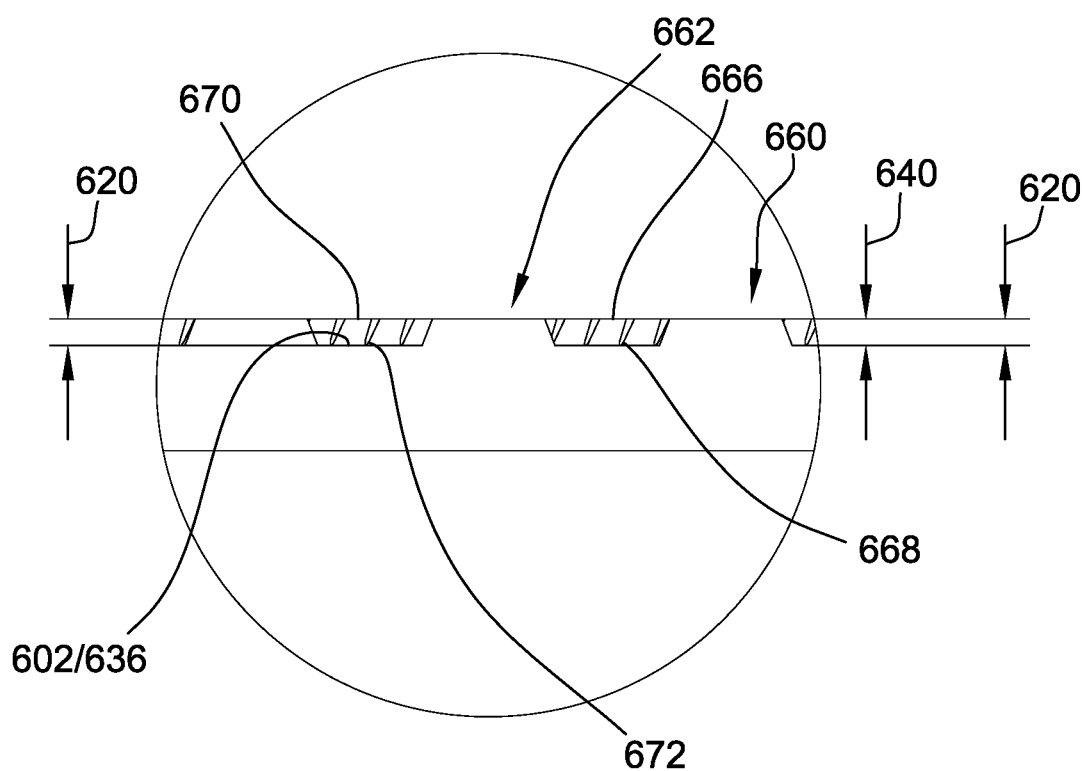
FIG. 55 is an enlarged segment of the anvil of FIG. 53 taken within area 55 of FIG. 53.
Figure 56:
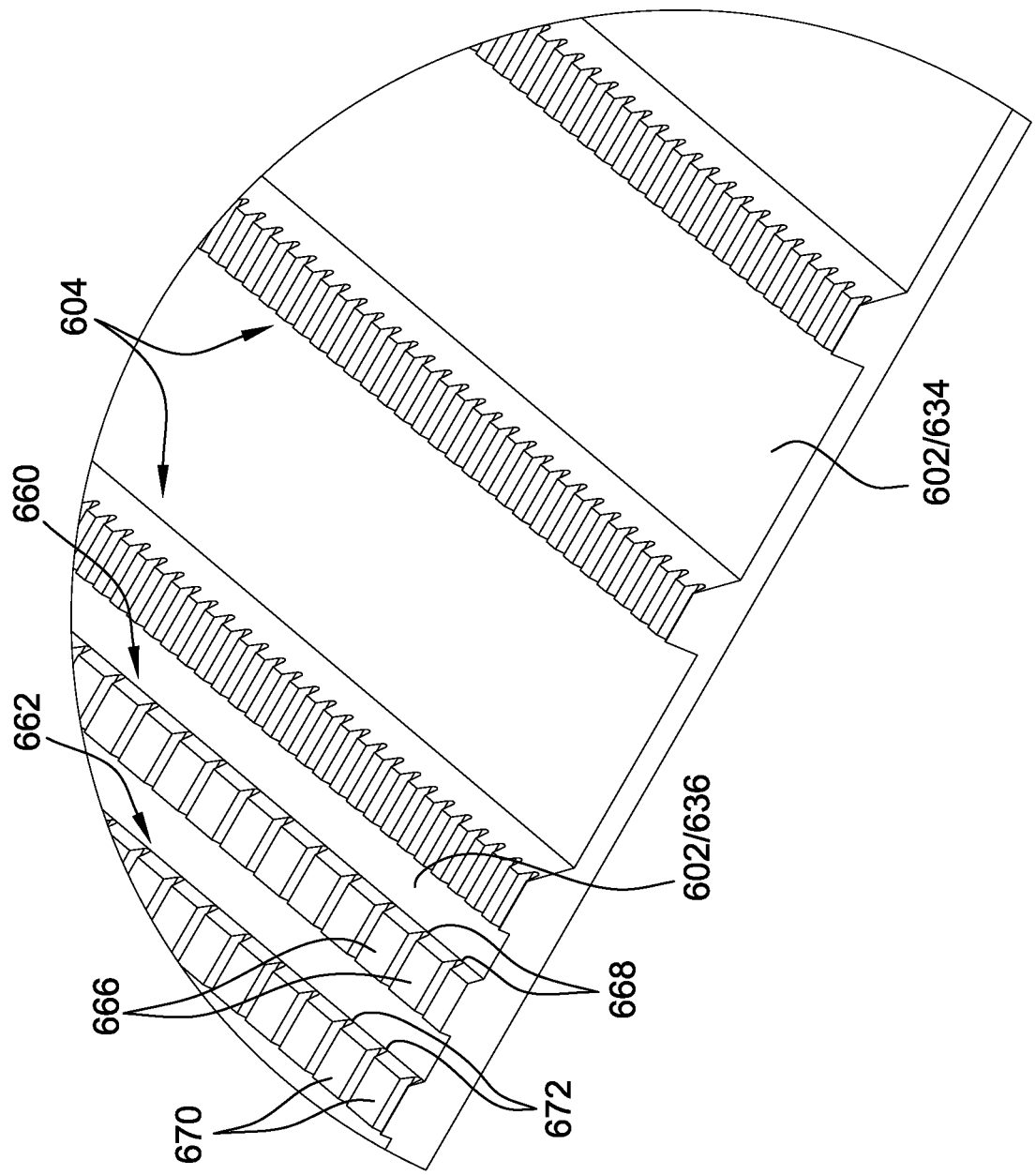
FIG. 56 is a perspective view of a portion of the annular face of FIG. 50.

In one particular embodiment, if the elastic strands 504 have a decitex of between about 300 and about 1240, and if the nonwoven fabrics 112, 116 have a grammage (gsm) of between about 8 and about 30, the lands 666, 670 may have lengths 614 at their peaks of between about 0.010 inch and about 0.25 inch, such as between about 0.030 inch and about 0.060 inch, and widths 676 at their peaks of between about 0.02 inch and about 0.04 inch, such as between about 0.025 inch and about 0.035 inch. Also, in that example, the notches 668, 672 may have widths 618 measured at the peaks of their flanking lands 666, 670 of between about 0.006 inch and about 0.016 inch, such as between about 0.008 inch and about 0.015 inch, and widths measured at their bases of between about 0.002 inch and about 0.02 inch, such as between about 0.004 inch and about 0.015 inch. As illustrated in FIGS. 54 and 55, the notches 668, 672 may also have notch depths 620 of between about 0.005 inch and about 0.02 inch, such as between about 0.075 inch and about 0.0125 inch.

The rotary ultrasonic bonding systems and methods set forth herein are utilized to directly entrap tensioned elastic within a nonwoven fabric without the use of adhesives, thereby providing various functional and commercial advantages. The systems and methods eliminate the complex adhesive delivery systems and costly adhesive materials associated with adhesive bonding processes, and the systems and methods provide a simpler, cleaner, and safer (e.g., cooler in temperature) production environment, with lower power consumption and lower material costs. Also, various functional deficiencies of adhesively bonded materials are eliminated, including adhesive bleed-through, overspay, stiffening, and creep that are common in conventional adhesively bonded materials. Thus, lower-cost nonwoven/film substrates and elastic materials can be utilized.

Moreover, the systems and methods set forth herein facilitate a more continuous production sequence (i.e., increased process uptime) due, at least in part, to the lack of: adhesive-related cleaning operations; adhesive system delivery/reliability issues; heated equipment cool-down periods in advance of maintenance events; cold-start periods; and re-heat or purge-calibrate events. Additionally, a more continuous production sequence is further facilitated by the automatic threading (or self-threading) of severed elastic strands when the system is online, as well as the use of continuously-running, over-the-end elastic spools.

Additionally, the systems and methods set forth herein are usable to attach (e.g., entrapment) elastic strands while also performing other elastic processing steps such as cutting/chopping processes, seaming processes, edge trimming processes, etc. The systems and methods are further adaptable to existing capital asset bases to provide retrofit capability (with customizable configurations if desired), as well as quicker grade-change capability as the attachment zone length changes via a software interface.

The systems and methods also facilitate maximizing elastic performance. For example, the systems and methods facilitate lowering tension at elongation as compared to other attachment methods (e.g., the systems and methods can provide a nearly pure elastic response for stress vs. strain when at least some substrates are utilized). The systems and methods also facilitate minimizing creep (or loss of performance) (e.g., the systems and methods produce elastic materials that are more robust in the face of temperature, time, and end-user solvents (e.g., emollients)) due, at least in part, to the fact that the elastic strands can be entrapped in a thermoplastic substrate, as opposed to being attached to a substrate with a susceptible intermediate binder material.

The systems and methods further facilitate customized aesthetics and functional benefits. For example, gathers are produced by a bonding pattern and/or strand-feed positioning such that size, shape, and frequency are selectable. Also, zoned tension is enabled, in that tension can be controlled by an elastic segment depending upon the desired fabric configuration (e.g., depending upon the desired cross-direction orientation within fabric (among lanes) and/or longitudinal orientation within fabric (within lanes)). Curved attachment is also facilitated if desired. Furthermore, controlled slip/creep for adjustable fit is facilitated, with intermittent or continuous attachment of elastic to the substrate being selectable to enable placement/zoning of live elastic and non-elasticized segments. Also, the systems and methods allow elastic strands to be positioned adjacent more precisely than known systems. For example, the systems do not include adhesive dispensers which can limit the placement of elastic strands relative to each other and, as a result, the described systems and methods provide a greater range of positions for the elastic strands than known systems.

Also, the systems and methods allow for the bond points and attachment points of the nonwoven fabric to be positioned in a variety of locations in machine and cross-machine directions. As a result, the systems and methods provide the ability to control the nonwoven fabric collapsing in both directions due to the force from the elastic strand. In addition, the systems and methods increase control over the functional and aesthetic properties of the elastic nonwoven material. Also, embodiments provide the capability to produce functional and aesthetic geometric and/or text features in the elastic nonwoven material. Moreover, the described systems and methods may provide the ability to control the wear characteristics of bonding modules by reducing zones of uneven engagement.

In addition to the embodiments of the systems and methods set forth above, other embodiments are also contemplated. For example, non-rotary systems of attachment (e.g., stationary (or blade) ultrasonic horns, heat, pressure, etc.) are contemplated. Also, in combination with the rotary embodiments set forth above, adhesive systems may be usable in alternative embodiments. Moreover, latent elastics may be usable instead of tensioned elastics in some embodiments. Then too, the systems and methods facilitate curving (or shifting) elastic strands with less occurrence of breakage, and the systems and methods further facilitate generating a matrix of tensions (e.g., a checkerboard effect), differential ruffling, dead zones, and/or simultaneous incorporation of elastic strands of different decitex.

Notably, the systems and methods described herein facilitate fabricating a variety of elastic nonwoven materials usable in a variety of articles such as personal care articles (e.g., adult briefs, baby diapers, child/adult pull-on pants, contour fit hygiene products, etc.) or medical garments (e.g., masks, caps, gowns, footwear, etc.). Moreover, individual components (e.g., scrim/netting, diaper ears, discreet panels, etc.) of an article can be fabricated using elastic nonwoven materials fabricated via the above-described systems and methods. Other contemplated products in which the nonwoven materials can be utilized include thermal insulation or filters (e.g., associated ruffling or blousing), as well as elastic-topped garbage bags, non-adhesive bandages, hair nets, house wrap, etc.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An apparatus for fabricating an elastic nonwoven material, the apparatus comprising:
    a first bonding module; and
    a second bonding module positionable, in close proximity to the first bonding module, for receiving a first nonwoven fabric, a second nonwoven fabric, and at least one elastic strand therebetween, wherein the second bonding module has a face with a width dimension and a circumferential axis and is rotatable about a rotation axis, the face having a first ridge and a pair of second ridges, each second ridge of the pair of second ridges positioned on one of an opposing side of the first ridge along the circumferential axis, the first ridge defining a plurality of interspaced lands and notches, the pair of second ridges configured to sever the at least one elastic strand when in close proximity to the first bonding module to form one or more discrete strand segments, and the first ridge configured to form bond points that captures the one or more discrete strand segments in a relaxed state,
    wherein the face of the second bonding module defines a first zone comprising a plurality of ridges arranged sequentially along the circumferential axis and a second zone comprising the first ridge positioned between the pair of second ridges along the circumferential axis, and
    wherein the face defines a surface between adjacent ridges in the first zone, and defines a raised surface between adjacent ridges in the second zone, such that a first gap is defined between the first bonding module and the surface, and a second gap is defined between the first bonding module and the raised surface, the first gap being larger than the second gap, the second gap adapted to limit a snap-back potential of the at least one elastic strand severed by the pair of second ridges in the second zone.

2. The apparatus of claim 1, wherein a ridge height is defined between the face of the second bonding module and a radial outer surface of ridges in the first zone and the second zone, wherein the ridge height in the first zone is greater than the ridge height in the second zone.

3. The apparatus of claim 2, wherein the ridge height in the second zone is approximately equal to a notch depth of notches in the second zone.

4. The apparatus of claim 1, wherein a distance between adjacent ridges in the first zone is greater than a distance between adjacent ridges in the second zone along the circumferential axis.

5. The apparatus of claim 1, wherein each second ridge has a radial outer surface that is continuous and free of interspaced lands and notches.

6. The apparatus of claim 1, wherein each second ridge defines a plurality of interspaced lands and notches.

7. The apparatus of claim 6, wherein notches of the first ridge are substantially aligned with lands of the pair of second ridges along the circumferential axis, the lands of the pair of second ridges configured to sever the at least one elastic strand.

8. The apparatus of claim 6, wherein lands of the first ridge are substantially aligned with lands of the pair of second ridges along the circumferential axis, and wherein notches of the first ridge are substantially aligned with notches of the pair of second ridges along the circumferential axis.

9. The apparatus of claim 8, wherein the notches of the pair of second ridges have at least one of a reduced width or a reduced depth relative to the notches of the first ridge.

10. The apparatus of claim 1, wherein the first zone comprises a plurality of first ridges arranged sequentially along the circumferential axis.

11. An apparatus for fabricating an elastic nonwoven material, the apparatus comprising:
    a first bonding module; and
    a second bonding module, positionable in close proximity to the first bonding module, for receiving a first nonwoven fabric, a second nonwoven fabric, and at least one elastic strand therebetween, wherein the second bonding module has a face with a width dimension and a circumferential axis and is rotatable about a rotation axis, the face defining a first zone and a second zone along the circumferential axis, the first zone including at least two ridges configured to form at least one pair of first bond points for entrapping the at least one elastic strand therebetween, the second zone including a first ridge and a pair of second ridges, each second ridge of the pair of second ridges positioned on one of an opposing side of the first ridge along the circumferential axis, the first ridge defining a plurality of interspaced lands and notches, the pair of second ridges configured to sever the at least one elastic strand when in close proximity to the first bonding module to form one or more discrete strand segments, and the first ridge configured to form bond points that captures the one or more discrete strand segments in a relaxed state, wherein the face of the second bonding module defines a surface between adjacent ridges in the first zone, and defines a raised surface between adjacent ridges in the second zone, such that a first gap is defined between the first bonding module and the surface, and a second gap is defined between the first bonding module and the raised surface, the first gap being larger than the second gap, the second gap adapted to limit a snap-back potential of the at least one elastic strand severed by the pair of second ridges in the second zone.

12. The apparatus of claim 11, wherein each second ridge defines a plurality of interspaced lands and notches.

13. The apparatus of claim 11, wherein a ridge height is defined between the face of the second bonding module and a radial outer surface of the ridges in the first zone and the second zone, wherein the ridge height in the first zone is greater than the ridge height in the second zone.

14. The apparatus of claim 11, wherein the at least two ridges comprise a plurality of first ridges arranged sequentially along the circumferential axis.

15. A method for fabricating an elastic nonwoven material, said method comprising:
    positioning a first bonding module in close proximity to a second bonding module, wherein the second bonding module includes a face with a width dimension and a circumferential axis;
    rotating at least one of the first bonding module and the second bonding module;
    feeding a first nonwoven fabric, a second nonwoven fabric, and an elastic strand therebetween in a machine direction between the first bonding module and the second bonding module along the circumferential axis;
    bonding the first nonwoven fabric and the second nonwoven fabric in a first region, wherein at least a portion of the elastic strand is entrapped in the first region between at least one pair of first bond points; and
    bonding the first nonwoven fabric and the second nonwoven fabric in a second region, wherein the elastic strand is severed in the second region to form a discrete strand segment entrapped in the second region by second bond points in a relaxed state, wherein the face of the second bonding module defines a first zone comprising a plurality of ridges arranged sequentially along the circumferential axis and a second zone comprising a first ridge positioned between a pair of second ridges along the circumferential axis, the first ridge defining a plurality of interspaced lands and notches, and wherein the face defines a surface between adjacent ridges in the first zone, and defines a raised surface between adjacent ridges in the second zone, such that a first gap is defined between the first bonding module and the surface, and a second gap is defined between the first bonding module and the raised surface, the first gap being larger than the second gap, the second gap adapted to limit a snap-back potential of the elastic strand severed by the pair of second ridges in the second zone.

16. The method in accordance with claim 15, the method further comprising:
    frictionally engaging the first nonwoven fabric and the second nonwoven fabric in the first region with a first friction force; and
    frictionally engaging the first nonwoven fabric and the second nonwoven fabric in the second region with a second friction force greater than the first friction force, the second friction force sufficient to limit a snap-back potential of the elastic strand severed in the second region.

17. The method of claim 15, wherein the first region and the second region are continuously disposed in the elastic nonwoven material and adjacent to each other.

* * * * *